United States Patent
Shaw, IV et al.

(10) Patent No.: US 11,535,829 B2
(45) Date of Patent: Dec. 27, 2022

(54) MICROORGANISMS ENGINEERED TO USE UNCONVENTIONAL SOURCES OF PHOSPHOROUS OR SULFUR

(71) Applicant: Ginkgo Bioworks, Inc., Boston, MA (US)

(72) Inventors: Arthur J. Shaw, IV, Belmont, MA (US); Colin R. South, Lexington, MA (US); Johannes P. Van Dijken, Leidschendam (NL)

(73) Assignee: Ginkgo Bioworks, Inc., Boston, MA (US)

( * ) Notice: Subject to any disclaimer, the term of this patent is extended or adjusted under 35 U.S.C. 154(b) by 609 days.

(21) Appl. No.: 16/201,425

(22) Filed: Nov. 27, 2018

(65) Prior Publication Data

US 2019/0233800 A1     Aug. 1, 2019

Related U.S. Application Data

(62) Division of application No. 14/914,817, filed as application No. PCT/US2014/052841 on Aug. 27, 2014, now Pat. No. 10,174,296.

(60) Provisional application No. 61/870,469, filed on Aug. 27, 2013.

(51) Int. Cl.
| | | |
|---|---|---|
| *C12P 1/02* | (2006.01) | |
| *C12P 1/04* | (2006.01) | |
| *C12P 7/00* | (2006.01) | |
| *C12N 9/02* | (2006.01) | |

(52) U.S. Cl.
CPC ............. *C12N 9/0004* (2013.01); *C12P 1/02* (2013.01); *C12Y 120/01001* (2013.01); *C12P 7/00* (2013.01)

(58) Field of Classification Search
CPC . C12Y 120/01001; C12N 9/0004; C12P 1/02; C12P 7/00
See application file for complete search history.

(56) References Cited

U.S. PATENT DOCUMENTS

2004/0091985 A1 * 5/2004 Metcalf .................. C12P 19/36
                                                        435/189
2006/0051847 A1    3/2006 Gunnarsson et al.
2012/0295303 A1    11/2012 Herrera-Estrella et al.
2015/0125934 A1 * 5/2015 Kuroda .................... C12N 1/16
                                                        435/254.2
2017/0226493 A1    8/2017 Callewaert et al.

FOREIGN PATENT DOCUMENTS

| CN | 102282156 A | 12/2011 |
|---|---|---|
| EP | 2034026 A1 | 3/2009 |
| WO | WO-2010/058298 A2 | 5/2010 |
| WO | WO-2012/147556 A1 | 11/2012 |
| WO | WO-2014/024998 A1 | 2/2014 |

OTHER PUBLICATIONS

Costas et al., "Purification and Characterization of a Novel Phosphorus-oxidizing Enzyme from Pseudomonas stutzeri WM88," J Biol Chem, 276(20): 17429-17436 (2001).
International Search Report dated Feb. 24, 2015, from PCT/US14/52841.
Jakobiak et al., "The bacterial paromomycin resistance gene, aphH, as a dominant selectable marker in Volvox carteri," Protist, 155(4):381-393 (2004).
Kanda et al., "Application of a Phosphite Dehydrogenase Gene as a Novel Dominant Selection Marker for Yeasts," J Biotechnol, (182-183): 68-73 (2014).
Nielsen et al., "Metabolic engineering of yeast for production of fuels and chemicals," Current Opinion in Biotechnology, 24(3): 398-404 (2013).
Nielsen et al., "Production of biopharmaceutical proteins by yeast :Advances through metabolic engineering," Bioengineered, 4(4): 207-211 (2012).
Sodoyer et al., "Antibiotic-Free Selection for Bio-Production: Moving Towards a New "Gold Standard"," 531-548 (Apr. 4, 2012).
Supplementary Partial European Search Report for European Application No. EP14839721 dated Dec. 15, 2016.
Tai et al., "Engineering the Push and Pull of Lipid Biosynthesis in Oleaginous Yeast *Yarrowia lipolytica* for Biofuel Production," Metab Eng, 15: 1-9 (2013).
Tsigie et al., "Bioethanol Production from Yarrowia lipolytica Po1g Biomass," Bioresource Technol, 145: 210-216(2013).

* cited by examiner

*Primary Examiner* — Maryam Monshipouri
(74) *Attorney, Agent, or Firm* — Foley Hoag LLP

(57) ABSTRACT

Disclosed are genetically engineered organisms, such as yeast and bacteria, that have the ability to metabolize atypical phosphorus or sulfur sources. Fermentation methods using the genetically engineered organisms are also described. The fermentation methods are robust processes for the industrial bioproduction of a variety of compounds, including commodities, fine chemicals, an pharmaceuticals.

20 Claims, 36 Drawing Sheets

Specification includes a Sequence Listing.

Figure 1

Pseudomonas stutzeri WM88 ptxABCDE

```
atgacgccccatccgatacaggacgccgtgctgcgggtcgaccggttgagcgtcgtctatccaggcggcgtgacagcc
ctacgcgatacctcgattgcatttcggcgtggtgagttcaccgtgctgcttggtctctcgggcgcaggcaagtcgacc
ttgctccgtagtctcaatcgactcgtcacgccactggcggcagtgtcaccagcgaactcggtgaactcggcagcggc
tggccttgcgtcagcatcgtcggcgtaccgccatgatctttcagcaccaccagctaatcgaacgtcaaagcgcactg
gctaatgtgctgaccggtcggctggcctttcacaacacgctccgctcgtgtttcctctgccgcgtgccgatcaggag
attgcgctcagttgcctcgctcgggtcggtctggcagacaaggcgctaagccgggtggacaaactgtccggtggccag
cagcagcgggtaggcatcgcgcgtgcgctagcgcaacagccggcgatcattctggccgatgagccggtagccagtctc
gacccggccacttcggtccgtgttctcggattgctgcgcgacatctgcaaggaagacggcatcaccgccatcgtttcg
ctgcatcaactcgaatatgcccgccgcttcgccgatcgcgtcgtcgggctggccgattctcagatcgttttcgatgcc
gcgccctcggaactcaccgatgcgcagcttgagcgcatctatgcaggcgctctacgactcagccagcgaatgctccg
gctgaaccacctgtcatgctcgaaccttcactggagatgtcccgatgaaacgcttatccgcgctcttattgacttgct
tgctgtccgctgtttcaagtttgtccgccctagcggccgatgccgatccggatgtgctaaaggttgccctgctgccgg
acgaaaacgcctccgagctgatcaagcgtaaccagccgctgaaggattatctggaagagcatctggacaagaaggtgc
agctgatcgtaaccaccgactattcctcgatgattgaggcgatgcgctttggccgtatcgacctggcgtatttcggtc
cgctgtcctacgtcatggccaaaagcaaaagcgacatcgagcccttcgctgccatggtcatcgacggcaagccgacct
atcgctcggtgattatcgccaatgtggcgtcaggcgtgaatgagtatgccgaccttaagggcaagagaatggcctatg
gtgaccgggcatcgacgtccagccatttgattcccaaaaccgtgcttcttgagacggccgatttgacgggtgggcagg
actacgaacaacattttgtgggcacgcatgacgccgttgccgtcaacgtggcgaacggcaacgccgatgcgggtgggc
tgtcggaggtaattttcaatcacgcagccgaacgtggcctgatcgatccgagcaaggtgaaagtacttggttacagcg
gcgaataccccagtaccctggcgatgcgctcgaacctgagccccgagctgaaaaccaaggtgcgggatgtattcg
tcggtatcgacgatcccgaagtgctgcgcaacttcaaggccgaggccttcgcgccaatcaccgacgccgactacgatg
tgatccgcaacatgggatcgctgctcggcctcgacttcgccacgatgtgagcaccgatatgtcttctcattacgacgt
gcaggcgctgcctgcagagcaacgcgagcacatccttcgaggcttcggcctcggttggtggcgccagctggggcaggt
ggcgattgtattcggagtggtgctgttggcctgctggtacgtggggctgctcgatgccaccacgctgctgaacgggct
gccctccatcgcgaccctggcaggcgaggccatgccgccagactttcgggctatcgaagctggattcgcccttgat
cgacaccttggcgatgagcatcgccggtacggccatcgcagtggtgttctcgctggtggtggccttcgttgcagcgcg
caatacggcgccgcacccttgtgttcggtgttgcccggtgctgctcaatgccctgcggtcggtgccggagctgat
catgggcatcatcttcgttgcagccgtagggttcggcgccttgccgggcgtgcttgccctgggtctgcattcggtcgg
catggtcggcaagttcttcgccgaggccatcgagcacgtcgacgaagcgccggtggaagccgctcgggcggcggggc
tacgccgatgcaagtgctgctgcacgcggttttgccacaggtgacgccgcagttcgccgacgtggcgatctaccgctg
ggaatacaactttcgcgcctccaccgtgatgggcatggttggcgccggcgggtatcggcttcgaactcatggctcgct
gcgcatcatgcagtaccaggaggttgcagcaatcctgctggtcatcctggccatggtcacgctagtagacgccttcag
tggcgtgctgcgcaaacatttcaaataggacaaaccatgctgccgaaactcgttataactcaccgagtacacgatgag
atcctgcaactgctggcgccacattgcgagctgatgaccaaccagaccgacagcacgctgacgcgcgaggaaattctg
cgccgctgtcgcgatgctcaggcgatgatggcgttcatgcccgatcgggtcgatgcagactttcttcaagcctgccct
gagctgcgtgtagtcggctgcgcgctcaagggcttcgacaatttcgatgtggacgcctgtactgccgcggggtctgg
ctgaccttcgtgcctgatctgttgacggtcccgactgccgagctggcgatcggactggcggtggggctggggcggcat
ctgcgggcagcagatgcgttcgtccgctctggcgagttccaggctggcaaccacagttctacggcacggggctggat
aacgctacggtcggcatccttggcatgggcgccatcgactggccatggctgatcgcttgcagggatggggcgcgacc
ctgcagtaccacgaggcgaaggctctggatacacaaaccgagcaacggctcggcctgcgccaggtggcgtgcagcgaa
ctcttcgccagctcggacttcatcctgctggcgcttcccttgaatgccgataccagcatctggtcaacgccgagctg
cttgccctcgtacggccgggcgctctgcttgtaaaccctgtcgtggttcggtagtggatgaagccgccgtgctcgcg
gcgcttgagcgaggccagctcggcgggtatgcggcggatgtattcgaaatggaagactggctcgcgcggaccggccg
cggctgatcgatcctgcgctgctcgcgcatccgaatacgctgttcactccgcacataggctcggcagtgcgcgcggtg
cgctggagattgaacgttgtgcagcgcagaacatcatccaggtattggcaggtgcgcgcccaatcaacgctgcgaac
cgtctgcccaaggccgagcctgccgcatgttgaatccggtctggctgaagagcctggtagcgatcgttcaaacaggca
gttttcagagcgcggcgagggcgttgggctggcccagccgacggtgtcgcagcacttgcagaagcttgaagagcagg
tcggcgtaacgctggtgcagcgcagtcgtagcggctgccagcctaccacacgggcgctggccttcatgccgcatgcga
ccgccttgctcgacatgcacgcccgggcgctagaagccctgcatggcaatcgtgagcgcgtcggggccagctccaaca
tcggcacctaccttctccagccattcgtgcgcaactatctgacgaccgcaaatgagagggcgaggtggatctgcgca
tcgccgccaacccggatgtggccgaccagctactggcgggccagctcgacgccgcgatcatggaatggtggctacctc
```

Figure 1 (continued)

accccgacttcgaataccgcctctggcgggtcgagccgctggtgcttatcgtcagcccgaccatgcgctggctgaag
cagggtgcatagaacgtgatcgtctggtggacctgccgatgctgggaggtgaaccgggtagcggtacctag Pseudomonas stutzeri WM88 htxABCDEFGHIJKLMN atgtttgcagagcagcaacgcgaatatctcgacaagggatatacgaagattgaaagcttttttctccgcggaggaagta
gcgaagattcttgaagacgtcaagcaaattgaattgggagctattggcgtagcttcggacaatgagacttaccagttc
gaaaagaagaatggcgagacgacgaagctactgcgtcgcgtcgagaatcctcacctttatttcgatgcaatagattct
ttggtcaggtcggaaaaaatcgtcgatttgcttcggcatttcctgggcgaaaacatccgtttgcacaatagcaaaatc
aacttcaagccgccatcaggcgcgccagtccagtggcatcaggactgggcattctatccccacacaaacgatgatttt
cttactctcggaattttcctcgacgagacaagtgagaaaaatggcgcgatggcatgcttgccaggctcccacaaagga
aaagtgtacgaccaccggaacgtcgagacgggcgagttttgccacgcgatctctcgctccaactgggacgaagcgctc
gacccgacagaaggggagttactgacgggacccgtaggaactgtcacgttgcatcacgtccggacccttcatggttca
ggcccaaaccactcaacgatcaggcggcgttttctgctcatcggctatgccgcggctgatgcctggccacttctgggc
tgtggcaactatggggattatgaaagcctcatggtctctggccgatccaccgtattcccgcgcatggtggaactccct
ttgactgtcccgtatccgttgtcgatgtacggtgatcgcatctttgaaagtcaacgagctttgactcaaaagtactac
tgaagtcttttaactcactgaggtcataatgcaagtttttactctgtttttcgaaattcaagaaggcgttaacgcgcgcc
attcttgcctttatcgccacaatcatagtgtgcacacccgcgcaggcagctgaggttgtcaatggtaaacttcacctg
cgttttgcaattgcgccgatgcgtccaacgcctagccagaccatcaaagagtttgagccgatattcaagtatctcgcc
gaccagctcggcgcgacctatgaaatcgtctcccccggaaagctgggcggcaatatctgtggcaatgacaaatgccat
gtcgatgtgggctggctcggaccctggggctatgtcttgtcgaataaaaaggccggcaccgaagtgcttgcaacggtc
aagtaccgcggggagccgttctacaaagccctcattgtcggtcgcgccgatctgccgatcaaaaaatggcccgaggac
gcgaagggtttgaagctgtcactcagtgatcagggcaacacttctggctggctcatcccgatggcgtacttcaagagc
atcggcatcgaccctgcgagctattttgaatatcgtgaaggtgccacgtttggccagaacgaatcacagattcagcac
ggactgatcgacctcggatccgatatggatcggggccggaacgggatgatcgaagcgggtcaaatcgatccttcgaag
tccaagatcgtgtgggaatccagcaagctgccgaacgacgcgatatccgtgccgaaggattttgatcctgctctgaaa
gcgcgcatcacggaaatactgacgtccttgtccgaagagaaagcacagtcgctgatgggctcgggctataacggcttc
gtgaaggcaaagcacagcgattacaaggtaatcgaagacgccggccgcatcctgggaaaactgtaaagcacgagggt
ccgttcttggatgagggcagcggacgacaaggtggactgacgcacgccagctccttgtctccgctgcacgaacatacg
ggcgcgcatcgcaataccacagaggatgaaccaatgaatcagcgaatcgaagaagtcatgctggctaatgtcaagagg
gacgtagccaggagaaagcggcattttgcaacgtcggtcgtagtactcagtttgctggcagtggcctggtacgtgtgt
cagatagaattccagaagctaggcgccggtttaccgagactatggtcattcgtcgtgcagatgtttccacccgacctg
agcgacctggacgtcattctaaaaggggctggcgagacgctcgccatggcgacgattggcacgatattcgccacaatc
attgcatttccgctggcactcatggctgcgcgtaatacctgtccgaacaagtggacctatcgggtatcccgcgccatc
ctgaacgccagccgcggcacggagacatttgtctatgcacttgtatttgtagcagcagtgggcttcggtccgttctcc
ggcgtactggccattactttccacatggtaggggcaatcggcaaaatgtttgctgaagccatcgagcccgttgaccaa
gggccgttggatgcgctcgccttgaccggtgccagcagggcaaagattatccgctacggtctgatcccggatgttatg
ccgcacctgatcgcgagcgttctatacatttgggaattcagtgtcagaacgtccacagtactgggcatcgtaggcgca
ggtggaattgggcagaccctgaaagatactgtggacttgttggaattcaacaagatgattacggtactggcggttgta
ttgctgatggtgtcggcaatcgatttcatcagtgaccggctcaggtacttgatattggacacaaaacgcgagggattc
gaaactctccctgcgaataactgattgcttcacgtattactggaagggaggttcgcaatgaaagatgtagcgttgcag
ttaaagaatgtcggtaagtcatacggcaataaagttgtcctggaatcgattgacttcgaagtacgtcacggctcaatg
gttgccttgctcggcacaagcggggcagggaagtcgacgcttttccgatgtctcactggccttgagccgattgactcc
ggttctatcgtggcgctcggagaatccatacatgaactgtctccggcgcgtctgcgggcagtacgtggccagatcggg
ttcgtgttccaacaactgcacctggtgaaaaggttctcagcactcgagaatgtattgggtgcgcgtctggcagagatg
cccatttggcgcgtcacattgaaaagcttcagccgggctgacaaagtgctcgcgttcgaatgtctggacgggtcggc
atgctcgattatgcaaacacgcctacgcaactgctgtcagcggtcagcaacagcgtattgcgatagcgcgagccttg
gcgcagaagcccaagattattattgcggacgaacccgtctccagcctcgatccgctgacggcgcgtcggttctgcaa
acgctgaaagccgcggctacagatcttaatgtcgcggtcctgtgcagcctgcaccaggtagacctggcccgtgagttt
ggcgaccgcatcgtgggcatgcgcgacggacgtgtcgttttcgacggcacgccagcggaattcaccgacgagcgcgtg
catgcgctttaccaggtgccgctgggaagatgcaccagcggccgagagcgacgcgcagcactcggtggccggtctgg
ctgtggcatgagggcgaagcgatgaccacatccacacgccccatacccgtgccgccccagggcaccgcactgcactg
gcacctgagcgcgcccctacaacgccaaacatctgctggtgctgatcgccgtcatggtgctgttgttcgtgaccggaca

Figure 1 (continued)

```
acgcaccgaaatggaccgcatggtggccatgacggcacaggccgtggccaagaccgtgggcctggctgacgattcaca
agtcgcgcgcggcttgtcgcgcgtcggtcaagccatgtggccaccgccatcgcagaaaccgaagaggtgggccggat
tcaggacctggatcgccagaagctgcccctgttctcgcacatcgagacccaggagcgcgtcgagcagaagatgaatct
ggacacgctgaagatggaagccacgacggaaaccgtcgaagtgctggtcaagccggtcggctatgtctggacggtttt
catcaagatgatcgagacctggagattgcgctgtggggcacgatcctgtcggtgctggtgtcgattcccctggcgtat
ttcgcggcccgcaactactagccccaaccgttttacctacaccgctgccgcggcaccatcagtctgctgcgttcagc
gccggaactcatcgtcgctttgttcctggtgctggcctacggctttggccccatcgctggcgtgctggcgctgggcct
gcatgcggccggcttcctgggcaagttctacgccgaggacatcgagaacgccgacaagaagccgcaagaggcgctgga
ggccatcggcgcgggcaagctcaagacgctgtggtacggcgtcatccccaggtcttgccgcaatacatcgcctacac
cgcctacatcctggaccgcaacctgcgcatggccaccgtcatcggtctggtgggcgcgggcggcatcggccaggaact
caagggccgttttgacatgttccagtacggccatgtcatgaccatcctgatcgcgatcttcgtctttgtgttcgtgct
ggaccagttgcaggcgcgcatccgcgccaagctgatctgaggcgaccgctgacaacaaggaacaacatgacaaacact
tctgaagcaccggatcgtgcgcagtggctgcggctgtggtcggccttgccggccgcagcggtcaaggccctggcggcc
gatctggcgggccagcaccgggtcgaagacctggcgttgccgcaatccggtctgggcctgctgccgctgaccgacagc
gccctgggcgataccctatttcatcggtgagattcccttggcacaagcgcatgtgcgggtcacgaccacccaagggcag
tcgatcgaaggcgcggccattctggtggacgaccgtgccggtgtggcccgttccatggccatcctggacgcggtgctg
gcggcccgcatgccaggttgtgaagcggccctgcggttgctcacccagggtgcgaccgccgtggcggaacaaggccgc
cagcgccgcgccttactcgcggccacgcgggtggactttgccctgctgggaacgaacgaggaggacgatgatgaatga
gactgggatggcggcggcaccggcagaagccgcgtggcgcatctggcaagcgccgcgccagcaaacggcgtttcgcca
gttgatgaccgcgttttcctatccgggccgcgtggtgccactggccgatggcgctgaatcggcgctcctgctggtgtt
gaccaccctggtggacagcgcctgtgcgctggccgatccgctgcacgcgctatcaagcgacgatctgcgccgactggg
cgtgcgctcggccagtgtggaggcggccgagttcgtgctggccgatggcaaccgtttgctggaggccacgccgcgcct
gggatcgctggaaaaccccgaacaaggcgcgaccgtggtgatgcgcgtctcccgtttcggtgagggtccccatctgcg
gctcaccgggccgggtattcaacacgagcaggtgctgcaggtcagcggcatcgatccgggctggtggaagcaacggtc
cgaatggaatgcccacttcccgctgggcgtggacctgattctggtgagcgggcacgaggtcgcggtattgccccgaac
cacccacatcaacctcaaaggagcccactgatgggatacgttgccatcaagggcggtggccgggccatcgccggtgcc
gaagccgccgtcgaagccctgcgctgcgccgaagggccagcgggtacgccgctcacgctgtcggccatcgaacagcag
ttgcggttgctgacatcgcgcgtcgtgtcggaagggggcctctaccaccccacgcctggccgctctggccatcaaacag
atgcagggcgacacactggaagcggcgttcgctctgcgcgcctaccgctccaccaagccacgcctgatggatgtgccg
gtgcaggacacgagccgcatgcgcctaatccgccggatttcgagcgctttcaaggacatccccggcggacagatgctg
ggcccgaccaccgactacgcgctgcgcctgatgcgtctggatttggccaacgagtcgcccgaggactttcgcgcggtc
tcgcggcggtttctggacagcgtggccgacaccgacctgcccgacagcttccccaaggtggtcgatgccttgcgtgac
gaaggcttgctgccgccgctgacccggcgcgcccatgcggcgttcgacatcacccgcgacccgctggttttcccagtg
ccgcgttcggcggccctggccaccatggcacgcgccgaaaccggctcgctcttggcgattgcgtattccaacatgcgt
ggctatggcgacgtgcaccccaccatcgccgagctgcgcgtgggctatgtgccggtgatgctgccgcacccggtgaca
ggcgagcccatcgaagccggtgaggtactgatgaccgaatgcgaagtggtggccatgtttgagggtgatgctaccgac
ggcccacccactttcaccctaggctatggcgcctgtttcggtcacaacgaagtcaaggccatcgccatggccatcctc
gaccgcgcctgcaaaagggtatgcgcgacggtcccagcaaccgtcggaagacccggaattcgtgctgctgcacgtc
gatggcgtggattcgatgggctttgccagtcactacaagatgccgcactacgtgaccttccagtccgacatggaccgg
ctgcgcaccacgcaggacaaggcaaccgcacaaccgacccaagaaggagcgccatcatgaacccgggctacgaactgc
ccctggacgaggcgggctacagcttcggcttcctggacgaatacgccaagcgcgaggtgccgccaccatcctcaagg
cgatcagcatccccggttaccagacgccctatgcctcacgcgaaatgcctatggggcgcggctttggcaccggcggtc
tgcaggttacgctgtcgctgattggcgagggcgacaccctgaaggtgatcgaccagggcgcggacgactccgtcaacg
cggtgaacctgcgtcactttgtggaactgacctgccgggcgtggacaccacagaacacgcttgatgccactctga
tccagtcgcgccaccgcattccggaaacgccgctgaccgaagcgcaggtgttgatcctgcaagtgccgtatccggacc
cactggtggtggtggaaccctccgaggctcgacgcaaggtcatgcacggcgaaggcgactattcgcggctgctgacca
agctgtacgaggacatcgtgcagtttgacgagatcaccatctcgcaccgctaccccacgcgcatcaacgccactatg
tgatcgacccagcccgatcccgcgctacgacgtgccgcagttgcaccagagcccggcgctgatcctgctggtgcgg
ggcgcgagaaaaaatctatgcggtgccgccgtacacccgcgccgacccgctggcgttcgacgcgtgccattccgca
ccgaagacttcaccaacgaacacggccagcgccgcgcctgcgaacggtgcggcgccaccgacagcttcctcgacgagc
tcattgccgacgatggcggcaagcactggcattgctcggactcggattttgcaatagccgtatggcccgccaggctg
aacaagctcaggagaccacggtatgaaaaaattctggaagtacgcggactgaccaagatccacggccggggttgcga
actctgcctggagagcactggccccgacatggacaccaacatctgcccacactgtggctcggtggtggcctgccacaa
catcagcctggacctgcacgagggcgagatcctcggcatcatgggcgagtccggcagcggcaagtccaccgtggtcaa
```

Figure 1 (continued)

```
gacgctgttcttcgacgatgagcccaccgctggtgaagccctgttttttgacggcgagcgccagtgggacatgttcgc
gctcaacgccgcgcagcagcgctggcttgcgcaaccaccgctttggcatggtgtaccagaacccgcatctgggactca
atttcaacgtctcggccggcggaaacatttgccgagcgccttgctgatgagcgacctggcccactacggcgaaatccg
cgaacgggcgcgcagcttgttggcgcgcactgaggtgttggcagaacgcatggacgagtcgcccaagaagttctcggg
cggcatgcagcagcgcgtgcagatcgccaaggcactggccacccagccgccgctgctctacctcgacgaggtcaccac
cggcctggacctttcggtgcaggcgcgcatcctggacctgattctggaaatccagcaggagctgggcaccgccatgat
cgtggtcacccacgatctgggtgtcatccgcctgctgaccggacgcacgatcgtcatgaaatacgccgcggtcatcg
aagtccgggctgaccgaccagatcctcgaagaccccagcacgcctacacccagcgcctggtcgcgtcggcttctctg
aggaaacctgaatcatgcaagaagccatcctcaaaatcgaaggtctctccaaacagttccagctgcacgaccagaaca
aactgatcccgtcgtgtgcacaggttcaactggaggtgtttgccggcgagctgaccgcgctgatcggcccgaccggcg
ccggcaaatcgtcggtgctcaaggccatttaccgcacctacctgcccagcagtgggcgcatcctttaccgggacgcca
acggtgccatcaccgatctggcccaggccagcgaacaccgcatgctggagctgcgcaagcaggacctgggtttcgtca
cccaatttctgcactgtctaccgcgcaagtcggcggtcgaggtagtggccgagccgctggtgcagcggggcagcccgc
gcgaagctgctgccgagcgcgcgcgcgaactgctggccctgctcaacgtgccggaacgcttgtgggcggtaccaccg
ccaccttctcggcggcgagaaacagcgcgtcaacctggcacgcgggctgatcgcccggcctcggctgctgttgcttg
acgaacccacggccagcctagacccgtccaccaccgaccgcgtggtggagctgttgaagtccatcaaggccgaaggcg
tggccatgctggccatcttccacgaccccgaacttgtccgacgcctggccgatcgcgtcgtaaccctcacgccccgg
tgtctgcggcggcattgctggagacctgtgcctcatgaatcccatttgctgacccatgcccgcgtggtgttccccac
cgaagtccgtgacaacgtggccatcctgatcgaaggcgacaccatcacagcatcgaccggccagcagcgcaggtgcc
accgagatcgacctgcgcggctcgcaccctgatgccaggtctgatcgacctgcactgcgacgcaatggagaaagaggt
ggagccgcggcccggcgtgcacttcccgctggagttcgcctgtgcccaggccgacaagcgcaatgcggcggccggcat
cacgacggtgtttcatgccctgtccttttgccaaccacgagctgggcgtgcgcaacaacgccttcgccgccgagatcgc
ccgttcgattggcgactggcaggccatgccctgatcgacaaccgggtgcatgtgcgttacgaggtgacggacgaaac
ggcgccgccggtgctgtcggcgctgctgcaggacggtcatgcgcacctcatgtctttcatggatcacagccccggtca
gggtcagttccgcgatgtcgaggcgtaccgcgcctacctggccaagacctacaagaccgatgaggcgcagatcgacga
catcctggcgcgcaaagccggggccgcacaggggcgccatgcggcgcatggagcagcttgcggaactggcccgtgcgtg
cggcgtgtccattgccagccacgacgacgacagcccgcagaaagtggcgaccgtcaaggccctggcgctgtggtgtc
ggagtttccggtgaacctggagacggcacaggcgcccgtgcacaaggcctggccaccttgtttggcgctcccaacat
cctgcgcggcaagtcccagtcgggcaacatgcgtgccctcgatgccgtgctggccggtgtcgccgactgctgtgcgg
tgactactcgccagcggcgctgttgccgtcggtcatgcgcttgccgatctggccggcatccccctggccgaggctgt
ggccctcgtcacgtgcaacccagctcgtgctgcaggtttgcacgaccggggcgagatcgccgtgggcaagcgcgcaga
cctgattgccggtcaaaaccatgggcggactgccacaggccgagcgggtctggtcgggcggtaaagcttcgctggtcgc
gcattttgaccacgcctgagagggactggcacatgcgaactcgcctcatctacgtggtcggcgcctcgggcagcggca
aggacacgctcatggccatgccgccagaagctggcgggtgatcccagggtgtgttttgcccatcgctacatcaccc
gacccgcaacggcaggcggcgaaaaccatgtggccttgaccacggaggaattcaccgctcgccagaacggcaagctct
ttgccatgcactggtccagccacggcctgcattacggaatcggcatcgagatcaaccagtggctgggcaaaggcatca
cggtggtgatcaacggctcgcgggaatacctggacgaggcccgccaacgttaccgggagctgctgccggtgacgattg
acgtggccaccaccgtgctgcgtgatcggctgctggcccgtggccgcgaggatgccgaatccattgagcagcgcctgc
accgccatgaaacgttgcgcctgcagcccgtgccggtgtgctcatccagaacaacggacccgtcgaggtggccggcg
aagcgctgatccggttgatcgcagaacacacccaaggagcgccagtatgcgtgtgagttttctgggcacgggcgctgc
gggcggggttccgctctacggttgcacctgccggcctgtgaacgcgcaaggaccgagccacacttcgtccgccgcc
ttgcagcgccctgattgaatccggaggtacccgggtgctactggatgccgggctgatggaccttcacgaacggtttgc
gccgggtagcctggacgcgattgttctcacgcactaccacccgaccacgtgcagggactctttcatctgcgctgggg
taaggggacgcccatcacagtctatggcccaccagacagcgaaggctgccgcgatttgttcaagcaccctggtgtact
ggccttcgagacggtgcacaagttcgaggccttcaccgtcggggcgctgcgcctgacgcccctgccgctgcttcactc
caaacccacgctgggctatgccatcgagggcacccagggccaacgcttcgcctacctcacagacaccctgggtttgcc
gccgaagtcggccaagttcctgcgcgcctgggcgactttgacatggccatcgactgttcctatccgccgcacccgac
cccgaaaaccacaacgattgggacgaagcacatcggtgtgccatcgaatctggtgcccgcatcacctggctcaccca
tgccggtcatgcgctggacgactggatgatggaagagacgccgagcgtcgcaagtcatatccggctggcccgggacgg
cagcacggccgacataccgtcccaaacgcaatgaacgcgccgctggcactggccctgtcggtggccatgcacgtcacc
tggaacctgatggcacggcatttgcccagggaatcgaacccgctgtggtgggtgttgctcgcccatctggtgctgttt
gcgccctgggggttctgggagctggcgacaaccgtcgtttggtcactggagatgacgctgctactgatcgtatcggcc
actgcgaatgtggtttattttctccggtctggccagggcctacgagcacgcacggtcgcactggtctatcctctggtg
cgcagttcacctcttttcattgcgatctggggcacgctgttcttcggtcaaaatctcccgccattgcctggctgggc
```

Figure 1 (continued)

```
attggcatcagcgtgctgggcttgctcgtcatggcatcgagtgctcaacaggggtcggatcgacgagcattccgatgg
gccatgctggccatgttggcgacaagcgtttattccctgagtgacaaggcggccaccgaacacatcccaagcttcatg
gggctcgtggttttctgtccgtcggctacctggcatcctggatcagcatgaccttgcgcatgcatcggcacaccgc
agttgggtgccggcacagcgcattgatctcgcgtcgctggctcttggcggaacctgtatcggtctcgcctacgccttg
gttatccacgccatgcgccagttgcctgcggcggaggtcgtgtcgtacaccaacgccggtatcgtgctcgctgcagtt
ctctccattttttgttcaatgacaaagtcggatggcaaaagagaatcatgggggtcgtgatcatcacgagtggtttg
gggtgcttgccatgaggtgagcgacacaataccaaccatcgcacaccagcattccaaccggctcgcgacctgccgg
tgaagtaaaagcgacttccgatatgtcccaaatttcccgatacgtcgaggccgccgagcgtgacaacacgcgtcgaag
ctatgccgcagccattcgccatttcgaggtggagtggaaaggcttgctgccaacgaccgctgatgcaacctccgtta
cctggctgaccacgcggccacgctggcgatcagcaccctccgtcagcggctcgccgcgctctcgcgctggcacatcga
ccatggttttgcagaccgaccaaggcaccttggtgcgccaggttctcaaaggcattcgctccattcactcggttgc
agaaaagcgggcacgccccttgaaatcgatgtcgtccagcagatcgatcaatggctgggggtggccatcggcaacgc
agaacgcagcgatgaccgattggcgctgcttcgccacacccgcaaccgcagtttgctgctgctggtttctggcgggg
atttcgatcggacgagttggtcaacctgcgggtggagaacgtggaagtctcgcctggcgaagggctgtcgtgctacct
gagccgcagcaagggcgatcggcagatgctggccgcgtatacaaatgtccggcgctgtcccgcctgtgtcctgtgac
ggctttcacggcatgggtcagtctggtcggcctgacccaaggccggtgtttcgcaagatcgaccgctggggcgaat
cggtcaagaaggctgcatgccaacagcctgatcccattgttgcgcagccttttggctgaggccggggtccccgcttc
cgaggcatacagcagccactccctgcgtcgcggatttgccggttgggctcgcgccagcggttgggacatcaaggaact
catggagtacgtgggctggaaggatgtcaaatcggccatgcgttatctggatgcctccggcagcgcacttcaggcccg
gtttgaggcgggtctcgcaacactggccccagcagatcgagcggatcggtcaccaccgccttcgatgcacgcgccggc
cgagcaaaccaagggaacaggccagaggccccgtctgcctga
```

Delftia acidoorans phosphodiesterase pdeA

```
atgcacaagttcatccacatcacggacattcatcttgtcgagcagggtcgcgccctctacgccatgacccccggcaaa
cggttcgagcgctgcatcgacagcgtgatcgccgagcacgcggacgcagcgtcttgcgtgatcacgggcgacctcgca
catgtcgggcaccggacgcctaccgccagctgtcggagcaatgcgcgcggttgccaatgccggttcatctgattctc
ggcaaccacgacagccggaccaacttccgcgagcgcttccacaggtgccggtggacagcaatggttcgtccagtac
gagcaggccatcgggaggttcaggggtctgtttctggataccaacgaaccggaacgcattgcgcgtcttctgcgag
caacgggcaaactggctttcccagcgcttgcggaggatgattcaccggtgctcctgttcatgcatcatccggcattc
caccttggcatccccggtcatggatcgaatcggattggtcgacaacgaatggttgctgacggcgttgaagggccacgag
cacgcgtcaagcacttgttcttcggccacattcatcgcccatctcgggcagctggcgcggcatcccgttctcgaca
ttgcgcggaaccaaccaccaggtggcgctgcaccttcgggaatcggaagacatcccggaagcttcgagccaccacag
tacgccgtcgtcctgctcgacgacgattcggtgatcgtgcacctgcatgactttctcgatcgcagcgagagattctgg
ctaggcgcgtag
```

Enterobacter aerogenes updABDE gpdQ

```
atgaataagcgctggctcccctggctgatactgtcgccttccctgttgttttactgctgtttacctggtttccgctt
ggccgttcggtctatgacagcctgtttgataccggcatggccagcgacggcgcacagtacgtcgggctggataacttc
gccgcctgtttgccgacgcgttttctggcaatcgctggtcaataatctgctctatatcctgctgacggtggtgccc
ggcgtgacgctcgctctgctgctggcggtggcgctgagcgagaatcaccgcgtcaaccgctggctgcgcaccgccttt
ttcttcccgatgattatccgatggttagcgccgccgcgtgtggctgtttattttatgccggcctcggcctgctc
gatcactatctggcgaagctatttggccctcagaacaacaactggctggggcgcagcaacagcgcgctgctggcgctg
gcgctgattggcgtgtggaaattcgctggctactacatgctgttttcctcgccgggctgcagagcattccggcctca
acgcgggaagcggcgctgatggaagggccagccgcacccaggtgtttttaaggtcacgctgccgctgctgcgcccg
acgctgagctttgttatcaccaccgcgctgatttactccattacccagattgatcacgtcgcggtgatgacgcgcggc
gggccggataacgccacgaccgtgctgctctattacatccagaatctcgcctgggataccacgacctcggcaaagcc
tccgccgccaccttcctgacgctggccggctgtttgccttctcgctgattaacctgaaattgctggaaaaggagcc
cactatgagcgctgaaatctcgccgctgatggtccgctcgccgccgctgcgcgtccgtgtggttgcgcctgcgtcg
ctcacagccccttaccctgacggtaatcatgtgctgcctggcgctgctatgggtgagcccgtttatctggatgctggc
gacctcgttcagcgccaccaccttcggcgaagatatggcctcattgctgccgcgcctgccgctgaccctcgataactt
```

Figure 1 (continued)

```
ccgcgacgcctgggacagcgccgactggctgagcctgtacgccaacaccttatctttaccttcggcactttcttcgt
gcagctactcaccatcaccacgccggctacgtcttcgcctgccacgaatttcgcggcaagaaaatgctatttctgct
gtttctcgtccagctgatgatcatgccggtggtgatgatggtgccgaacatgctgaccctgaaaaccttcggcctgct
caacactctgaccggcgtgatgatgccttactttacctcggcgttcggcgtgtttctgatgcgccaggcgttcctcgc
catcccgaaagagctggaagaggcggcgctgatggaggatgccgctggtggcaggtgctattccggtactgctgcc
gatgtcctggccgtcggtgctggccttcgccaccgtcagcattacctaccactggaacgagtacctgtggccgctgat
gatgctcaacgatcccgataagcaggtgctgacggtcgggctggtctctttcgccatgggcgctgaatccggcggcca
gtggggcaccatcggcgccgggacgctgatggtctgcctgccgctgatgctggcgttcatccttttccagaaacagtt
cctgcgaagcttcggcttctccgggatcaaataaggagttattcatgctgttagcgcacatttccgatacccatttcc
gcagccgcggcgagaagctgtacggctttatcgacgtcaacgccgccaatgctgatgtggtttctcaacttaacgcgc
tgcgcgaacgcccggatgcggtggtggtgagcggcgatatcgtcaactgcggccgtccggaggagtatcaggtcgcc
gccagatcctcggcagcctgaactatccgctgtatctcatcccccggcaaccacgatgataaagcgctgtttctggagt
acctgcagccgctgtgtccacagctcggtagcgatgccaataatatgcgctgtgcggttgacgacttcgctaccgcc
tgctgtttatcgactccagccgcgccggcacttcaaaaggctggctgaccgacgagaccattagctggctggaagcgc
agctgttcgagggcggcgacaaaccggcaacgatctttatgcaccaccgcgccgtgccgctggcaatgcgcagatgg
accgattgcctgcgaaaacggccaccgtctgctggcgttggtagagcgtttcccgtcgctgacgcgcatcttttgcg
gtcataaccatagcctgaccatgacccagtatcgccaggcgctgatctccaccctccccggcaccgtccatcaggtgc
cttactgccacgaagacactcgcccgtattacgatctctcgccggcttcgtgcctgatgcaccgccaggtcggcgagc
aatgggtgagctaccagcactcgctggcccactacgccgggccgtggctgtacgacgaaaacatcagttgtccaacgg
aagagcgctaaccgccatgctcagtctgcaaaacatcagtaaacatttcgacggtaaaccggcgctcagcgcgctgtc
gcttgatatccacgaaggtgaatttgtggtgctggtcgcccgtcggcgctgcggtaaaagcaccctactgcgcctgct
gccgggttggatcaggtcagcgaaggcgaaatctggctgcatgatgagaacatcaccgacaccacgccgcgcgaacg
caattttgcgatgatctccagaactatgcgctgtttccacatctctctgtgcgcgacaacatcaccttcggcatgaa
ggtacgcaaggaagagaaaagcggctggcagccgcgggtagataaagtggcgcagatgctgcagctggaggcgctgct
cgatcgcaaaccggcgaagctctccggcggccaacggcagcgggtagcgatggcgcgggcgatcgtgcgtaatccgcg
gctgttcttaatggatgaacgctgtccaacctcgacgctcgtctgcgcagcgaagtccgcgacagcattatggacct
ccaccagcagttaaaaaccagtaccgtctacgtcacccacgatcaaaccgaagccatgtcgatggccgaccgcatcgt
ggtgatgaacggcggccacgtgcagcaagtggggcggccagagtatctgtatgccaacccggccaatctgttcgtggc
cagatttatcggttcaccggcaatgaatctgctatcgctccctgcgttgacggcaacgttcagcttggcgaacaacg
ccatccgctaccgccgcgccatcgcagccagaccgtgtctggctgggcattcgccggaacatattaccgaccgcgt
ggagcacggccatctgcgcctgccgggcaccgtcctgcaacgagaactgatgggagccgattatctgctccacgtcag
cacccgatcggcaccctgcgctttagccgccgccaccgtggcacggtgccggaaaaggcgaatcgctgatcctcgg
cttctcgcctgccgatgtgcatctttttcatgctgagacccagcataatttactgatggagtgtaatcatgtttaacc
ccctcaccgccctgacggttgggctcagcctcgccctgagcggcacggcgctggcgaaagagaaaatagacttcatgt
tcccggccccggtagacggcaagctgacgatggagatgacacgcgtcattaaagcctttaacgagtcgcagcaggatg
tcgaagtgcgcggcatcttcaccggcaactatgacaccaccaagatcaaagccgaatccgcgcagaaggccgggcaac
cccggcgctggtgatcatgtccgccaacttcaccaccgatctggcgctgaaggatgagatcctgccgatggatgagc
tgtttaaatatggcgatcaaaagccggcgattttctgcaaaaggaattctggccgcgatgcataagaacgccagg
tgatgggcaccacctatgcgatcccgttccataactcgacaccgatcctctactacaacaagacgctgttagatcgag
ctgggatcgcgcaaccaccgcagacctgggccgagctgctggccgatgccaaaaagctgaccgacgagagcaaaggcc
agtggggatcatgctgccgtcgaccaacgacgactacggcggctggatcttctcggcgctggtgcgcgccaacggcg
gtaaatatttcaatgaagactatccgggtgaggtttattacaactcgccgaccgctatcggcgctctgcgcttctggc
aggatctgatctacaaagacaaagtgatgccttccggggtactgaattcgaagcagatcagcgcttcattcttctccg
gcaaacttggcatggcgatgctcagcaccggcgcactggctttatgcgcgagaacagtaaagattttgaactcggtg
tcgccatgctaccagccaaagagcagcgcgcggtgccaattggcggcgccagcctggtgagctttaaaggcatcaacg
acgcgcagaagaaagcggcctaccagttcctgacttatctggtgagcccgcaggtaaacggcgcgtggagccgcttta
ccggctacttctcgccgcgtaaggcttcttacgatactccggagatgaaagcttatctgcagcaggatccacgagcag
cgatcgcccttgaacagctgaagtacgcgcatccgtggtactccacctgggagaccgtcgccgtgcgtaaggcgatgg
agaaccagctggcggcagtggtcaacgatgccaaagtaacgccggaagccgcggtacaggcagcgcagaaggaagctg
acgcgctaatgaaaccttatgttgataagactgcgctgggagaagtgcagtag
```

Figure 1 (continued)

Flavobacterium opdA without periplasmic leader sequence

```
atgtcgatcggcacaggcgatcggatcaataccgtgcgcggtcctatcacaatctctgaagcgggtttcacactgact
cacgagcacatctgcggcagctcggcaggattcttgcgtgcttggccagagttcttcggtagccgcaaagctctagcg
gaaaaggctgtgagaggattgcgccgcgccagagcggctggcgtgcgaacgattgtcgatgtgtcgactttcgatatc
ggtcgcgacgtcagtttattggccgaggtttcgcgggctgccgacgttcatatcgtggcggcgaccggcttgtggttc
gacccgccactttcgatgcgattgaggagtgtagaggaactcacacagttcttcctgcgtgagattcaatatggcatc
gaagacaccggaattagggcgggcattatcaaggtcgcgaccacaggcaaggcgaccccctttcaggagttagtgtta
aaggcggccgccgggccagcttggccaccggtgttccggtaaccactcacacggcagcaagtcagcgcgatggtgag
cagcaggccgccatttttgagtccgaaggcttgagcccctcacgggtttgtattggtcacagcgatgatactgacgat
ttgagctatctcaccgccctcgctgcgcgcggatacctcatcggtctagaccacatcccgcacagtgcgattggtcta
gaagataatgcgagtgcatcagccctcctgggcatccgttcgtggcaaacacgggctctcttgatcaaggcgctcatc
gaccaaggctacatgaaacaaatcctcgtttcgaatgactggctgttcgggttttcgagctatgtcaccaacatcatg
gacgtgatggatcgcgtgaacccgacgggatggccttcattccactgagagtgatcccattcctacgagagaagggc
gtcccacaggaaacgctggcaggcatcactgtgactaacccggcgcggttcttgtcaccgaccttgcgggcgtcatga
```

Pseudomonas aeruginosa PAO1 phoA

```
atgacccaggttatccctcgccctctctcttgccgtctccatggccgtgctcggcagcgccttgccggccaggcg
cgccaggacgatccgtcactgttcaaccgccaggcccgtggcgaactcagcgagtacggcggcgcacggcgcgtcgag
caggacctgacccaggccctgaagcagtcgctgtcgaagaagaaggcgaagaacgtgatcctgctgatcggcgacggc
atgggcgactccgagatcaccgtggcgcgcaactacgcgcgcggcgcgggcggctacttcaagggtatcgatgcgctg
ccgctgaccggtcagtacacccactactccctgcacaaggacagcggcctgccggactacgtgaccgattccgccgcc
tccgccaccgcctggtccaccggggtcaagtcgtacaacggcgcgatggcgtggatatccacgaacagccgcaccgc
aacctgctggagctggccaagctcaacggcaaggccacggcaacgtctccacgccgagctgcaggacgccaccccc
gccgccctgctcgccacgtcaccgctcgcaagtgctacggtcccgaggccaccagcaagcagtgcccgagcaatgcc
ctggagaacggcggcgccggctcgatcaccgagcagtggctgaagacccgccctgacgtggttctcggcggcggcgcc
gcgaccttcgcggaaaccgccaaggctggccgctatgccggcaagaccctccgcgccaggccgaagcccgcggctac
cggatcgtcgagaacctcgacgagctgaaagccgtgcgccgcgccaaccagaagcagccgctgatcggcctgttcgcg
ccgggcaacatgccagtgcgctggctcggtccgaccgccacctaccacggcaacctgaaccagccggcggtgagctgc
gaggcgaacccgaagcgcaccgccgacatcccgaccctggcgcaaatgaccagcaaggccatcgagctgctgaaggac
aatccgaacggcttcttcctgcaggtcgagggcgcgtccatcgacaagcaggaccatgccgcgaatccgtgggccag
atcggcgagaccgtcgacctcgacgaagccgtgcagaaggccctggcctttgccaaggccgatggcgagaccctggtg
atcgtcaccgccgaccacgccactccagccagatcatcccgccggaaaccgccgcgcggggctgacccaactgctc
acgaccaaggacggcgcgccgctggcgatcagctacggcaactccgaggaaagctcccaggagcacaccggcacccag
ttgcgcatcgccgcctacggcccgcaggccgccaatgtcaccggcctgaccgaccagaccgacctgttcttcaccatc
cgtcgcgcactgaacctgcgcgactga
```

Pseudomonas monteilii C11 hocA

```
atgaaagaactaaaaacctggaagtgggaagataaagagagaacaatgctgagaaaaatctctgttggagatatattt
tgcctcaccaaagacaacagcaactatcatttcggtaaaatcttgtcaaaaatgattgtaggccacgcagtcgaaata
ttaaatatcactaaagacagccatcaatcacccagcaagaacttgaacaatcagccttagcaggcgaccgctactg
ctagatagttacgctttattcgacaagaaaattgacaaaggtggcgactggagaataattggccatcaagagatatca
tcaccagaatcctatcgaaactactacttcctgttcctgtacggaacacacaacaactggaaaaaagtcaacatcctc
aatgaggaagttgaaatatcaaatacagagccctaacgctccccttgcttaaagctcttagcaatcacagattctgg
gaaacaataaacgaagaactaaagctaaactggtaa
```

Figure 1 (continued)

Rhodococcus dszD ttgtctgacaagccgaatgccgtttccagccacaccaccccgacgtccccgaagtagcggcgacgcccgagttgtcc
acggcatctgcgccggtgactaccgcgctgcgcttcgccgccacccgccggtgtcaccgtcgtgaccctcgattcg
ggtaccggcccggtgggtttcaccgccacctcgttctcgtccgtctccctcgagccgccgctcgtctcgttcaacatc
gcggagacgtcgtcgagcatcaatgcactcaaggcagccgagtccttggtgatccaccttctcggcgaacatcagcag
catctggcccagcgctttgcgcgtagtgccgatcagcgttttgcagacgagtcactgtgggcagtgctcgacaccggg
gaaccggtgctgcacggcaccccagctggatgcgcgtcaaggtcgaccagctgatccctgtcggcgaccacacgctg
gtcatcggactcgtcacgcgggttcacgccgaagaagacgacgaatccgctgccgcgccgctgctctaccacgagggc
aagtactaccgcccgactccgttaggtcaatag Rhodococcus dszABC atgactcaacaacgacaaatgcatctggccggtttcttctcggccggcaatgtgactcatgcacatggggcgtggcgg
cacacggacgcgtcgaatgacttctgtcggggaagtactaccaacacatcgcccgtactctggagcgcggcaagttc
gatctgttgtttctgcctgacggggttggccgtcgaggacagctacggggacaacctggacaccggtgtcggcctgggc
gggcagggtgcagtcgccttggagccggccagtgtggtcgcaaccatggccgcggtgaccgagcacctgggtcttggg
gcaaccattcggcgacctactatccccgtatcacgttgctcggggtgttcgcgacgctcgatcagttgtcaggggggt
cgggtgtcctggaacgtcgtcacctcgctcaacgacgctgaagcgcgcaacttcggcattaatcagcatctggaacac
gacgcccgctatgaccgcgccgatgagttcttggaagcggtcaagaaactctggaacagctgggacgaggacgccctc
gtgctggacaaggcggccggcgtgttcgccgatcccgcgaaggtgcactacgtcgatcaccacggggagtggctgaat
gtgcgcggacctctgcaggtaccgcgttcacctcagggtgagccggtgatcctgcaggccggcctgtcgccccggggt
cggcgcttcgccgggaagtgggccgaggccgtcttcagtcttgcacccaacctcgaggtgatgcaggccacctaccag
ggcatcaaagccgaggtcgacgctgcggggcgcgatcccgatcagacgaaaatcttcaccgccgtgatgccggtactc
ggcgaaagccaggcggtggcacaggaacgactggaatatctcaacagtctggtccatccggaagtgggactgtcgacg
ctatccagtcacaccggcatcaacctggcggcgtacccctctcgacactccgatcaaggacatcctgcgggatctgcag
gatcggaatgtcccgacgcaactgcacatgttcgccgccgcaacgcacagcgaagagctcacgctggcggaaatgggt
cggcgctatggaaccaacgtggggttcgttcctcagtggccggtaccggggagcagatcgctgacgagctgatccgc
cacttcgagggcggcgccgcggatggtttcatcatctctccggccttcctgccgggctcctacgacgagttcgtcgac
caggtggttccggttctgcaggatcgcggctacttccgcaccgagtaccagggcaacactctgcgcgaccacttgggt
ctgcgcgtaccacaactgcaaggacaaccttcatgacaagccgcgtcgacccccgcaaacccggttcagaactcgatt
ccgccatccgcgacacactgacctacagcaactgcccggtacccaacgctctgctcacggcatcggaatcgggcttcc
tcgacgccgccggcatcgaactcgacgtcctcagcggccagcagggcacggttcatttcacctacgaccagcctgcct
acacccgttttgggggtgagatcccgccactgctcagcgaggggttgcgggcacctgggcgcacgcgtctactcggca
tcaccccgctcttggggcgccagggcttctttgtccgcgacgacagcccgatcacagcggccgccgaccttgccggac
gtcgaatcggcgtctcggcctcggcaattcgcatcctgcgcggccagctgggcgactacctcgagttggatccctggc
ggcaaacgctggtagcgctgggctcgtgggaggcgcgcgccttgttgcacaccttgagcacggtgaactgggtgtgg
acgacgtcgagctggtgccgatcagcagtcctggtgtcgatgttccgctgagcagctcgaagaatcggcgaccgtca
agggtgcggacctctttcccgatgtcgcccgcggtcaggccgcggtgttggccagcggagacgttgacgccctgtaca
gttggctgccctgggccggggagttgcaagccaccggggccgcccagtggtggatctcggcctcgatgagcgcaatg
cctacgccagtgtgtggacggtcagcagcgggctggttcgccagcgacctggccttgttcaacgactggtcgacgcgg
ccgtcgacgccgggctgtgggcacgcgatcattccgacgcggtgaccagcctgcacgccgcgaacctgggcgtatcga
ccggagcagtaggccagggcttcggcgccgacttccagcagcgtctggttccacgcctggatcacgacgccctcgccc
tcctggagcgcacacagcaattcctgctcaccaacaacttgctgcaggaacccgtcgccctcgatcagtgggcggctc
cggaatttctgaacaacagcctcaatcgccaccgataggaacatccgcatgacactgtcacctgaaaagcagcacgtt
cgaccacgcgacgccgacaacgatcccgtcgcggttgcccgtgggctagccgaaaagtggcgagccaccgccgtc
gagcgtgatcgccgggggttcggcaacagccgagcgcgaagacctgcgcgcgagcgcgctgctgtcgctcctcgtc
ccgcgcgaataccggcggctggggcgcagactggcccaccgccatcgaggtcgtccgcgaaatcgcggcagccgatgga
tctttgggacacctgttcggataccacctcaccaacgcccgatgatcgaactgatcggctcgcaggaacaagaagaa
cacctgtacacccagatcgcgcagaacaactggtggacccgaaatgcctccagcgagaacaacagccacgtgctggac
tggaaggtcagcgccaccccgaccgaagacggcggctacgtgctcaatggcacgaagcacttctgcagcggcgccaag
gggtcggacctgctgttcgtgttcggcgtcgtccaggatgattctccgcagcagggtgcgatcattgctgccgctatc
ccgacatcgcggctggcgttacgcccaacgacgactggccgccatcggcatcggcagaccgacagcggttccacg

Figure 1 (continued)

```
gacttccacaacgtcaaggtcgagcctgacgaagtgctgggcgcgcccaacgccttcgttctcgccttcatacaatcc
gagcgcggcagcctcttccggcccatagcgcaattgatcttcgccaacgtctatctggggatcgcgcacggcgcactc
gatgccgccaggagtacaccgtaccaggcgaggcctggacaccggccggtattcaacaggcaaccgaggatccc
tacaccatccgctcctacggtgagttcaccatcgcattgcagggagctgacgccgccgccgtgaagcggcccacctg
ctgcagacggtgtgggacaagggcgacgcgctcaccccgaggaccgcggcgaactgatggtgaaggtctcgggagtc
aaagcgttggccaccaacgccgcctcaacatcagcagcggcgtcttcgaggtgatcggcgcgcggaacacatccc
aggtacggtttcgaccgcttctggcgcaacgtgcgcacccactccctgcacgacccggtgtcctacaagatcgccgac
gtcggcaagcacaccttgaacggtcaatacccgattccggcttcacctcctga
```

Figure 2

| Organism | Potential Applications |
|---|---|
| *Escherichia coli* | Biotech |
| *Saccharomyces cerevisiae* | Ethanol, food, biotech |
| *Yarrowia lipolytica* | Citrate, lipase, lipids, polyols |
| *Kluyveromyces marxianus* | biotech |
| *Bacillus subtilis* | industrial enzymes |
| *Hansenula polymorpha* | enzymes, SCP |
| *Aspegillus niger* | Citrate, amylase, oxalate |
| *Corynebacterium glutamicum* | Amino acids, nucleotides |
| *Synechococcus elongatus* | Biofuels, lipids |
| *Chlamydomonas reinhardtii* | Biofuels, model organism |

Figure 3

| Organism | Potential Applications |
|---|---|
| Mammalian/CHO | pharma |
| Kluyveromyes lactis | lactic acid |
| Xanthomonas campestris | Xanthan gum, plant pathogen |
| Pichia pastoris | enzymes |
| Candida utilis | animal feed |
| Aspergillus oryzae | enzymes, malic acid |
| Bacillus stearothermophilus | industrial enzymes |
| Bacillus licheniforms | industrial enzymes |
| Lactococcus lactis | Dairy, food |
| Streptococcus lactis | Dairy, food |
| Trichoderma reesei | cellulases, xylanases |
| Clostridium acetobutylicum | butanol, 1,3 PD, solvents and acids |
| Clostridium thermocellum | ethanol, biofuels |
| Streptomyces | antibiotics, antifungals, protein expression |
| Acetobacter | acetic acid, speciality sugars |
| Micrococcus lysodeikticus | catalyase, dairy |
| Pichia guilliermondii | citric acid |
| Arxula adeninivorans | enzymes, possibly biofuels |
| Acinetobacter calcoaceticus | |
| Paracoccus denitrificans | |
| Pseudomonas putida | chemicals, solvents |
| Bacillus methanolicus | methanol utilization |
| Alcaligenes eutropha | PHA/PHB, chemicals |
| Thermoanaerobacter/Thermoanaerobacterium spp. | biofuels |
| Pichia stipitis | |
| Rhodosporidium spp | |
| Rhodotorula spp. | |
| Schizosaccharomyces pombe | |
| Penicillium chrysogenum | |
| Aspergillus terreus | itaconic acid |
| Aspergillus nidulans | |
| Rhizopus spp. | |
| Nannochloropsis spp. | |
| Tetraselmis spp. | |
| Pavlova spp. | |
| Isochrysis spp. | |
| Aurantiochytrium spp | |

Figure 4

| Hypophosphorous acid | $H_3PO_2$ |
|---|---|
| Phosphorous acid (phosphite) | $H_3PO_3$ |
| Diethyl phosphate | $C_4H_{11}O_4P$ |
| Triethyl phosphate | $C_6H_{15}O_4P$ |
| Trimethyl phosphate | $(CH_3)_3PO_4$ |
| Dimethyl phosphate (DMP) | $C_2H_7O_4P$ |
| Diethyl phosphite | $C_4H_{11}O_3P$ |
| Triethyl phosphite | $C_6H_{15}O_3P$ |
| Trimethyl phosphite | $C_3H_9O_3P$ |
| Dimethyl phosphite | $C_2H_7O_3P$ |
| Glyphosate (round-up) | $C_3H_8NO_5P$ |
| O,O,O-Triethyl Phosphorothioate | $C_6H_{15}O_3PS$ |
| Etidronic acid | $C_2H_8O_7P_2$ |
| Disodium methylene diphosphonate | $CH_4Na_2O_6P_2$ |
| Medronic acid | $CH_6O_6P_2$ |
| Clodronic acid | $CH_4Cl_2O_6P_2$ |
| Tiludronic acid | $C_7H_9ClO_6P_2S$ |
| Zoledronic acid | $C_5H_{10}N_2O_7P_2$ |
| Oxidronic Acid | $CH_6O_7P_2$ |

Figure 5

| Dimethylsulfoxide | $C_2H_6OS$ |
|---|---|
| Dibenzothiophene | $C_{12}H_8S$ |
| Ethanethiol | $C_2H_6S$ |
| Dimercaptosuccinic acid | $C_4H_6O_4S_2$ |
| Thioacetic acid | $C_2H_4OS$ |
| tert-Butylthiol | $C_4H_{10}S$ |
| Thiourea | $CH_4N_2S$ |
| Sodium thiocyanate | NaSCN |
| Thioacetamide | $C_2H_5NS$ |
| Isothiazole | $C_3H_3NS$ |
| Benzisothiazolinone | $C_7H_5NOS$ |
| Isothiazolinone | $C_3H_3NOS$ |
| Methanesulfonic acid | $CH_4O_3S$ |
| Thioglycerol | $C_3H_8O_2S$ |
| Potassium metabisulfite | $K_2O_5S_2$ |
| Acesulfame potassium | $C_4H_4KNO_4S$ |
| Benzenesulfonic acid | $C_6H_5SO_3H$ |
| Sodium cyclamate | $C_6H_{12}NNaO_3S$ |
| Saccharin | $C_7H_5NO_3S$ |
| Dioctyl sodium sulfosuccinate | $C_{20}H_{37}NaO_7S$ |
| 2,4-Dithiapentane | $C_3H_8S_2$ |
| Methylisothiazolinone | $C_4H_5NOS$ |
| Methylchloroisothiazolinone | $C_4H_4ClNOS$ |
| Sulfolane | $C_4H_8O_2S$ |

Figure 9

```
LOCUS       pNC273                  8184 bp ds-DNA     circular     22-NOV-2013
DEFINITION  .
ACCESSION
VERSION
SOURCE      .
  ORGANISM  .
COMMENT
COMMENT
COMMENT     ApEinfo:methylated:1
FEATURES             Location/Qualifiers
     misc_feature    1448..1471
                     /label=2u ori
                     /ApEinfo_fwdcolor=#8080ff
                     /ApEinfo_revcolor=#8080ff
                     /ApEinfo_graphicformat=arrow_data {{0 1 2 0 0 -1} {} 0}
                     width 5 offset 0
     misc_feature    1..1447
                     /label=2u ori(1)
                     /ApEinfo_label=2u ori
                     /ApEinfo_fwdcolor=#8080ff
                     /ApEinfo_revcolor=#8080ff
                     /ApEinfo_graphicformat=arrow_data {{0 1 2 0 0 -1} {} 0}
                     width 5 offset 0
     rep_origin      complement(5412..6000)
                     /note="pMB1 origin of replication (counter-clockwise)
                     (RNAII -35 to RNA/DNA switch point)"
                     /label=pMB1 ori
                     /ApEinfo_fwdcolor=#ff0000
                     /ApEinfo_revcolor=#ff0000
                     /ApEinfo_graphicformat=arrow_data {{0 1 2 0 0 -1} {} 0}
                     width 5 offset 0
     misc_feature    3554..4084
                     /label=YlTEFlp(PR3)
                     /ApEinfo_fwdcolor=cyan
                     /ApEinfo_revcolor=green
                     /ApEinfo_graphicformat=arrow_data {{0 1 2 0 0 -1} {} 0}
                     width 5 offset 0
     misc_feature    5096..5395
                     /label=YlCYC1t(TER1)
                     /ApEinfo_fwdcolor=#00ffff
                     /ApEinfo_revcolor=green
                     /ApEinfo_graphicformat=arrow_data {{0 1 2 0 0 -1} {} 0}
                     width 5 offset 0
     gene            4085..5095
                     /gene="ptxABCDE operon"
                     /note="phosphite oxidation operon"
                     /label=ptxABCDE operon
                     /ApEinfo_fwdcolor=pink
                     /ApEinfo_revcolor=pink
                     /ApEinfo_graphicformat=arrow_data {{0 1 2 0 0 -1} {} 0}
                     width 5 offset 0
     misc_feature    1488..2309
                     /label=ScFBA1p
                     /ApEinfo_fwdcolor=#c70cdc
                     /ApEinfo_revcolor=#c70cdc
                     /ApEinfo_graphicformat=arrow_data {{0 1 2 0 0 -1} {} 0}
                     width 5 offset 0
```

Figure 9 (continued)

```
     misc_feature    complement(6171..7121)
                     /label=AmpR
                     /ApEinfo_fwdcolor=#ff00ff
                     /ApEinfo_revcolor=#ff00ff
                     /ApEinfo_graphicformat=arrow_data {{0 1 2 0 0 -1} {} 0}
                     width 5 offset 0
     misc_feature    complement(7138..8175)
                     /label=Sc URA3
                     /ApEinfo_fwdcolor=cyan
                     /ApEinfo_revcolor=#00ff00
                     /ApEinfo_graphicformat=arrow_data {{0 1 2 0 0 -1} {} 0}
                     width 5 offset 0
     misc_feature    3349..3553
                     /label=ScFBAlt
                     /ApEinfo_fwdcolor=#eb74f8
                     /ApEinfo_revcolor=#eb74f8
                     /ApEinfo_graphicformat=arrow_data {{0 1 2 0 0 -1} {} 0}
                     width 5 offset 0
     CDS             2310..3335
                     /label=hygR (NG4)
                     /ApEinfo_fwdcolor=#00d700
                     /ApEinfo_revcolor=#00a200
                     /ApEinfo_graphicformat=arrow_data {{0 1 2 0 0 -1} {} 0}
                     width 5 offset 0
     misc_feature    1480..1487
                     /label=PmeI
                     /ApEinfo_fwdcolor=#ff8040
                     /ApEinfo_revcolor=green
                     /ApEinfo_graphicformat=arrow_data {{0 1 2 0 0 -1} {} 0}
                     width 5 offset 0
     misc_feature    5396..5403
                     /label=PmeI(1)
                     /ApEinfo_label=PmeI
                     /ApEinfo_fwdcolor=#ff8040
                     /ApEinfo_revcolor=green
                     /ApEinfo_graphicformat=arrow_data {{0 1 2 0 0 -1} {} 0}
                     width 5 offset 0
     gene            5089..5095
                     /gene="ptxE"
                     /label=ptxE
                     /ApEinfo_fwdcolor=pink
                     /ApEinfo_revcolor=pink
                     /ApEinfo_graphicformat=arrow_data {{0 1 2 0 0 -1} {} 0}
                     width 5 offset 0
     misc_feature    3341..3348
                     /label=AscI
                     /ApEinfo_fwdcolor=#009d9d
                     /ApEinfo_revcolor=#00b9b9
                     /ApEinfo_graphicformat=arrow_data {{0 1 2 0 0 -1} {} 0}
                     width 5 offset 0
     CDS             5089..5095
                     /gene="ptxE"
                     /note="putative transcriptional regulator of ptx operon;
                     similar to lysR family of transcriptional regulators"
                     /codon_start=1
                     /transl_table=11
                     /product="PtxE"
                     /protein_id="AAC71710.1"
```

Figure 9 (continued)

```
                    /db_xref="GI:3127081"
                    /translation="MLNPVWLKSLVAIVQTGSFQSAARALGLAQPTVSQHLQKLEEQV
                    GVTLVQRSRSGCQPTTRALAFMPHATALLDMHARALEALHGNRERVGASSNIGTYLLQ
                    PFVRNYLTTANERGEVDLRIAANPDVADQLLAGQLDAAIMEWWLPHPDFEYRLWRVEP
                    LVLIVSPDHALAEAGCIERDRLVDLPMLGGEPGSGT"
                    /label=PtxE
                    /ApEinfo_fwdcolor=pink
                    /ApEinfo_revcolor=pink
                    /ApEinfo_graphicformat=arrow_data {{0 1 2 0 0 -1} {} 0}
                    width 5 offset 0
    misc_feature    5404..5411
                    /label=AscI(1)
                    /ApEinfo_label=AscI
                    /ApEinfo_fwdcolor=#007d7d
                    /ApEinfo_revcolor=green
                    /ApEinfo_graphicformat=arrow_data {{0 1 2 0 0 -1} {} 0}
                    width 5 offset 0
    gene            4085..5095
                    /gene="ptxD"
                    /label=ptxD
                    /ApEinfo_fwdcolor=#00e800
                    /ApEinfo_revcolor=#00e800
                    /ApEinfo_graphicformat=arrow_data {{0 1 2 0 0 -1} {} 0}
                    width 5 offset 0
    misc_feature    1472..1479
                    /label=PacI
                    /ApEinfo_fwdcolor=#ffff00
                    /ApEinfo_revcolor=green
                    /ApEinfo_graphicformat=arrow_data {{0 1 2 0 0 -1} {} 0}
                    width 5 offset 0
ORIGIN
        1 TTATCGATGA TAAGCTGTCA AAGATGAGAA TTAATTCCAC GGACTATAGA CTATACTAGA
       61 TACTCCGTCT ACTGTACGAT ACACTTCCGC TCAGGTCCTT GTCCTTTAAC GAGGCCTTAC
      121 CACTCTTTTG TTACTCTATT GATCCAGCTC AGCAAAGGCA GTGTGATCTA AGATTCTATC
      181 TTCGCGATGT AGTAAAACTA GCTAGACCGA GAAAGAGACT AGAAATGCAA AAGGCACTTC
      241 TACAATGGCT GCCATCATTA TTATCCGATG TGACGCTGCA GCTTCTCAAT GATATTCGAA
      301 TACGCTTTGA GGAGATACAG CCTAATATCC GACAAACTGT TTTACAGATT TACGATCGTA
      361 CTTGTTACCC ATCATTGAAT TTGAACATC CGAACCTGGG AGTTTCCCT GAAACAGATA
      421 GTATATTTGA ACCTGTATAA TAATATATAG TCTAGCGCTT TACGGAAGAC AATGTATGTA
      481 TTTCGGTTCC TGGAGAAACT ATTGCATCTA TTGCATAGGT AATCTTGCAC GTCGCATCCC
      541 CGGTTCATTT TCTGCGTTTC CATCTTGCAC TTCAATAGCA TATCTTTGTT AACGAAGCAT
      601 CTGTGCTTCA TTTGTAGAA CAAAATGCA ACGCGAGAGC GCTAATTTTT CAAACAAAGA
      661 ATCTGAGCTG CATTTTTACA GAACAGAAAT GCAACGCGAA AGCGCTATTT TACCAACGAA
      721 GAATCTGTGC TTCATTTTTG TAAAACAAAA ATGCAACGCG ACGAGAGCGC TAATTTTTCA
      781 AACAAAGAAT CTGAGCTGCA TTTTTACAGA ACAGAAATGC AACGCGAGAG CGCTATTTTA
      841 CCAACAAAGA ATCTATACTT CTTTTTTGTT CTACAAAAAT GCATCCCGAG AGCGCTATTT
      901 TTCTAACAAA GCATCTTAGA TTACTTTTTT TCTCCTTTGT GCGCTCTATA ATGCAGTCTC
      961 TTGATAACTT TTTGCACTGT AGGTCCGTTA AGGTTAGAAG AAGGCTACTT TGGTGTCTAT
     1021 TTTCTCTTCC ATAAAAAAG CCTGACTCCA CTTCCCGCGT TTACTGATTA CTAGCGAAGC
     1081 TGCGGGTGCA TTTTTTCAAG ATAAAGGCAT CCCCGATTAT ATTCTATACC GATGTGGATT
     1141 GCGCATACTT TGTGAACAGA AAGTGATAGC GTTGATGATT CTTCATTGGT CAGAAAATTA
     1201 TGAACGGTTT CTTCTATTTT GTCTCTATAT ACTACGTATA GGAAATGTTT ACATTTTCGT
     1261 ATTGTTTTCG ATTCACTCTA TGAATAGTTC TTACTACAAT TTTTTTGTCT AAAGAGTAAT
     1321 ACTAGAGATA AACATAAAAA ATGTAGAGGT CGAGTTTAGA TGCAAGTTCA AGGAGCGAAA
     1381 GGTGGATGGG TAGGTTATAT AGGGATATAG CACAGAGATA TATAGCAAAG AGATACTTTT
     1441 GAGCAATGTT TGTGGAAGCG GTATTCGCAA Tttaattaag tttaaacGAT CCAACTGGCA
     1501 CCGCTGGCTT GAACAACAAT ACCAGCCTTC CAACTTCTGT AAATAACGGC GGTACGCCAG
     1561 TGCCACCAGT ACCGTTACCT TTCGGTATAC CTCCTTTCCC CATGTTTCCA ATGCCCTTCA
```

Figure 9 (continued)

```
1621 TGCCTCCAAC GGCTACTATC ACAAATCCTC ATCAAGCTGA CGCAAGCCCT AAGAAATGAA
1681 TAACAATACT GACAGTACTA AATAATTGCC TACTTGGCTT CACATACGTT GCATACGTCG
1741 ATATAGATAA TAATGATAAT GACAGCAGGA TTATCGTAAT ACGTAATAGT TGAAAATCTC
1801 AAAAATGTGT GGGTCATTAC GTAAATAATG ATAGGAATGG GATTCTTCTA TTTTTCCTTT
1861 TTCCATTCTA GCAGCCGTCG GGAAAACGTG GCATCCTCTC TTTCGGGCTC AATTGGAGTC
1921 ACGCTGCCGT GAGCATCCTC TCTTTCCATA TCTAACAACT GAGCACGTAA CCAATGGAAA
1981 AGCATGAGCT TAGCGTTGCT CCAAAAAAGT ATTGGATGGT TAATACCATT TGTCTGTTCT
2041 CTTCTGACTT TGACTCCTCA AAAAAAAAAA ATCTACAATC AACAGATCGC TTCAATTACG
2101 CCCTCACAAA AACTTTTTTC CTTCTTCTTC GCCCACGTTA AATTTTATCC CTCATGTTGT
2161 CTAACGGATT TCTGCACTTG ATTTATTATA AAAAGACAAA GACATAATAC TTCTCTATCA
2221 ATTTCAGTTA TTGTTCTTCC TTGCGTTATT CTTCTGTTCT TCTTTTCTT TTGTcatata
2281 taaccataac caagtaatac atattcaaaA TGAAGAAGCC CGAGCTGACC GCTACCTCTG
2341 TTGAGAAGTT CCTGATTGAG AAGTTTGATT CCGTTCCGA CCTGATGCAG CTGTCCGAGG
2401 GCGAGGAGTC TCGAGCCTTC TCCTTTGACG TGGGCGGACG AGGTTACGTT CTGCGAGTGA
2461 ACTCGTGTGC CGACGGCTTC TACAAGGATC GATACGTCTA CCGACACTTT GCTTCTGCCG
2521 CTCTGCCCAT CCCTGAGGTT CTCGACATTG GCGAGTTCTC TGAGTCCCTC ACCTACTGCA
2581 TCTCTCGACG AGCTCAGGGA GTCACCCTGC AGGACCTCCC TGAGACTGAG CTGCCTGCTG
2641 TCCTCCAGCC TGTTGCTGAG GCCATGGACG CTATCGCTGC TGCTGATCTG TCCCAGACCT
2701 CGGGTTTCGG CCCCTTTGGA CCTCAGGGAA TTGGACAGTA CACCACTTGG CGAGACTTCA
2761 TCTGTGCTAT TGCCGATCCT CACGTCTACC ATTGGCAGAC CGTTATGGAC GATACTGTGT
2821 CGGCTTCTGT CGCTCAGGCT CTGGACGAGC TGATGCTCTG GGCCGAGGAT TGCCCCGAGG
2881 TTCGACACCT GGTGCATGCT GACTTCGGTT CCAACAACGT TCTCACCGAC AACGGCCGAA
2941 TCACTGCCGT GATTGACTGG TCCGAGGCTA TGTTTGGCGA CTCGCAGTAC GAGGTGGCCA
3001 ACATCTTCTT TTGGCGACCC TGGCTGGCTT GTATGGAGCA GCAGACCCGA TACTTCGAGC
3061 GACGACATCC TGAGCTCGCT GGATCCCCTC GACTGCGAGC TTACATGCTC CGAATTGGTC
3121 TGGACCAGCT CTACCAGTCG CTGGTGGATG GCAACTTTGA CGATGCTGCC TGGGCTCAGG
3181 GACGATGTGA CGCCATCGTG CGATCTGGCG CTGGAACCGT CGGACGAACT CAGATTGCCC
3241 GACGATCCGC TGCTGTCTGG ACCGACGGAT GCGTGGAGGT CCTGGCTGAT TCGGGTAACC
3301 GACGACCCTC TACTCGACCT CGAGCTAAGG AGTAAtaaac ggcgcgccgt taattcaaat
3361 taattgatat AGTTTTTTAA TGAGTATTGA ATCTGTTTAG AAATAATGGA ATATTATTTT
3421 TATTTATTTA TTTATATTAT TGGTCGGCTC TTTTCTTCTG AAGGTCAATG ACAAAATGAT
3481 ATGAAGGAAA TAATGATTTC TAAAATTTTA CAACGTAAGA TATTTTTACA AAAGCCTAGC
3541 TCATCTTTTG TCAAGAGACC GGGTTGGCGG CGCATTTGTG TCCCAAAAAA CAGCCCCAAT
3601 TGCCCCAATT GACCCCAAAT TGACCCAGTA GCGGGCCCAA CCCCGGCGAG AGCCCCCTTC
3661 TCCCCACATA TCAAACCTCC CCCGGTTCCC ACACTTGCCG TTAAGGGCGT AGGGTACTGC
3721 AGTCTGGAAT CTACGCTTGT TCAGACTTTG TACTAGTTTC TTTGTCTGGC CATCCGGGTA
3781 ACCCATGCCG GACGCAAAAT AGACTACTGA AAATTTTTTT GCTTTGTGGT TGGGACTTTA
3841 GCCAAGGGTA TAAAAGACCA CCGTCCCCGA ATTACCTTTC CTCTTCTTTT CTCTCTCTCC
3901 TTGTCAACTC ACACCCGAAA TCGTTAAGCA TTTCCTTCTG AGTATAAGAA TCATTCAAAA
3961 TGgtgagttt cagagcagc agcaattgcc acgggctttg agcacacggc cgggtgtggt
4021 cccattccca tcgacacaag acgccacgtc atccgaccag cacttttttgc agtactaacc
4081 gcagATGCTG CCGAAACTCG TTATAACTca ccgagtacac gatgagatcc tgcaactgct
4141 ggcgccacat tgcgagctga tgaccaacca gacgacagc acgctgacgc gcgaggaaat
4201 tctgcgcgc tgtcgcgatg ctcaggcgat gatggcgttc atgccgatc gggtcgatgc
4261 agactttctt caagcctgcc ctgagctgcg tgtagtcggc tgcgcgctca agggcttcga
4321 caatttcgat gtggacgcct gtactgcccg cggggtctgg ctgaccttcg tgcctgatct
4381 gttgacggtc ccgactgccg agctggcgat cggactggcg gtggggctgg ggcggcatct
4441 gcgggcagca gatgcgttcg tccgctctgg cgagttccag ggctggcaac cacagttcta
4501 cggcacgggg ctggataacg ctacggtcgg catccttggc atgggcgcca tcggactggc
4561 catggctgat cgcttgcagg gatgggcgc gacctgcag taccacgagg cgaaggctct
4621 ggatacacaa accgagcaac ggctcggcct gcgccaggtg gcgtgcagcg aactcttcgc
4681 cagctcggac ttcatcctgc tggcgcttcc cttgaatgcc gataccagc atctggtcaa
4741 cgccgagctg cttgccctcg tacggccggg cgctctgctt gtaaacccct gtcgtggttc
4801 ggtagtggat gaagccgccg tgctcgcggc gcttgagcga ggccagctcg gcgggtatgc
4861 ggcggatgta ttcgaaatgg aagactgggc tcgcgcggac cggccgcggc tgatcgatcc
4921 tgcgctgctc gcgcatccga atacgctgtt cactccgcac atagggtcgg cagtgcgcgc
4981 ggtgcgcctg gagattgaac gttgtgcagc gcagaacatc atccaggtat tggcaggtgc
5041 gcgcccaatc aacgctgcga accgtctgcc cAAGGCCGAG CCTGCCGCAT GTTGAGCGTC
```

Figure 9 (continued)

```
5101 TACAACTGGA CCCTTAGCCT GTATATATCA ATTGATTATT TAAAGATTTG GTCGGTAGGC
5161 GGTTCGTATT GTACAATGGG ATCTGTTACT GAGGTGGATC TACCCAACTT GCGAGATTCA
5221 ATTGCGAGAT TCAATCGCGA GATTCAATTG CGAGAATCAG TTGCGAGTTG TTCTAACACT
5281 CAGCTTCTAC GAGCGCTTGT ATTAGGACGA GTGATACTCC GTGGGGCGAC GGCTTCTCTT
5341 GCGTCTTCTG TTGTATTCTT TCTTACACTA TCGTCCATCT CCAACCACCT CGTACgttta
5401 aacggcgcgc ctttccatag gctccgcccc cctgacgagc atcacaaaaa tcgacgctca
5461 agtcagaggt ggcgaaaccc gacaggacta taaagatacc aggcgtttcc ccctggaagc
5521 tccctcgtgc gctctcctgt tccgaccctg ccgcttaccg gatacctgtc cgcctttctc
5581 ccttcgggaa gcgtggcgct ttctcatagc tcacgctgta ggtatctcag ttcggtgtag
5641 gtcgttcgct ccaagctggg ctgtgtgcac gaaccccccg ttcagcccga ccgctgcgcc
5701 ttatccggta actatcgtct tgagtccaac ccggtaagac acgacttatc gccactggca
5761 gcagccactg gtaacaggat tagcagagcg aggtatgtag gcggtgctac agagttcttg
5821 aagtggtggc ctaactacgg ctacactaga agaacagtat ttggtatctg cgctctgctg
5881 aagccagtta ccttcggaaa aagagttggt agctcttgat ccggcaaaca accaccgct
5941 ggtagcggtg gttttttgt ttgcaagcag cagattacgc gcagaaaaaa aggatctcaa
6001 gaagatcctt tgatcttttc tacgggtct gacgctcagt ggaacgaaaa ctcacgttaa
6061 gggattttgg tcatgagatt atcaaaaagg atcttcacct agatcctttt aaattaaaaa
6121 tgaagtttta aatcaatcta agtatatat gagtaaactt ggtctgacag ttaccaatgc
6181 ttaatcagtg aggcacctat ctcagcgatc tgtctatttc gttcatccat agttgcctga
6241 ctccccgtcg tgtagataac tacgatacgg gagggcttac catctggccc cagtgctgca
6301 atgataccgc gagacccacg ctcaccggct ccagatttat cagcaataaa ccagccagcc
6361 ggaagggccg agcgcagaag tggtcctgca actttatccg cctccatcca gtctattaat
6421 tgttgccggg aagctagagt aagtagttcg ccagttaata gtttgcgcaa cgttgttgcc
6481 attgctacag gcatcgtggt gtcacgctcg tcgtttggta tggcttcatt cagctccggt
6541 tcccaacgat caaggcgagt tacatgatcc cccatgttgt gcaaaaaagc ggttagctcc
6601 ttcggtcctc cgatcgttgt cagaagtaag ttggccgcag tgttatcact catggttatg
6661 gcagcactgc ataattctct tactgtcatg ccatccgtaa gatgcttttc tgtgactggt
6721 gagtactcaa ccaagtcatt ctgagaatag tgtatgcggc gaccgagttg ctcttgcccg
6781 gcgtcaatac gggataatac cgcgccacat agcagaactt taaaagtgct catcattgga
6841 aaacgttctt cggggcgaaa actctcaagg atcttaccgc tgttgagatc cagttcgatg
6901 taacccactc gtgcacccaa ctgatcttca gcatctttta ctttcaccag cgtttctggg
6961 tgagcaaaaa caggaaggca aaatgccgca aaaaagggaa taagggcgac acggaaatgt
7021 tgaatactca tactcttcct ttttcaatat tattgaagca tttatcaggg ttattgtctc
7081 atgagcggat acatatttga atgtatttag aaaaataaac aGCGATCGCG CGGCCGCggg
7141 taataactga tataattaaa ttgaagctct aatttgtgAG TTTAGTATAC ATGCATTTAC
7201 TTATAATACA GTTTTTTAGT TTTGCTGGCC GCATCTTCTC AAATATGCTT CCCAGCCTGC
7261 TTTTCTGTAA CGTTCACCCT CTACCTTAGC ATCCCTTCCC TTTGCAAATA GTCCTCTTCC
7321 AACAATAATA ATGTCAGATC CTGTAGAGAC CACATCATCC ACGGTTCTAT ACTGTTGACC
7381 CAATGCGTCT CCCTTGTCAT CTAAACCCAC ACCGGGTGTC ATAATCAACC AATCGTAACC
7441 TTCATCTCTT CCACCCATGT CTCTTTGAGC AATAAAGCCG ATAACAAAAT CTTTGTCGCT
7501 CTTCGCAATG TCAACAGTAC CCTTAGTATA TTCTCCAGTA GCTAGGGAGC CCTTGCATGA
7561 CAATTCTGCT AACATCAAAA GGCCTCTAGG TTCCTTTGTT ACTTCTTCCG CCGCCTGCTT
7621 CAAACCGCTA ACAATACCTG GGCCACCAC ACCGTGTGCA TTCGTAATGT CTGCCCATTC
7681 TGCTATTCTG TATACACCCG CAGAGTACTG CAATTTGACT GTATTACCAA TGTCAGCAAA
7741 TTTTCTGTCT TCGAAGAGTA AAAATTGTA CTTGGCGGAT AATGCCTTTA GCGGCTTAAC
7801 TGTGCCCTCC ATGGAAAAAT CAGTCAAGAT ATCCACATGT GTTTTAGTA AACAAATTTT
7861 GGGACCTAAT GCTTCAACTA ACTCCAGTAA TTCCTTGGTG GTACGAACAT CCAATGAAGC
7921 ACACAAGTTT GTTTGCTTTT CGTGCATGAT ATTAAATAGC TTGGCAGCAA CAGGACTAGG
7981 ATGAGTAGCA GCACGTTCCT TATATGTAGC TTTCGACATG ATTTATCTTC GTTTCCTGCA
8041 GGTTTTTGTT CTGTGCAGTT GGGTTAAGAA TACTGGGCAA TTTCATGTTT CTTCAACACC
8101 ACATATGCGT ATATATACCA ATCTAAGTCT GTGCTCCTTC CTTCGTTctt ccttctgCtc
8161 ggagattacc gaatcAAAGC TAGC
```

Figure 12
(a)
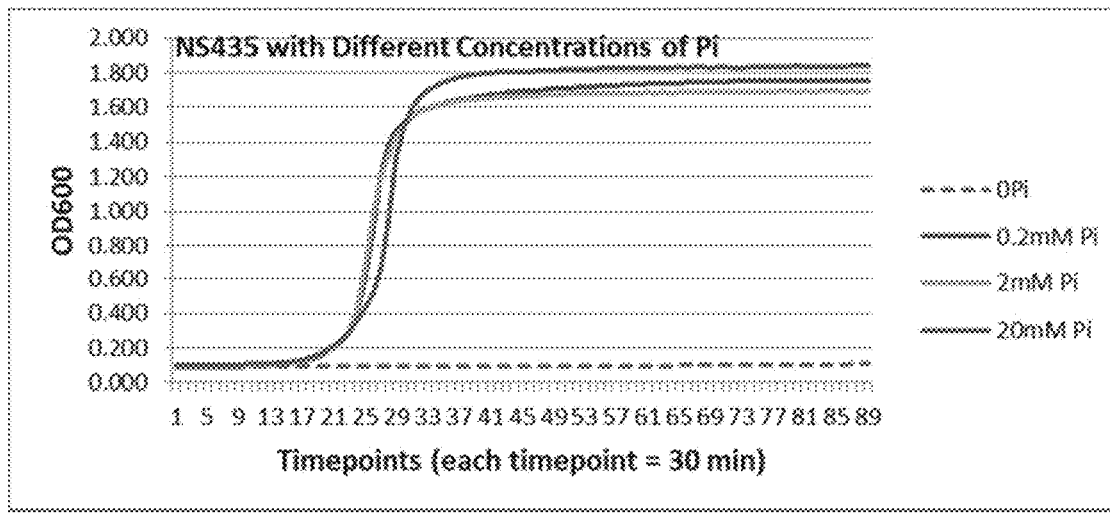
(b)
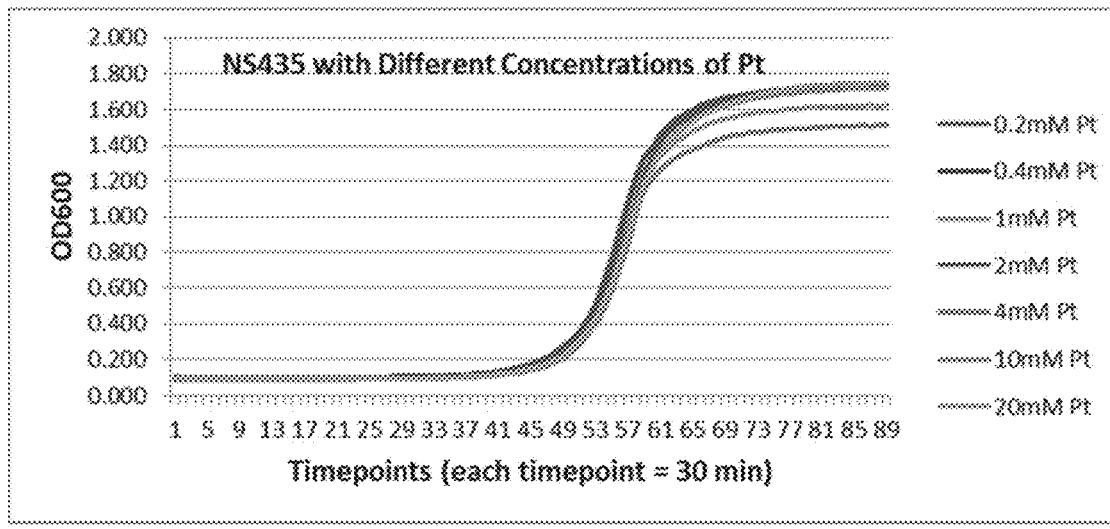

Figure 14

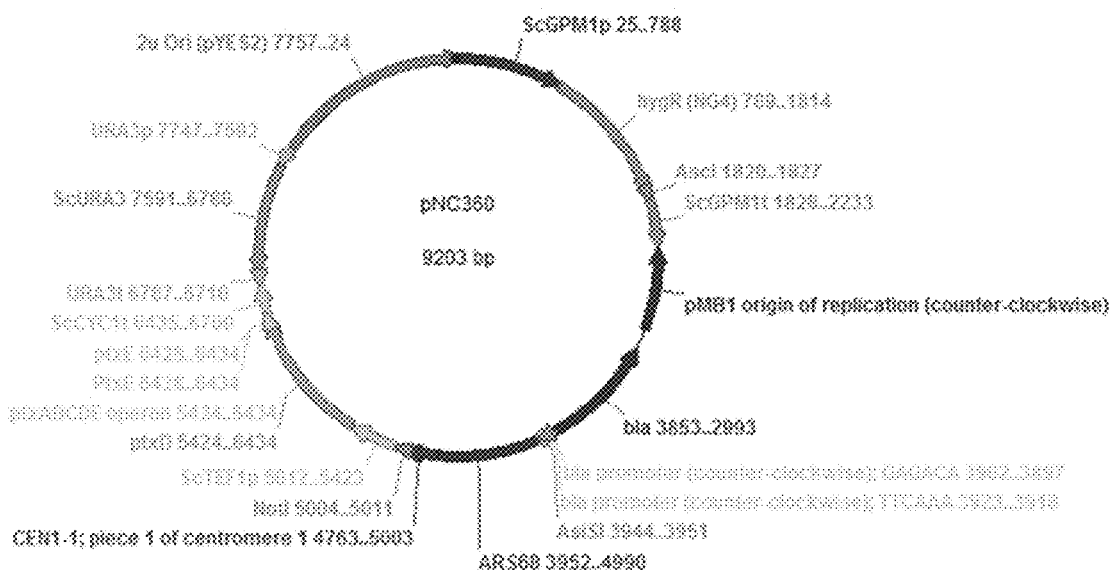

Figure 15

```
LOCUS       pNC360                   9203 bp ds-DNA    circular     09-JUL-2014
DEFINITION  .
ACCESSION
VERSION
SOURCE      .
  ORGANISM  .
COMMENT
COMMENT
COMMENT     ApEinfo:methylated:1
FEATURES             Location/Qualifiers
     misc_feature    join(7757..9203,1..24)
                     /label=2u Ori (pYES2)
                     /ApEinfo_fwdcolor=#8080ff
                     /ApEinfo_revcolor=#8080ff
                     /ApEinfo_graphicformat=arrow_data {{0 1 2 0 0 -1} {} 0}
                     width 5 offset 0
     misc_feature    25..788
                     /label=ScGPM1p
                     /ApEinfo_fwdcolor=#c70cdc
                     /ApEinfo_revcolor=#c70cdc
                     /ApEinfo_graphicformat=arrow_data {{0 1 2 0 0 -1} {} 0}
                     width 5 offset 0
```

Figure 15 (continued)

```
    rep_origin      3952..4990
                    /note="ARS68"
                    /label=ARS68
                    /ApEinfo_fwdcolor=#ff0080
                    /ApEinfo_revcolor=#ff0080
                    /ApEinfo_graphicformat=arrow_data {{0 1 2 0 0 -1} {} 0}
                    width 5 offset 0
    misc_feature    1828..2233
                    /label=ScGPM1t
                    /ApEinfo_fwdcolor=#eb74f8
                    /ApEinfo_revcolor=#eb74f8
                    /ApEinfo_graphicformat=arrow_data {{0 1 2 0 0 -1} {} 0}
                    width 5 offset 0
    gene            5424..6434
                    /gene="ptxABCDE operon"
                    /note="phosphite oxidation operon"
                    /label=ptxABCDE operon
                    /ApEinfo_fwdcolor=pink
                    /ApEinfo_revcolor=pink
                    /ApEinfo_graphicformat=arrow_data {{0 1 2 0 0 -1} {} 0}
                    width 5 offset 0
    CDS             complement(6788..7591)
                    /label=ScURA3
                    /ApEinfo_fwdcolor=#00c4c4
                    /ApEinfo_revcolor=#00c4c4
                    /ApEinfo_graphicformat=arrow_data {{0 1 2 0 0 -1} {} 0}
                    width 5 offset 0
    misc_feature    complement(7592..7747)
                    /label=URA3p
                    /ApEinfo_fwdcolor=#ff8000
                    /ApEinfo_revcolor=green
                    /ApEinfo_graphicformat=arrow_data {{0 1 2 0 0 -1} {} 0}
                    width 5 offset 0
    rep_origin      complement(2234..2822)
                    /note="pMB1 origin of replication (counter-clockwise)
                    (RNAII -35 to RNA/DNA switch point)"
                    /label=pMB1 origin of replication (counter-clockwise) (RN
                    /ApEinfo_fwdcolor=#ff0000
                    /ApEinfo_revcolor=#ff0000
                    /ApEinfo_graphicformat=arrow_data {{0 1 2 0 0 -1} {} 0}
                    width 5 offset 0
    misc_feature    6435..6709
                    /label=ScCYC1t
                    /ApEinfo_fwdcolor=#00ffff
                    /ApEinfo_revcolor=green
                    /ApEinfo_graphicformat=arrow_data {{0 1 2 0 0 -1} {} 0}
                    width 5 offset 0
    misc_feature    4763..5003
                    /note="CEN1-1; piece 1 of centromere 1"
                    /label=CEN1-1; piece 1 of centromere 1
                    /ApEinfo_fwdcolor=#ff00ff
                    /ApEinfo_revcolor=#ff00ff
                    /ApEinfo_graphicformat=arrow_data {{0 1 2 0 0 -1} {} 0}
                    width 5 offset 0
    misc_feature    5012..5423
                    /label=ScTEF1p
                    /ApEinfo_fwdcolor=#00ffff
                    /ApEinfo_revcolor=green
```

Figure 15 (continued)

```
                        /ApEinfo_graphicformat=arrow_data {{0 1 2 0 0 -1} {} 0}
                        width 5 offset 0
    -10_signal          complement(3897..3902)
                        /note="bla promoter (counter-clockwise); GAGACA"
                        /label=bla promoter (counter-clockwise); GAGACA
                        /ApEinfo_fwdcolor=pink
                        /ApEinfo_revcolor=pink
                        /ApEinfo_graphicformat=arrow_data {{0 1 2 0 0 -1} {} 0}
                        width 5 offset 0
    CDS                 789..1814
                        /label=hygR (NG4)
                        /ApEinfo_fwdcolor=#00d700
                        /ApEinfo_revcolor=#00a200
                        /ApEinfo_graphicformat=arrow_data {{0 1 2 0 0 -1} {} 0}
                        width 5 offset 0
    misc_feature        complement(6710..6787)
                        /label=URA3t
                        /ApEinfo_fwdcolor=#ff00ff
                        /ApEinfo_revcolor=green
                        /ApEinfo_graphicformat=arrow_data {{0 1 2 0 0 -1} {} 0}
                        width 5 offset 0
    gene                5424..6434
                        /gene="ptxD"
                        /label=ptxD
                        /ApEinfo_fwdcolor=#00e800
                        /ApEinfo_revcolor=#00e800
                        /ApEinfo_graphicformat=arrow_data {{0 1 2 0 0 -1} {} 0}
                        width 5 offset 0
    gene                complement(2993..3853)
                        /gene="bla"
                        /label=bla
                        /ApEinfo_fwdcolor=#ff0000
                        /ApEinfo_revcolor=#ff0000
                        /ApEinfo_graphicformat=arrow_data {{0 1 2 0 0 -1} {} 0}
                        width 5 offset 0
    -35_signal          complement(3918..3923)
                        /note="bla promoter (counter-clockwise); TTCAAA"
                        /label=bla promoter (counter-clockwise); TTCAAA
                        /ApEinfo_fwdcolor=pink
                        /ApEinfo_revcolor=pink
                        /ApEinfo_graphicformat=arrow_data {{0 1 2 0 0 -1} {} 0}
                        width 5 offset 0
    misc_feature        3944..3951
                        /label=AsiSI
                        /ApEinfo_fwdcolor=#ff8040
                        /ApEinfo_revcolor=#ff8040
                        /ApEinfo_graphicformat=arrow_data {{0 1 2 0 0 -1} {} 0}
                        width 5 offset 0
    misc_feature        1820..1827
                        /label=AscI
                        /ApEinfo_fwdcolor=#00b9b9
                        /ApEinfo_revcolor=#00b9b9
                        /ApEinfo_graphicformat=arrow_data {{0 1 2 0 0 -1} {} 0}
                        width 5 offset 0
    misc_feature        5004..5011
                        /label=NotI
                        /ApEinfo_fwdcolor=#ff8040
                        /ApEinfo_revcolor=#ff8040
```

Figure 15 (continued)

```
                    /ApEinfo_graphicformat=arrow_data {{0 1 2 0 0 -1} {} 0}
                    width 5 offset 0
     gene           6428..6434
                    /gene="ptxE"
                    /label=ptxE
                    /ApEinfo_fwdcolor=pink
                    /ApEinfo_revcolor=pink
                    /ApEinfo_graphicformat=arrow_data {{0 1 2 0 0 -1} {} 0}
                    width 5 offset 0
     CDS            6428..6434
                    /gene="ptxE"
                    /note="putative transcriptional regulator of ptx operon;
                    similar to lysR family of transcriptional regulators"
                    /codon_start=1
                    /transl_table=11
                    /product="PtxE"
                    /protein_id="AAC71710.1"
                    /db_xref="GI:3127081"
                    /translation="MLNPVWLKSLVAIVQTGSFQSAARALGLAQPTVSQHLQKLEEQV
                    GVTLVQRSRSGCQPTTRALAFMPHATALLDMHARALEALHGNRERVGASSNIGTYLLQ
                    PFVRNYLTTANERGEVDLRIAANPDVADQLLAGQLDAAIMEWWLPHPDFEYRLWRVEP
                    LVLIVSPDHALAEAGCIERDRLVDLPMLGGEPGSGT"
                    /label=PtxE
                    /ApEinfo_fwdcolor=pink
                    /ApEinfo_revcolor=pink
                    /ApEinfo_graphicformat=arrow_data {{0 1 2 0 0 -1} {} 0}
                    width 5 offset 0
ORIGIN
        1 GTTTGTGGAA GCGGTATTCG CAATCATTTA GTCGTGCAAT GTATGACTTT AAGATTTGTG
       61 AGCAGGAAGA AAAGGGAGAA TCTTCTAACG ATAAACCCTT GAAAAACTGG GTAGACTACG
      121 CTATGTTGAG ttgctacgca ggctgcacaa ttacACGAGA ATGCTCCCGC CTAGGATTTA
      181 AGGCTAAGGG ACGTGCAATG CAGACGACAG ATCTAAATGA CCGTGTCGGT GAAGTGTTCG
      241 CCAAACTTTT CGGTTAACAC ATGCAGTGAT GCACGCGCGA TGGTGCTAAG TTACATATAT
      301 ATATATATAT ATATATATAT ATATATATAG CCATAGTGAT GTCTAAGTAA CCTTTATGGT
      361 ATATTTCTTA ATGTGGAAAG ATACTAGCGC GCGCACCCAC ACACAAGCTT CGTCTTTTCT
      421 TGAAGAAAAG AGGAAGCTCG CTAAATGGGA TTCCACTTTC CGTTCCCTGC CAGCTGATGG
      481 AAAAAGGTTA GTGGAACGAT GAAGAATAAA AAGAGAGATC CACTGAGGTG AAATTTCAGC
      541 TGACAGCGAG TTTCATGATC GTGATGAACA ATGGTAACGA GTTGTGGCTG TTGCCAGGGA
      601 GGGTGGTTCT CAACTTTTAA TGTATGGCCA AATCGCTACT TGGGTTTGTT ATATAACAAA
      661 GAAGAAATAA TGAACTGATT CTCTTCCTCC TTCTTGTCCT TTCTTAATTC TGTTGTAATT
      721 ACCTTCCTTT GTAATTTTTT TTGTAATTAT TCTTCTTAAT AATCCAAACA AACACACATA
      781 TTACAATAAT GAAGAAGCCC GAGCTGACCG CTACCTCTGT TGAGAAGTTC CTGATTGAGA
      841 AGTTTGATTC CGTTTCCGAC CTGATGCAGC TGTCCGAGGG CGAGGAGTCT CGAGCCTTCT
      901 CCTTTGACGT GGGCGGACGA GGTTACGTTC TGCGAGTGAA CTCGTGTGCC GACGGCTTCT
      961 ACAAGGATCG ATACGTCTAC CGACACTTTG CTTCTGCCGC TCTGCCCATC CCTGAGGTTC
     1021 TCGACATTGG CGAGTTCTCT GAGTCCCTCA CCTACTGCAT CTCTCGACGA GCTCAGGGAG
     1081 TCACCCTGCA GGACCTCCCT GAGACTGAGC TGCCTGCTGT CCTCCAGCCT GTTGCTGAGG
     1141 CCATGGACGC TATCGCTGCT GCTGATCTGT CCCAGACCTC GGGTTTCGGC CCCTTTGGAC
     1201 CTCAGGGAAT TGGACAGTAC ACCACTTGGC GAGACTTCAT CTGTGCTATT GCCGATCCTC
     1261 ACGTCTACCA TTGGCAGACC GTTATGGACG ATACTGTGTC GGCTTCTGTC GCTCAGGCTC
     1321 TGGACGAGCT GATGCTCTGG GCCGAGGATT GCCCCGAGGT TCGACACCTG GTGCATGCTG
     1381 ACTTCGGTTC CAACAACGTT CTCACCGACA ACGGCCGAAT CACTGCCGTG ATTGACTGGT
     1441 CCGAGGCTAT GTTTGGCGAC TCGCAGTACG AGGTGGCCAA CATCTTCTTT TGGCGACCCT
     1501 GGCTGGCTTG TATGGAGCAG CAGACCCGAT ACTTCGAGCG ACGACATCCT GAGCTCGCTG
     1561 GATCCCCTCG ACTGCGAGCT TACATGCTCC GAATTGGTCT GGACCAGCTC TACCAGTCGC
     1621 TGGTGGATGG CAACTTTGAC GATGCTGCCT GGGCTCAGGG ACGATGTGAC GCCATCGTGC
     1681 GATCTGGCGC TGAACCGTC GGACGAACTC AGATTGCCCG ACGATCCGCT GCTGTCTGGA
     1741 CCGACGGATG CGTGGAGGTC CTGGCTGATT CGGGTAACCG ACGACCCTCT ACTCGACCTC
```

Figure 15 (continued)

```
1801 GAGCTAAGGA GTAAtaaacg gcgcgccGTC TGAAGAATGA ATGATTTGAT GATTTCTTTT
1861 TCCCTCCATT TTTCTTACTG AATATATCAA TGATATAGAC TTGTATAGTT TATTATTTCA
1921 AATTAAGTAG CTATATATAG TCAAGATAAC GTTTGTTTGA CACGATTACA TTATTCGTCG
1981 ACATCTTTTT TCAGCCTGTC GTGGTAGCAA TTTGAGGAGT ATTATTAATT GAATAGGTTC
2041 ATTTTGCGCT CGCATAAACA GTTTCGTCA GGGACAGTAT GTTGGAATGA GTGGTAATTA
2101 ATGGTGACAT GACATGTTAT AGCAATAACC TTGATGTTTA CATCGTAGTT TAATGTACAC
2161 CCCGCGAATT CGTTCAAGTA ggagtgcacc aattgcaaag ggaaAAGCTG AATGGGCAGT
2221 TCGAATAGTA CTTtttccat aggctccgcc ccctgacga gcatcacaaa aatcgacgct
2281 caagtcagag gtggcgaaac ccgacaggac tataagata ccaggcgttt cccctggaa
2341 gctccctcgt gcgctctcct gttccgaccc tgccgcttac cggatacctg tccgcctttc
2401 tcccttcggg aagcgtggcg ctttctcata gctcacgctg taggtatctc agttcggtgt
2461 aggtcgttcg ctccaagctg ggctgtgtgc acgaaccccc cgttcagccc gaccgctgcg
2521 ccttatccgg taactatcgt cttgagtcca acccgtaag acacgactta tcgccactgg
2581 cagcagccac tggtaacagg attagcagag cgaggtatgt aggcggtgct acagagttct
2641 tgaagtggtg gcctaactac ggctacacta gaagaacagt atttggtatc tgcgctctgc
2701 tgaagccagt taccttcgga aaaagagttg gtagctcttg atccggcaaa caaccaccg
2761 ctggtagcgg tggttttttt gtttgcaagc agcagattac gcgcagaaaa aaaggatctc
2821 aagaagatcc tttgatcttt tctacgggt ctgacgctca gtggaacgaa aactcacgtt
2881 aagggatttt ggtcatgaga ttatcaaaaa ggatcttcac ctagatcctt ttaaattaaa
2941 aatgaagttt taaatcaatc taagtatat atgagtaaac ttggtctgac agttaccaat
3001 gcttaatcag tgaggcacct atctcagcga tctgtctatt tcgttcatcc atagttgcct
3061 gactcccgt cgtgtagata actacgatac gggagggctt accatctggc cccagtgctg
3121 caatgatacc gcgagaccca cgctcaccgg ctccagattt atcagcaata aaccagccag
3181 ccggaagggc cgagcgcaga agtggtcctg caactttatc cgcctccatc cagtctatta
3241 attgttgccg ggaagctaga gtaagtagtt cgccagttaa tagtttgcgc aacgttgttg
3301 ccattgctac aggcatcgtg gtgtcacgct cgtcgtttgg tatggcttca ttcagctccg
3361 gttcccaacg atcaaggcga gttacatgat cccccatgtt gtgcaaaaaa gcggttagct
3421 ccttcggtcc tccgatcgtt gtcagaagta agttggccgc agtgttatca ctcatggtta
3481 tggcagcact gcataattct cttactgtca tgccatccgt aagatgcttt tctgtgactg
3541 gtgagtactc aaccaagtca ttctgagaat agtgtatgcg gcgaccgagt tgctcttgcc
3601 cggcgtcaat acgggataat accgcgccac atagcagaac tttaaaagtg ctcatcattg
3661 gaaaacgttc ttcggggcga aaactctcaa ggatcttacc gctgttgaga tccagttcga
3721 tgtaacccac tcgtgcaccc aactgatctt cagcatcttt tactttcacc agcgtttctg
3781 ggtgagcaaa aacaggaagg caaaatgccg caaaaaaggg aatagggcg acacggaaat
3841 gttgaatact catactcttc cttttcaat attattgaag catttatcag ggttattgtc
3901 tcatgagcgg atacatattt gaatgtattt agaaaaataa acaGCGATCG CAGCTAGCTC
3961 GTCGTGTTCA GGAACtgttc gatggttcgg agagagtcgc cgcccagaac atacgcgcac
4021 cgatgtcagc agacagcctt attacaagta tattcaagca agtatatccg tagggtgcgg
4081 gtgatttgga tctaaggttc gtactcaaca ctcacgagca gcttgcctat gttacatcct
4141 tttatcagac ataacataat tggagtttac ttacacacgg ggtgtacctg tatgagcacc
4201 acctacaatt gtagcactgg tacttgtaca aagaatttat tcgtacgaat cacagggacg
4261 gccgccctca ccgaaccagc gaatacctca gcggtcccct gcagtgactc aacaaagcga
4321 tatgaacatc ttgcgatggt atcctgctga tagttttac tgtacaaaca cctgtgtagc
4381 tccttctagc atttttaagt tattcacacc tcaagggag ggataaatta aataaattcc
4441 aaaagcgaag atcgagaaac taaattaaaa ttccaaaaac gaagttggaa cacaaccccc
4501 cgaaaaaaaa caacaaacaa aaaacccaac aaaataaaca aaaacaaaat aaatatataa
4561 ctaccagtat ctgactaaaa gttcaaatac tcgtacttac aacaaataga aatgagccgg
4621 ccaaaattct gcagaaaaaa atttcaaaca agtactggta taattaaatt aaaaaacaca
4681 tcaaagtatc ataacgttag ttatttatt ttatttaata aagaaaaca acaagatggg
4741 ctcaaaactt tcaacttata cgATACATAC CAAATAACAA TTTAGTATTT ATCTAAGTGC
4801 TTTTCGTAGA TAATGGAATA CAAATGGATA TCCAGAGTAT ACACATGGAT AGTATACACT
4861 GACACGACAA TTCTGTATCT CTTTATGTTA ACTACTGTGA GGCATTAAAT AGAGCTTGAT
4921 ATATAAAATG TTACATTTCA CAGTCTGAAC TTTTGCAGAT TACCTAATt ggtaagatat
4981 taattatgaa ctgaaagttg atgGCGGCCG CATAGCTTCA AAATGTTTCT ACTCCTTTTT
5041 TACTCTTCCA GATTTTCTCG GACTCCGCGC ATCGCCGTAC CACTTCAAAA CACCCAAGCA
5101 CAGCATACTA AATTTCCCCT CTTTCTTCCT CTAGGGTGTC GTTAATTACC CGTACTAAAG
5161 GTTTGGAAAA GAAAAAAGAG ACCGCCTCGT TTCTTTTTCT TCGTCGAAAA AGGCAATAAA
5221 AATTTTTATC ACGTTTCTTT TTCTTGAAAA TTTTTTTTTT TGATTTTTTT CTCTTTCGAT
```

Figure 15 (continued)

```
5281 GACCTCCCAT TGATATTTAA GTTAATAAAC GGTCTTCAAT TTCTCAAGTT TCAGTTTCAT
5341 TTTTCTTGTT CTATTACAAC TTTTTTTACT TCTTGCTCAT TAGAAAGAAA GCATAGCAAT
5401 CTAATCTAAG TTTTAATTAC AAAatgctgc cgaaactcgt tataactcac cgagtacacg
5461 atgagatcct gcaactgctg gcgccacatt gcgagctgat gaccaaccag accgacagca
5521 cgctgacgcg cgaggaaatt ctgcgccgct gtcgcgatgc tcaggcgatg atggcgttca
5581 tgccgatcg ggtcgatgca gactttcttc aagcctgccc tgagctgcgt gtagtcggct
5641 gcgcgctcaa gggcttcgac aatttcgatg tggacgcctg tactgcccgc ggggtctggc
5701 tgaccttcgt gcctgatctg ttgacggtcc cgactgccga gctggcgatc ggactggcgg
5761 tggggctggg gcggcatctg cgggcagcag atgcgttcgt ccgctctggc gagttccagg
5821 gctggcaacc acagttctac ggcacgggc tggataacgc tacggtcggc atccttggca
5881 tgggcgccat cggactggcc atggctgatc gcttgcaggg atgggcgcg accctgcagt
5941 accacgagc gaaggctctg gatacacaaa ccgagcaacg gctcggcctg cgccaggtgg
6001 cgtgcagcga actcttcgcc agctcggact tcatcctgct ggcgcttccc ttgaatgccg
6061 atacccagca tctggtcaac gccgagctgc ttgccctcgt acggccgggc gctctgcttg
6121 taaaccctg tcgtggttcg gtagtggatg aagccgcgt gctcgcggcg cttgagcgag
6181 gccagctcgg cgggtatgcg gcggatgtat tcgaaatgga agactgggct cgcgcggacc
6241 ggccgcggct gatcgatcct gcgctgctcg cgcatccgaa tacgctgttc actccgcaca
6301 tagggtcggc agtgcgcgcg gtgcgcctgg agattgaacg ttgtgcagcg cagaacatca
6361 tccaggtatt ggcaggtgcg cgcccaatca acgctgcgaa ccgtctgccc aaggccgagc
6421 ctgccgcatg ttgaacaggc cccttttcct ttgtcgatat catgtaatta gttatgtcac
6481 gcttacattc acgccctcct cccacatccg ctctaaccga aaggaagga gttagacaac
6541 ctgaagtcta ggtccctatt tattttttt aatagttatg ttagtattaa gaacgttatt
6601 tatatttcaa attttctttt ttttctgta caaacgcgtg tacgcatgta acattatact
6661 gaaaaccttg cttgagaagg ttttgGGACG CTCGAAGGCT TTAATTTGCg ggtaataact
6721 gatataatta aattgaagct ctaatTTGTG AGTTTAGTAT ACATGCATTT ACTTATAATA
6781 CAGTTTTTTA GTTTTGCTGG CCGCATCTTC TCAAATATGC TTCCCAGCCT GCTTTTCTGT
6841 AACGTCACC CTCTACCTTA GCATCCCTTC CCTTTGCAAA TAGTCCTCTT CCAACAATAA
6901 TAATGTCAGA TCCTGTAGAG ACCACATCAT CCACGGTTCT ATACTGTTGA CCCAATGCGT
6961 CTCCCTTGTC ATCTAAACCC ACACCGGGTG TCATAATCAA CCAATCGTAA CCTTCATCTC
7021 TTCCACCCAT GTCTCTTTGA GCAATAAAGC CGATAACAAA ATCTTTGTCG CTCTTCGCAA
7081 TGTCAACAGT ACCCCTAGTA TATTCTCCAG TAGCTAGGGA GCCCTTGCAT GACAATTCTG
7141 CTAACATCAA AAGGCCTCTA GGTTCCTTTG TTACTTCTTC CGCCGCCTGC TTCAAACCGC
7201 TAACAATACC TGGGCCCACC ACACCGTGTG CATTCGTAAT GTCTGCCCAT TCTGCTATTC
7261 TGTATACACC CGCAGAGTAC TGCAATTTGA CTGTATTACC AATGTCAGCA AATTTTCTGT
7321 CTTCGAAGAG TAAAAAATTG TACTTGGCGG ATAATGCCTT TAGCGGCTTA ACTGTGCCCT
7381 CCATGGAAAA ATCAGTCAAG ATATCCACAT GTGTTTTTAG TAAACAAATT TTGGGACCTA
7441 ATGCTTCAAC TAACTCCAGT AATTCCTTGG TGGTACGAAC ATCCAATGAA GCACACAAGT
7501 TTGTTTGCTT TTCGTGCATG ATATTAAATA GCTTGGCAGC AACAGGACTA GGATGAGTAG
7561 CAGCACGTTC CTTATATGTA GCTTTCGACA TGATTTATCT TCGTTCCTG CAGGTTTTTG
7621 TTCTGTGCAG TTGGGTTAAG AATACTGGGC AATTTCATGT TTCTTCAACA CCACATATGC
7681 GTATATATAC CAATCTAAGT CTGTGCTCCT TCCTTCGTTc ttccttctgC tcggagatta
7741 ccgaatcAAA GCTAGCTTAT CGATGATAAG CTGTCAAAGA TGAGAATTAA TTCCACGGAC
7801 TATAGACTAT ACTAGATACT CCGTCTACTG TACGATACAC TTCCGCTCAG GTCCTTGTCC
7861 TTTAACGAGG CCTTACCACT CTTTTGTTAC TCTATTGATC CAGCTCAGCA AAGGCAGTGT
7921 GATCTAAGAT TCTATCTTCG CGATGTAGTA AAACTAGCTA GACCGAGAAA GAGACTAGAA
7981 ATGCAAAAGG CACTTCTACA ATGGCTGCCA TCATTATTAT CCGATGTGAC GCTGCAGCTT
8041 CTCAATGATA TTCGAATACG CTTGAGGAG ATACAGCCTA ATATCCGACA AACTGTTTTA
8101 CAGATTTACG ATCGTACTTG TTACCCATCA TTGAATTTTG AACATCCGAA CCTGGGAGTT
8161 TTCCCTGAAA CAGATAGTAT ATTTGAACCT GTATAATAAT ATATAGTCTA GCGCTTTACG
8221 GAAGACAATG TATGTATTTC GGTTCCTGGA GAAACTATTG CATCTATTGC ATAGGTAATC
8281 TTGCACGTCG CATCCCCGGT TCATTTCTG CGTTTCCATC TTGCACTTCA ATAGCATATC
8341 TTTGTTAACG AAGCATCTGT GCTTCATTTT GTAGAACAAA AATGCAACGC GAGAGCGCTA
8401 ATTTTTCAAA CAAAGAATCT GAGCTGCATT TTTACAGAAC AGAAATGCAA CGCGAAAGCG
8461 CTATTTTACC AACGAAGAAT CTGTGCTTCA TTTTTGTAAA ACAAAAATGC AACGCGACGA
8521 GAGCGCTAAT TTTTCAAACA AAGAATCTGA GCTGCATTTT TACAGAACAG AAATGCAACG
8581 CGAGAGCGCT ATTTTACCAA CAAAGAATCT ATACTTCTTT TTTGTTCTAC AAAAATGCAT
8641 CCCGAGAGCG CTATTTTTCT AACAAAGCAT CTTAGATTAC TTTTTTCTC CTTTGTGCGC
8701 TCTATAATGC AGTCTCTTGA TAACTTTTTG CACTGTAGGT CCGTTAAGGT TAGAAGAAGG
```

Figure 15 (continued)

```
8761 CTACTTTGGT GTCTATTTTC TCTTCCATAA AAAAAGCCTG ACTCCACTTC CCGCGTTTAC
8821 TGATTACTAG CGAAGCTGCG GGTGCATTTT TTCAAGATAA AGGCATCCCC GATTATATTC
8881 TATACCGATG TGGATTGCGC ATACTTTGTG AACAGAAAGT GATAGCGTTG ATGATTCTTC
8941 ATTGGTCAGA AAATTATGAA CGGTTTCTTC TATTTTGTCT CTATATACTA CGTATAGGAA
9001 ATGTTTACAT TTTCGTATTG TTTTCGATTC ACTCTATGAA TAGTTCTTAC TACAATTTTT
9061 TTGTCTAAAG AGTAATACTA GAGATAAACA TAAAAAATGT AGAGGTCGAG TTTAGATGCA
9121 AGTTCAAGGA GCGAAAGGTG GATGGGTAGG TTATATAGGG ATATAGCACA GAGATATATA
9181 GCAAAGAGAT ACTTTTGAGC AAT
```

Figure 16

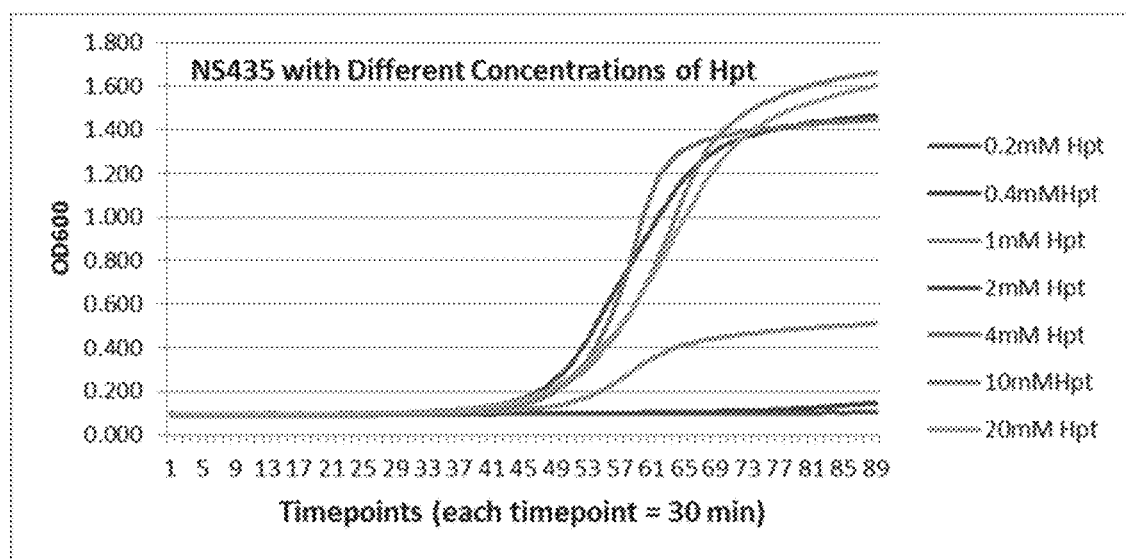

Figure 18

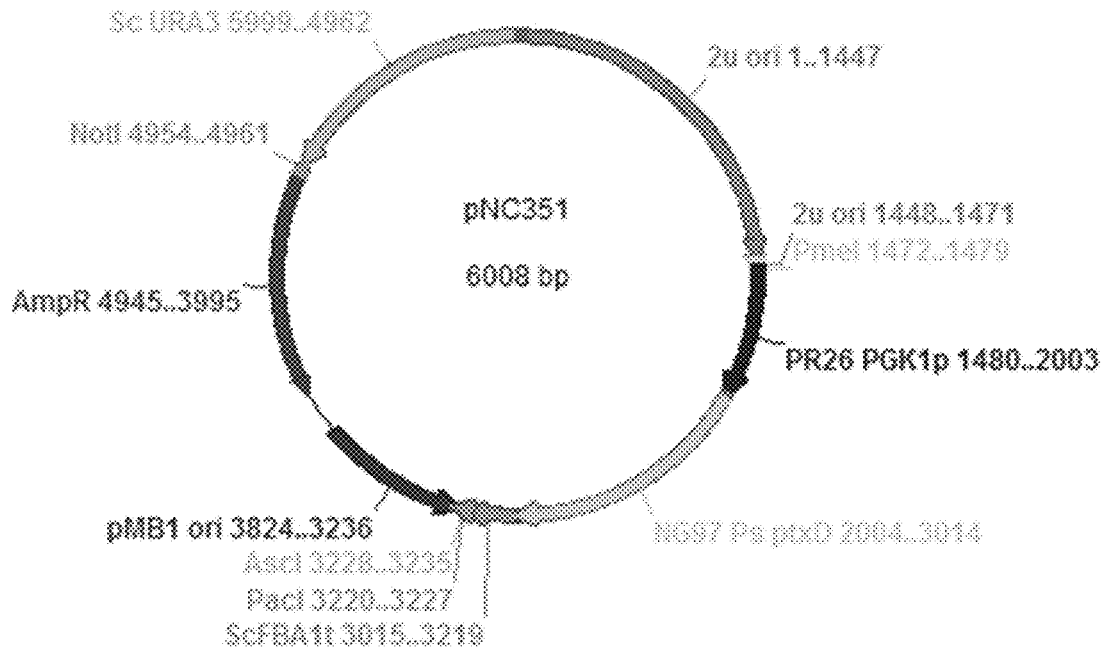

Figure 19

```
LOCUS       pNC351          6008 bp ds-DNA     circular    21-MAR-2014
DEFINITION  .
ACCESSION
VERSION
SOURCE      .
  ORGANISM  .
COMMENT
COMMENT
COMMENT     ApEinfo:methylated:1
FEATURES             Location/Qualifiers
     misc_feature    1448..1471
                     /label=2u ori
                     /ApEinfo_fwdcolor=#8080ff
                     /ApEinfo_revcolor=#8080ff
                     /ApEinfo_graphicformat=arrow_data {{0 1 2 0 0 -1} {} 0}
                     width 5 offset 0
     misc_feature    1..1447
                     /label=2u ori(1)
                     /ApEinfo_label=2u ori
                     /ApEinfo_fwdcolor=#8080ff
                     /ApEinfo_revcolor=#8080ff
```

Figure 19 (continued)

```
                    /ApEinfo_graphicformat=arrow_data {{0 1 2 0 0 -1} {} 0}
                    width 5 offset 0
     rep_origin     complement(3236..3824)
                    /note="pMB1 origin of replication (counter-clockwise)
                    (RNAII -35 to RNA/DNA switch point)"
                    /label=pMB1 ori
                    /ApEinfo_fwdcolor=#ff0000
                    /ApEinfo_revcolor=#ff0000
                    /ApEinfo_graphicformat=arrow_data {{0 1 2 0 0 -1} {} 0}
                    width 5 offset 0
     misc_feature   complement(3995..4945)
                    /label=AmpR
                    /ApEinfo_fwdcolor=#ff00ff
                    /ApEinfo_revcolor=#ff00ff
                    /ApEinfo_graphicformat=arrow_data {{0 1 2 0 0 -1} {} 0}
                    width 5 offset 0
     misc_feature   3015..3219
                    /label=ScFBA1t
                    /ApEinfo_fwdcolor=#eb74f8
                    /ApEinfo_revcolor=#eb74f8
                    /ApEinfo_graphicformat=arrow_data {{0 1 2 0 0 -1} {} 0}
                    width 5 offset 0
     misc_feature   complement(4962..5999)
                    /label=Sc URA3
                    /ApEinfo_fwdcolor=cyan
                    /ApEinfo_revcolor=#00ff00
                    /ApEinfo_graphicformat=arrow_data {{0 1 2 0 0 -1} {} 0}
                    width 5 offset 0
     misc_feature   3228..3235
                    /label=AscI
                    /ApEinfo_fwdcolor=#00ff00
                    /ApEinfo_revcolor=green
                    /ApEinfo_graphicformat=arrow_data {{0 1 2 0 0 -1} {} 0}
                    width 5 offset 0
     misc_feature   4954..4961
                    /label=NotI
                    /ApEinfo_fwdcolor=#ff8080
                    /ApEinfo_revcolor=green
                    /ApEinfo_graphicformat=arrow_data {{0 1 2 0 0 -1} {} 0}
                    width 5 offset 0
     misc_feature   1472..1479
                    /label=PmeI
                    /ApEinfo_fwdcolor=#00ffff
                    /ApEinfo_revcolor=green
                    /ApEinfo_graphicformat=arrow_data {{0 1 2 0 0 -1} {} 0}
                    width 5 offset 0
     misc_feature   3220..3227
                    /label=PacI
                    /ApEinfo_fwdcolor=#ff8040
                    /ApEinfo_revcolor=green
                    /ApEinfo_graphicformat=arrow_data {{0 1 2 0 0 -1} {} 0}
                    width 5 offset 0
     misc_feature   1480..2003
                    /label=PR26 PGK1p
                    /ApEinfo_fwdcolor=#800040
                    /ApEinfo_revcolor=green
                    /ApEinfo_graphicformat=arrow_data {{0 1 2 0 0 -1} {} 0}
                    width 5 offset 0
     misc_feature   2004..3014
                    /label=NG97 Ps ptxD
                    /ApEinfo_fwdcolor=cyan
                    /ApEinfo_revcolor=green
                    /ApEinfo_graphicformat=arrow_data {{0 1 2 0 0 -1} {} 0}
                    width 5 offset 0
```

Figure 19 (continued)

```
ORIGIN
        1 ttatcgatga taagctgtca aagatgagaa ttaattccac ggactataga ctatactaga
       61 tactccgtct actgtacgat acacttccgc tcaggtcctt gtcctttaac gaggccttac
      121 cactcttttg ttactctatt gatccagctc agcaaaggca gtgtgatcta agattctatc
      181 ttcgcgatgt agtaaaacta gctagaccga gaaagagact agaaatgcaa aaggcacttc
      241 tacaatggct gccatcatta ttatccgatg tgacgctgca gcttctcaat gatattcgaa
      301 tacgctttga ggagatacag cctaatatcc gacaaactgt tttacagatt tacgatcgta
      361 cttgttaccc atcattgaat tttgaacatc cgaacctggg agttttccct gaaacagata
      421 gtatatttga acctgtataa taatatatag tctagcgctt tacggaagac aatgtatgta
      481 tttcggttcc tggagaaact attgcatcta ttgcataggt aatcttgcac gtcgcatccc
      541 cggttcattt tctgcgtttc catcttgcac ttcaatagca tatctttgtt aacgaagcat
      601 ctgtgcttca ttttgtagaa caaaatgcca acgcgagagc gctaatttta caaacaaaga
      661 atctgagctg cattttaca gaacagaaat gcaacgcgaa agcgctattt taccaacgaa
      721 gaatctgtgc ttcattttg taaaacaaaa atgcaacgcg acgagagcgc taattttca
      781 aacaaagaat ctgagctgca tttttacaga acagaaatgc aacgcgagag cgctatttta
      841 ccaacaaaga atctatactt cttttttgtt ctacaaaaat gcatccgag agcgctattt
      901 ttctaacaaa gcatcttaga ttacttttt tctccttgt gcgtctata atgcagtctc
      961 ttgataactt tttgcactgt aggtccgtta aggttagaag aaggctactt tggtgtctat
     1021 ttctcttcc ataaaaaag cctgactcca cttcccgcgt ttactgatta ctagcgaagc
     1081 tgcgggtgca tttttcaag ataaaggcat cccgattat attctatcc gatgtggatt
     1141 gcgcatactt tgtgaacaga aagtgatagc gttgatgatt cttcattggt cagaaaatta
     1201 tgaacggttt cttctatttt gtctctatat actacgtata ggaaatgttt acattttcgt
     1261 attgttttcg attcactcta tgaatagttc ttactacaat ttttttgtct aaagagtaat
     1321 actagagata aacataaaaa atgtagaggt cgagtttaga tgcaagttca aggagcgaaa
     1381 ggtggatggg taggttatat agggatatag cacagagata tatagcaaag agatactttt
     1441 gagcaatgtt tGTGGAAGCG GTATTCGCAA TGTTTAAACc ccagcccgac ttttaacctc
     1501 aATAGCTAGC TACGCAACAG ACAGTTAAAG CTACGTACTC AACTATATAT TCCATTGACA
     1561 ATTGACAATT ACAACTGTTT CTTCTCCTGC ATCGTTCTCA TCCTCATTGG CTTATCTCCT
     1621 GTTATCAATT AATTATAATA ATATAGTAGT TCTGAACTAA TTACGTGATC GCACGCAGTA
     1681 CGGCTGACGC GTATTATTGG ACCAACAAAC CCTAAAAATT GTTTCATCCA ATTGAACAGT
     1741 TCACGCAACC GTGATTGTGC CAAAAAGGCA TTGCCGGCCT CAAGTAGGCG CCCATGCTAC
     1801 GACTACTGCG GTCTAGGCGC TCCCGTATCC CTCAATCGTG GCCCTTTCC GGTCTACCCG
     1861 CTGAGTCAGC CCCGCCCAAC AAAAAAAGCA CACCACAAGT TCGACATGGT CCAGGGGCAC
     1921 GGCTGCAGGG TTGCGGTATA AATACAGTCA CCATTTCCAC CGCACCTCCG TGctttgttt
     1981 ttcaattggc aacctataac acaATGCTGC CGAAACTCGT TATAACTCAC cgagtacacg
     2041 atgagatcct gcaactgctg gcgccacatt gcgagctgat gaccaaccag accgacagca
     2101 cgctgacgcg cgaggaaatt ctgcgccgct gtcgcgatgc tcaggcgatg atggcgttca
     2161 tgcccgatcg ggtcgatgca gactttcttc aagcctgccc tgagctgcgt gtagtcggct
     2221 gcgcgctcaa gggcttcgac aatttcgatg tggacgcctg tactgccgc ggggtctggc
     2281 tgaccttcgt gctgatctg ttgacggtcc cgactgcga gctggcgatc ggactggcgg
     2341 tgggctggg gcggcatctg cgggcagcag atgcgttcgt ccgctctggc gagttccagg
     2401 gctggcaacc acagttctac ggcacggggc tggataacgc tacggtcggc atccttggca
     2461 tgggcgccat cggactggcc atggctgatc gcttgcaggg atggggcgcg ccctgcagt
     2521 accacgaggc gaaggctctg gatacacaaa ccgagcaacg gctcggcctg cgccaggtgg
     2581 cgtgcagcga actcttcgcc agctcggact tcatcctgct ggcgcttccc ttgaatgccg
     2641 ataccccagca tctggtcaac gccgagctgc ttgcctcgt acggccggc gctctgcttg
     2701 taaccctg tcgtggttcg gtagtggatg aagccgcgt gctcgcggcg cttgagcgag
     2761 gccgctcgg cgggtatgcg gcggatgtat tcgaaatgga agactgggct cgcgcggaca
     2821 ggcgcgggct gatcgatcct gcgctgctcg cgcatccgaa tacgctgttc actccgcaca
     2881 tagggtcggc agtgcgcgcg gtgcgcctgg agattgaacg ttgtgcagcg cagaacatca
     2941 tccaggtatt ggcaggtgcg cgccaatca acgctgcgaa ccgtctgccc aaggCCGAGC
     3001 CTGCCGCATG TTGAgttaat tcaaattaat tgatataGTT TTTTAATGAG TATTGAATCT
     3061 GTTTAGAAAT AATGGAATAT TATTTTATT TATTATTTA TATTATTGGT CGGCTCTTTT
     3121 CTTCTGAAGG TCAATGACAA AATGATATGA AGGAAATAAT GATTTCTAAA ATTTACAAC
     3181 GTAAGATATT TTACAAAAG CCTAGCTCAT CTTTTGTCAt taattaaggc gcgccttcc
     3241 ataggctccg ccccctgacg gagcatcaca aaatcgacag ctcaagtcag aggtggcgaa
     3301 acccgacagg actataaaga taccaggcgt ttccccctgg aagctccctc gtgcgctctc
     3361 ctgttccgac cctgccgctt acggatacc tgtccgcctt tctccctcg ggaagcgtgg
     3421 cgctttctca tagctcacgc tgtaggtatc tcagttcggt gtaggtcgtt cgctccaagc
     3481 tgggctgtgt gcacgaaccc cccgttcagc ccgaccgctg cgccttatcc ggtaactatc
     3541 gtcttgagtc caacccggta agacacgact tatcgccact ggcagcagcc actggtaaca
     3601 ggattagcag agcgaggtat gtaggcggtg ctacagagtt cttgaagtgg tggcctaact
     3661 acggctacac tagaagaaca gtatttggta tctgcgctct gctgaagcca gttaccttcg
     3721 gaaaaagagt tggtagctct tgatccggca aacaaaccac cgctggtagc ggtggttttt
     3781 ttgtttgcaa gcagcagatt acgcgcagaa aaaaggatc tcaagaagat cctttgatct
     3841 tttctacggg gtctgacgct cagtggaacg aaaactcacg ttaagggatt ttggtcatga
```

Figure 19 (continued)

```
3901 gattatcaaa aaggatcttc acctagatcc ttttaaatta aaaatgaagt tttaaatcaa
3961 tctaaagtat atatgagtaa acttggtctg acagttacca atgcttaatc agtgaggcac
4021 ctatctcagc gatctgtcta tttcgttcat ccatagttgc ctgactccc gtcgtgtaga
4081 taactacgat acgggagggc ttaccatctg gccccagtgc tgcaatgata ccgcgagacc
4141 cacgctcacc ggctccagat ttatcagcaa taaaccagcc agccggaagg gccgagcgca
4201 gaagtggtcc tgcaacttta tccgcctcca tccagtctat taattgttgc cgggaagcta
4261 gagtaagtag ttcgccagtt aatagtttgc gcaacgttgt tgccattgct acaggcatcg
4321 tggtgtcacg ctcgtcgttt ggtatggctt cattcagctc cggttcccaa cgatcaaggc
4381 gagttacatg atcccccatg ttgtgcaaaa aagcggttag ctccttcggt cctccgatcg
4441 ttgtcagaag taagttggcc gcagtgttat cactcatggt tatggcagca ctgcataatt
4501 ctcttactgt catgccatcc gtaagatgct tttctgtgac tggtgagtac tcaaccaagt
4561 cattctgaga atagtgtatg cggcgaccga gttgctcttg cccggcgtca atacgggata
4621 ataccgcgcc acatagcaga actttaaaag tgctcatcat tggaaaacgt tcttcggggc
4681 gaaaactctc aaggatctta ccgctgttga gatccagttc gatgtaaccc actcgtgcac
4741 ccaactgatc ttcagcatct ttactttca ccagcgtttc tgggtgagca aaaacaggaa
4801 ggcaaaatgc cgcaaaaaag ggaataaggg cgacacggaa atgttgaata ctcatactct
4861 tcctttttca atattattga agcatttatc agggttattg tctcatgagc ggatacatat
4921 ttgaatgtat ttagaaaaat aaacaGCGAT CGCGCGGCCG Cgggtaataa ctgatataat
4981 taaattgaag ctctaatttg tgAGTTTAGT ATACATGCAT TTACTTATAA TACAGTTTTT
5041 TAGTTTGCT GGCCGCATCT TCTCAAATAT GCTTCCCAGC CTGCTTTTCT GTAACGTTCA
5101 CCCTCTACCT TAGCATCCCT TCCCTTTGCA AATAGTCCTC TTCCAACAAT AATAATGTCA
5161 GATCCTGTAG AGACCACATC ATCCACGGTT CTATACTGTT GACCCAATGC GTCTCCCTTG
5221 TCATCTAAAC CCACACCGGG TGTCATAATC AACCAATCGT AACCTTCATC TCTTCCACCC
5281 ATGTCTCTTT GAGCAATAAA GCCGATAACA AAATCTTTGT CGCTCTTCGC AATGTCAACA
5341 GTACCCTTAG TATATTCTCC AGTAGCTAGG GAGCCCTTGC ATGACAATTC TGCTAACATC
5401 AAAAGGCCTC TAGGTTCCTT TGTTACTTCT TCCGCCGCCT GCTTCAAACC GCTAACAATA
5461 CCTGGGCCCA CCACACCGTG TGCATTCGTA ATGTCTGCCC ATTCTGCTAT TCTGTATACA
5521 CCCGCAGAGT ACTGCAATTT GACTGTATTA CCAATGTCAG CAAATTTTCT GTCTTCGAAG
5581 AGTAAAAAAT TGTACTTGGC GGATAATGCC TTTAGCGGCT TAACTGTGCC CTCCATGGAA
5641 AAATCAGTCA AGATATCCAC ATGTGTTTTT AGTAAACAAA TTTTGGGACC TAATGCTTCA
5701 ACTAACTCCA GTAATTCCTT GGTGGTACGA ACATCCAATG AAGCACACAA GTTTGTTTGC
5761 TTTTCGTGCA TGATATTAAA TAGCTTGGCA GCAACAGGAC TAGGATGAGT AGCAGCACGT
5821 TCCTTATATG TAGCTTTCGA CATGATTTAT CTTCGTTTCC TGCAGGTTTT TGTTCTGTGC
5881 AGTTGGTTA AGAATACTGG GCAATTTCAT GTTTCTTCAA CACCACATAT GCGTATATAT
5941 ACCAATCTAA GTCTGTGCTC CTTCCTTCGT Tcttccttct gCtcggagat taccgaatcA
6001 AAGCTAGC
```

MICROORGANISMS ENGINEERED TO USE UNCONVENTIONAL SOURCES OF PHOSPHOROUS OR SULFUR

RELATED APPLICATIONS

This application is a divisional of U.S. patent application Ser. No. 14/914,817, filed Feb. 26, 2016, now U.S. Pat. No. 10,174,296, which is the U.S. national stage under 35 U.S.C. § 371 of PCT International Patent Application Serial No. PCT/US2014/052841, filed Aug. 27, 2014, which claims the benefit of priority to U.S. Provisional Patent Application Ser. No. 61/870,469, filed Aug. 27, 2013, the contents of each of which are hereby incorporated by reference.

SEQUENCE LISTING

The instant application contains a Sequence Listing, which has been submitted electronically in ASCII format and is hereby incorporated by reference in its entirety. Said ASCII copy, created on Apr. 9, 2019, is named NOVG_P0009US_D1_revised_sequence_listing.txt and is 78,527 bytes in size.

BACKGROUND

In the fermentation industry, cell culture media is typically formulated to provide all nutrients necessary for the growth of a host cell line, with particular emphasis on meeting the cell line's requirements for carbon, nitrogen, phosphorus, sulfur, and other major nutrients. Some cell lines require additional components, including amino acids, trace minerals and metals, and complex growth factors. The presence of these nutrients provides a suitable growth environment for the organism of choice and, unfortunately, for any potential contaminating organisms. In this environment the production organism is required to compete directly with any contaminant organism in the cell culture.

Even in robust hosts, the combination of opportunistic infections of the culture and the metabolic burden resulting from the demands of product manufacture is a major concern in monoculture operations. Industrial robustness is typically considered a multigenic trait specific to the host strain and thus difficult to engineer predictably into organisms late in the development process. Addition of selective growth inhibitors, such as bacterial antibiotics, is one method used to create a more robust fermentation environment for host organisms that are resistant to the growth inhibitor. However, antibiotic addition is often undesirable or unfeasible, and spontaneously resistant contaminations frequently result.

Accordingly, there exists a need for rationally engineered traits that, when engineered into a host organism, create a robust monoculture fermentation environment.

SUMMARY OF THE INVENTION

In certain embodiments, the invention relates to a genetically engineered organism, wherein the genetically engineered organism has been transformed by a nucleic acid molecule comprising any one of the sequences disclosed herein.

In certain embodiments, the invention relates to a genetically engineered organism, wherein the genetically engineered organism has been transformed by a nucleic acid molecule; the nucleic acid molecule comprises a non-native gene; and the non-native gene encodes for a non-native enzyme selected from the group consisting of NAD:phosphite oxidoreductase (phosphite dehydrogenase), glycerol-3-phosphate dehydrogenase (sn-glycerol 3-phosphate: NAD (+) oxidoreductase, EC 1.1.1.8), glyceraldehyde-3-phosphate dehydrogenase, an organophosphate degradation enzyme, a phosphodiesterase, a phospholipase, desulfurization enzyme, a dibenzothiophene-5,5-dioxide monooxygenase, a 2-hydroxybiphenyl-2-sulfinate sulfinolyase, a dibenzothiophene monooxygenase, and a NADH-FMN oxidoreductase.

In certain embodiments, the invention relates to a method, comprising the step of contacting any one of the aforementioned genetically engineered organisms with a substrate, wherein the substrate comprises a phosphorus-containing fraction and a non-phosphorus-containing fraction;

the phosphorus-containing fraction comprises, in an amount from about 10% by weight to about 100% by weight, a phosphorus-containing compound of any one of Formulas I-III;

the compound of formula I is

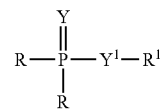

wherein, independently for each occurrence,
R is —H, alkyl, —OH, —OR$^2$, —SH, or —SR$^2$;
R$^1$ is —H, or alkyl;
Y is O or S;
Y$^1$ is O or S; and
R$^2$ is alkyl;
the compound of formula II is

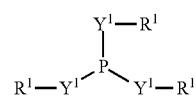

wherein, independently for each occurrence,
R$^1$ is —H, or alkyl; and
Y$^1$ is O or S;
the compound of formula III is

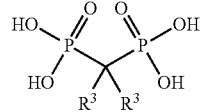

wherein, independently for each occurrence,
R$^3$ is —H, —OH, —OR$^4$, —SH, —SR$^4$, halo, alkyl, aryl, heteroaryl, aralkyl, or heteroaralkyl; and
R$^4$ is alkyl or aryl;
a native organism of the same species as the genetically engineered organism could not metabolize (i.e., use as a source of phosphorus) the phosphorus-containing compound; and the genetically engineered organism converts the substrate to a product.

In certain embodiments, the invention relates to a method, comprising the step of contacting any one of the aforementioned genetically engineered organisms with a substrate, wherein the substrate comprises a sulfur-containing fraction and a non-sulfur-containing fraction;

the sulfur-containing fraction comprises, in an amount from about 10% by weight to about 100% by weight, a sulfur-containing compound of any one of Formulas IV-XI;

the compound of formula IV is

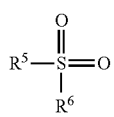

IV wherein, independently for each occurrence, $R^5$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(=O)—$R^7$;

$R^6$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(=O)—$R^7$; and $R^7$ is cycloalkyl, alkyl, or aryl, or any two $R^7$, taken together, form a 5- or 6-membered ring;

the compound of formula V, formula VI, or formula VII, is

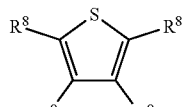

V

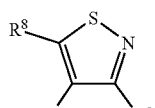

VI

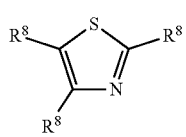

VII wherein, independently for each occurrence, $R^8$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(=O)—$R^7$;

$R^7$ is cycloalkyl, alkyl, or aryl, or any two $R^7$, taken together, form a 5- or 6-membered ring;

the compound of formula VIII, formula IX, or formula X is

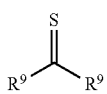

VIII

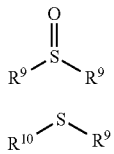

IX

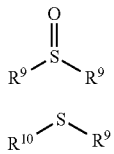

X wherein, independently for each occurrence, $R^9$ is —H, —OH, —$OR^7$, —SH, —$SR^7$, $R^7$, halo, alkyl, aryl, heteroaryl, aralkyl, heteroaralkyl, —$SO_2H$, —$NH_2$, —$NHR^7$, or —NH—C(=O)—$R^7$;

$R^7$ is cycloalkyl, alkyl, or aryl, or any two $R^7$, taken together, form a 5- or 6-membered ring;

$R^{10}$ is hydroxyalkyl, $R^9$, or —$(CH_2)_xR^9$; and x is 1, 2, 3, or 4;

the compound of formula XI is

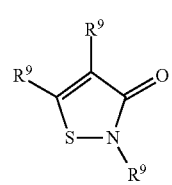

XI wherein, independently for each occurrence, $R^9$ is —H, —OH, —$OR^7$, —SH, —$SR^7$, $R^7$, halo, alkyl, aryl, heteroaryl, aralkyl, heteroaralkyl, —$SO_2H$, —$NH_2$, —$NHR^7$, or —NH—C(=O)—$R^7$; and $R^7$ is cycloalkyl, alkyl, or aryl, or any two $R^7$, taken together, form a 5- or 6-membered ring;

a native organism of the same species as the genetically engineered organism could not metabolize (i.e., use as a source of sulfur) the sulfur-containing compound; and the genetically engineered organism converts the substrate to a product.

In certain embodiments, the invention relates to a product made by any one of the aforementioned methods.

In certain embodiments, the invention relates to a recombinant vector comprising a gene operably linked to a promoter, wherein the gene encodes an enzyme; and the enzyme is NAD:phosphite oxidoreductase (phosphite dehydrogenase), glycerol-3-phosphate dehydrogenase (sn-glycerol 3-phosphate: NAD(+) oxidoreductase, EC 1.1.1.8), glyceraldehyde-3-phosphate dehydrogenase, an organophosphate degradation enzyme, a phosphodiesterase, a phospholipase, desulfurization enzyme, a dibenzothiophene-5,5-dioxide monooxygenase, a 2-hydroxybiphenyl-2-sulfinate sulfinolyase, a dibenzothiophene monooxygenase, or a NADH-FMN oxidoreductase.

BRIEF DESCRIPTION OF THE FIGURES

FIG. 1 depicts various DNA sequences of the invention (SEQ ID NOS 1-9, respectively, in order of appearance).

FIG. 2 tabulates various organisms of the invention and exemplary potential applications.

FIG. 3 tabulates various organisms of the invention and exemplary potential applications.

FIG. 4 tabulates various organophosphorus compounds useful as feedstocks in the invention, and the chemical formula of each compound.

FIG. 5 tabulates various organosulfur compounds useful as feedstocks in the invention, and the chemical formula of each compound.

FIG. 9 tabulates the sequence of pNC273 (SEQ ID NOS 10-11, respectively, in order of appearance).

FIG. 12 depicts the growth of NS435 with (a) phosphate (Pi), and (b) phosphite (Pt).

FIG. 14 depicts a plasmid map of pNC360.

FIG. 15 tabulates the sequence of pNC360 (SEQ ID NOS 12-13, respectively, in order of appearance).

FIG. 16 depicts growth of NS435 with different concentrations of hypophosphite.

FIG. 18 depicts a plasmid map of pNC351.

FIG. 19 tabulates the sequence of pNC351 (SEQ ID NO: 14).

DETAILED DESCRIPTION OF THE INVENTION

Overview

Figure 6:
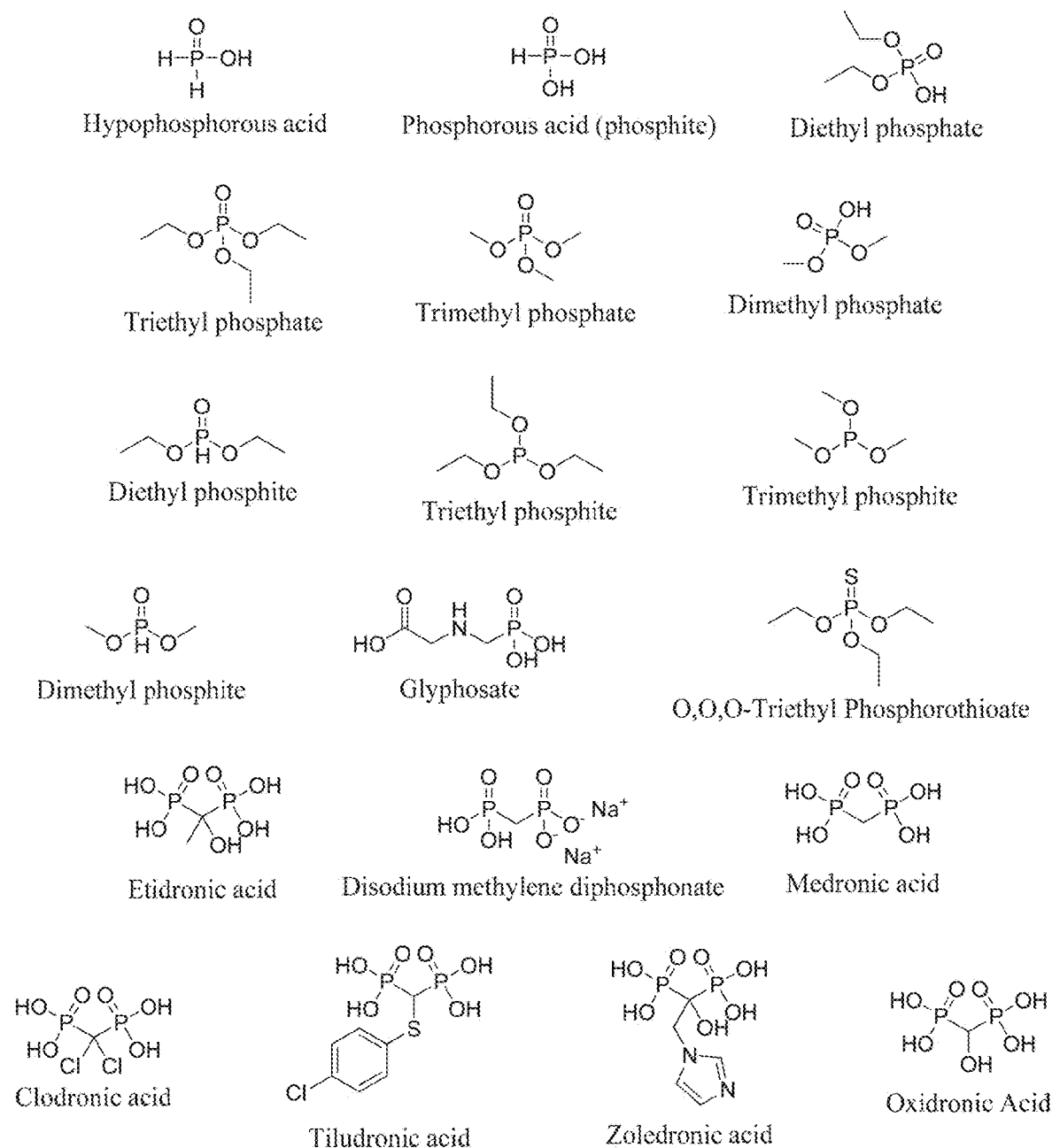
FIG. 6 depicts the names and structures of various organophosphorus compounds useful as feedstocks in the invention.
Figure 7:
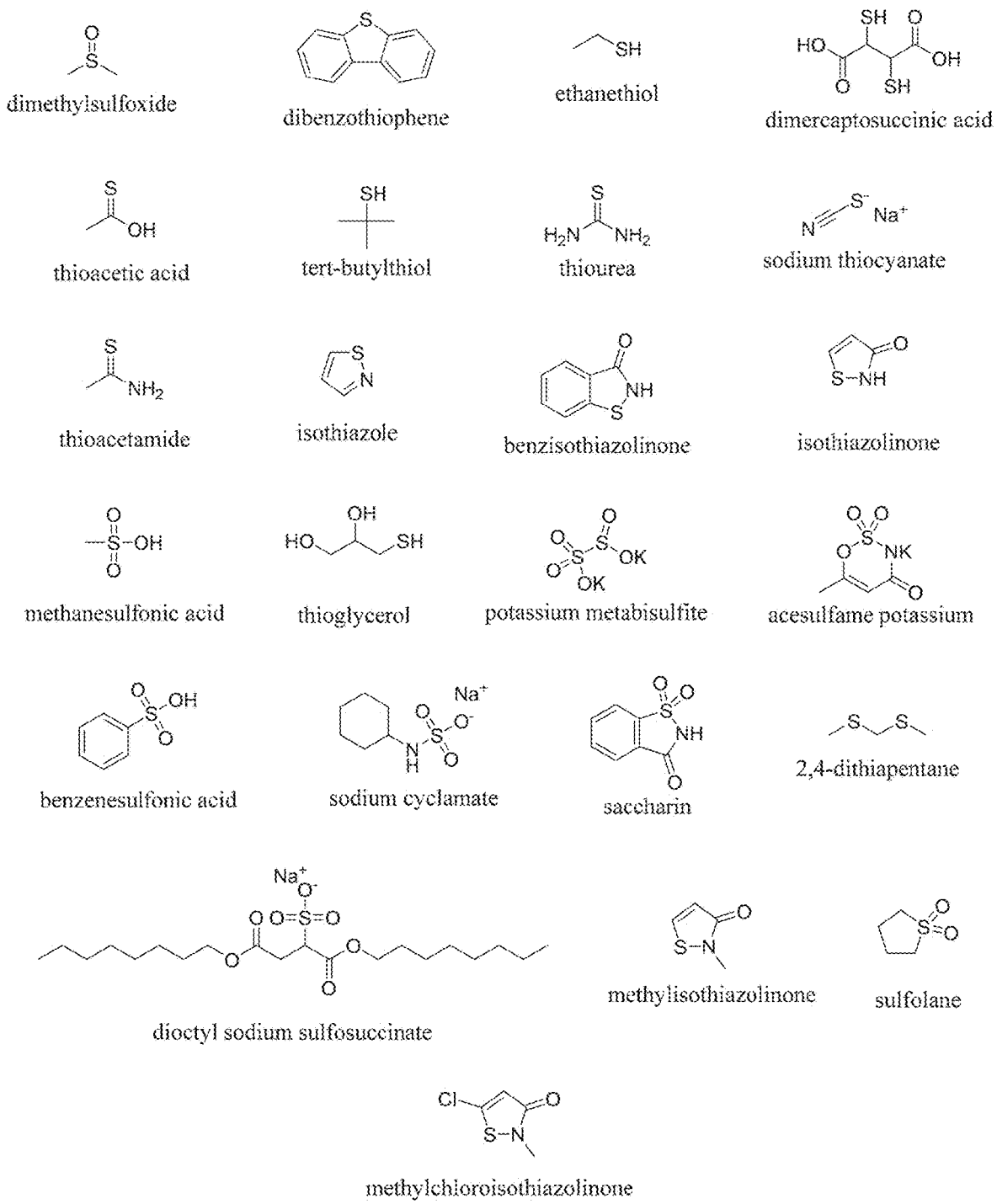
FIG. 7 depicts the names and structures of various organosulfur compounds useful as feedstocks in the invention.

In certain embodiments, the invention relates to a genetically engineered host organism, wherein the genetically engineered host organism has a non-native ability to obtain a growth-limiting nutrient from a complex substrate; and the complex substrate could not have been metabolized or used as a nutrient by the native host organism. In certain embodiments, the non-native ability will provide the organism with a significant competitive advantage, and provide a major barrier to the success of contaminants in a fermentation.

In certain embodiments, organisms generally contain only a small amount of phosphorus and sulfur (e.g., about 3% and about 1% by mass of the cell, respectively). So, in order to grow, organisms need less of these growth-limiting nutrients as compared to, for example, nitrogen.

In certain embodiments, the genetically engineered host organism is a bacterium, a yeast, a fungus, an algae, a mammalian cell, or an insect cell. In certain embodiments, the genetically engineered host organism is a bacterium or a yeast.

In certain embodiments, the invention relates to a method of using the above-mentioned genetically engineered host organism, comprising contacting the genetically engineered host organism with a modified cell culture medium. In certain embodiments, the invention relates to a method of using the above-mentioned genetically engineered host organism, comprising contacting the genetically engineered host organism with a modified cell culture medium, wherein the genetically engineered host organism converts the cell culture medium to a product. In certain embodiments, using this approach provides a unique and targeted manner to promote the growth of the desired genetically engineered host organism. In certain embodiments, the above-mentioned methods minimize the growth of contaminant organisms, provide a valuable competitive advantage, and allow management of production of a range of valuable products.

In certain embodiments, the inventive methods decrease or eliminate the need for use of prophylactic antibiotics in large scale yeast cultures. Avoiding unnecessary antibiotics is an important benefit due to emerging environmental considerations and societal pressures. Additionally, in certain embodiments, the technique can be applied to bacterial systems in which antibiotics may not be added. In certain embodiments, the technique can be applied to minimize the growth of wild yeast contaminants that are natively resistant to many commonly used antibiotics.

In certain embodiments, the genetically engineered host organism is a yeast; and the product is ethanol, isobutanol, lactic acid, succinic acid, erythritol, an isoprenoid, a lipid, and enzyme product, a bulk commodity chemical, or a high value specialty chemical.

In certain embodiments, the genetically engineered host organism is a bacterium; and the product is butanol, ethanol, isopropanol, 1,3-propanediol (PDO), 1,4-butanediol (BDO), succinic acid, itaconic acid, an enzyme product, a polyol, a protein product, a bulk commodity chemical, or a high value specialty chemical.

In certain embodiments, the inventive technology is applicable in the production of one or more commodities, fine chemicals, or pharmaceuticals.

Definitions

As used herein, the term "biomass" refers to a primarily carbohydrate-containing material. Biomass can also refer to a polysaccharide-containing material. It can also refer to a cellulose-, hemicellulose-, or lignocellulose-containing material. Biomass is commonly obtained from, for example, wood, plants, residue from agriculture or forestry, organic component of municipal and industrial wastes, primary sludges from paper manufacture, waste paper, waste wood (e.g., sawdust), agricultural residues such as corn husks, corn cobs, rice hulls, straw, bagasse, starch from corn, wheat oats, and barley, waste plant material from hard wood or beech bark, fiberboard industry waste water, bagasse pity, bagasse, molasses, post-fermentation liquor, furfural still residues, aqueous oak wood extracts, rice hull, oats residues, wood sugar slops, fir sawdust, naphtha, corncob furfural residue, cotton balls, rice, straw, soybean skin, soybean oil residue, corn husks, cotton stems, cottonseed hulls, starch, potatoes, sweet potatoes, lactose, waste wood pulping residues, sunflower seed husks, hexose sugars, pentose sugars, sucrose from sugar cane and sugar beets, corn syrup, hemp, and combinations of the above.

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed.

"Exogenous gene" is a nucleic acid that codes for the expression of an RNA and/or protein that has been introduced into a cell (e.g., by transformation/transfection), and is also referred to as a "transgene." A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Expression vector" or "expression construct" or "plasmid" or "recombinant DNA construct" is a vehicle for introducing a nucleic acid into a host cell. The nucleic acid can be one that has been generated via human intervention, including by recombinant means or direct chemical synthesis, with a series of specified nucleic acid elements that permit transcription and/or translation of a particular nucleic acid. The expression vector can be part of a plasmid, virus, or nucleic acid fragment, or other suitable vehicle. Typically, the expression vector includes a nucleic acid to be transcribed operably linked to a promoter.

"Inducible promoter" is a promoter that mediates transcription of an operably linked gene in response to a particular stimulus.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"Lysate" is a solution containing the contents of lysed cells.

"Lysis" is the breakage of the plasma membrane and optionally the cell wall of a biological organism sufficient to release at least some intracellular content, often by mechanical, viral or osmotic mechanisms that compromise its integrity.

"Lysing" is disrupting the cellular membrane and optionally the cell wall of a biological organism or cell sufficient to release at least some intracellular content.

"Osmotic shock" is the rupture of cells in a solution following a sudden reduction in osmotic pressure. Osmotic shock is sometimes induced to release cellular components of such cells into a solution.

The terms "plasmid", "vector" and "cassette" refer to an extra chromosomal element often carrying genes that are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements, in addition to the foreign gene, that facilitate transformation of a particular host cell. "Expression cassette" refers to a specific vector containing a foreign gene and having elements in addition to the foreign gene that allow for enhanced expression of that gene in a foreign host.

"Promoter" is a nucleic acid control sequence that directs transcription of a nucleic acid. As used herein, a promoter includes necessary nucleic acid sequences near the start site of transcription. A promoter also optionally includes distal enhancer or repressor elements, which can be located as much as several thousand base pairs from the start site of transcription.

"Recombinant" is a cell, nucleic acid, protein, or vector, which has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

"Sonication" is a process of disrupting biological materials, such as a cell, by use of sound wave energy.

"Transformation" refers to the transfer of a nucleic acid fragment into a host organism or the genome of a host organism, resulting in genetically stable inheritance. Host organisms containing the transformed nucleic acid fragments are referred to as "recombinant", "transgenic" or "transformed" organisms. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

Microbe Engineering

A. Overview

In certain embodiments of the invention, a microorganism is genetically modified to improve or provide de novo growth characteristics on a variety of feedstock materials.

Genes and gene products may be introduced into microbial host cells. Suitable host cells for expression of the genes and nucleic acid molecules are microbial hosts that can be found broadly within the fungal or bacterial families and which grow over a wide range of temperature, pH values, and solvent tolerances.

Microbial expression systems and expression vectors containing regulatory sequences that direct high level expression of foreign proteins are well known to those skilled in the art. Any of these could be used to construct chimeric genes to produce the any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and the aforementioned starting parent strain as a host can be transformed with the resulting plasmid. This approach can increase the copy number of each of the genes encoding the enzymes and, as a result, the activities of these enzymes can be increased. The plasmid is not particularly limited so long as it can autonomously replicate in the microorganism.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene harboring transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (see for example Molecular Cloning: A Laboratory Manual, Sambrook et al. (3d edition, 2001, Cold Spring Harbor Press; and U.S. Pat. No. 4,683,202 (incorporated by reference)). Alternatively, elements can be generated synthetically using known methods (see for example Gene. 1995 Oct. 16; 164(1):49-53).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding genomic homologous sequences.

The ability to carry out homologous recombination in a host organism has many practical implications for what can be carried out at the molecular genetic level and is useful in the generation of an oleaginous microbe that can produced tailored oils. By its very nature homologous recombination is a precise gene targeting event, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from heterologous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements such as promoters/UTRs to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, and thus affecting the desired change in metabolism of the host cell. Homologous recombination provides a powerful means to manipulate the host genome resulting in gene targeting, gene conversion, gene deletion, gene duplication, gene inversion and exchanging gene expression regulatory elements, such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transformation of microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

This subsection is divided into subsections. Subsection 1 describes control sequences typically contained on vectors as well as novel control sequences provided by the present invention. Subsection 2 describes genes typically contained in vectors as well as novel codon optimization methods and genes prepared using them provided by the invention.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for expression of an exogenous gene in a microbe contains a coding sequence for a desired gene product (for example, a selectable marker, or an enzyme) in operable linkage with a promoter active in microalgae. Alternatively, if the vector does not contain a promoter in operable linkage with the coding sequence of interest, the coding sequence can be transformed into the cells such that it becomes operably linked to an endogenous promoter at the point of vector integration.

The promoter used to express an exogenous gene can be the promoter naturally linked to that gene or can be a heterologous promoter.

A promoter can generally be characterized as either constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of phosphorus or sulfur in culture media, etc. Suitable promoters can activate transcription of an essentially silent gene or upregulate, preferably substantially, transcription of an operably linked gene that is transcribed at a low level.

Inclusion of termination region control sequence is optional, and if employed, then the choice is be primarily one of convenience, as the termination region is relatively interchangeable. The termination region may be native to the transcriptional initiation region (the promoter), may be native to the DNA sequence of interest, or may be obtainable from another source. See, for example, Chen and Orozco, Nucleic Acids Res. (1988) 16:8411.

2. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the heterologous vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the heterologous mRNA resulting in ribosomal stalling and termination and possible instability of the transgenic mRNA.

D. Expression of Two or More Exogenous Genes

Further, a genetically engineered microorganism may comprise and express more than one exogenous gene. One or more genes can be expressed using an inducible promoter, which allows the relative timing of expression of these genes to be controlled. Expression of the two or more exogenous genes may be under control of the same inducible promoter or under control of different inducible promoters. In the latter situation, expression of a first exogenous gene can be induced for a first period of time (during which expression of a second exogenous gene may or may not be induced) and expression of a second or further exogenous gene can be induced for a second period of time (during which expression of a first exogenous gene may or may not be induced). Provided herein are vectors and methods for engineering microbes to grow on non-traditional growth media.

E. Transformation

Cells can be transformed by any suitable technique including, e.g., biolistics, electroporation, glass bead transformation and silicon carbide whisker transformation. Any convenient technique for introducing a transgene into a microorganism can be employed in the present invention. Transformation can be achieved by, for example, the method of D. M. Morrison (Methods in Enzymology 68, 326 (1979)), the method by increasing permeability of recipient cells for DNA with calcium chloride (Mandel, M. and Higa, A., J. Mol. Biol., 53, 159 (1970)), or the like.

Examples of expression of transgenes in oleaginous yeast (e.g., *Yarrowia lipolytica*) can be found in the literature (see, for example, Bordes et al., J Microbiol Methods, June 27 (2007)). Examples of expression of exogenous genes in bacteria such as *E. coli* are well known; see for example Molecular Cloning: A Laboratory Manual, Sambrook et al. (3d edition, 2001, Cold Spring Harbor Press).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to an endogenous promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (see for example Protist 2004 December; 155(4):381-93). The transformed cells can be optionally selected based upon the ability to grow in the presence of the antibiotic or other selectable marker under conditions in which cells lacking the resistance cassette would not grow.

Phosphorus-Containing Compounds in Feedstocks

In certain embodiments, the invention relates to use of an atypical phosphorus-containing feedstock comprising, consisting essentially of, or consisting of a phosphorus-containing compound of any one of Formulas I-III. In certain embodiments, a non-genetically engineered organism, i.e., a native organism, could not metabolize (i.e., use as a source of phosphorus) the phosphorus-containing compounds in the feedstock.

In certain embodiments, the invention relates to any one of the aforementioned phosphorus-containing feedstocks, wherein the phosphorus-containing compound is a compound of formula I or a salt thereof:

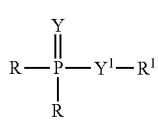

I wherein, independently for each occurrence,
R is —H, alkyl, —OH, —OR$^2$, —SH, or —SR$^2$;
R$^1$ is —H, or alkyl;
Y is O or S;
Y$^1$ is O or S; and
R$^2$ is alkyl.

In certain embodiments, the invention relates to any one of the aforementioned phosphorus-containing feedstocks, wherein the phosphorus-containing compound is a compound of formula II or a salt thereof:

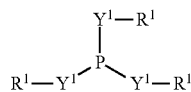

II wherein, independently for each occurrence,
R$^1$ is —H, or alkyl; and
Y$^1$ is O or S.

In certain embodiments, the invention relates to any one of the aforementioned phosphorus-containing feedstocks, wherein the phosphorus-containing compound is a compound of formula III or a salt thereof:

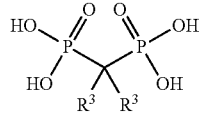

III wherein, independently for each occurrence,
R$^3$ is —H, —OH, —OR$^4$, —SH, —SR$^4$, halo, alkyl, aryl, heteroaryl, aralkyl, or heteroaralkyl; and
R$^4$ is alkyl or aryl.

In certain embodiments, the invention relates to any one of the aforementioned phosphorus-containing feedstocks, wherein the phosphorus-containing compound is selected from the group consisting of:

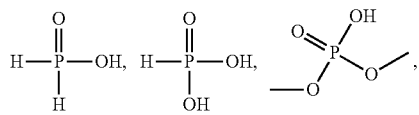

-continued

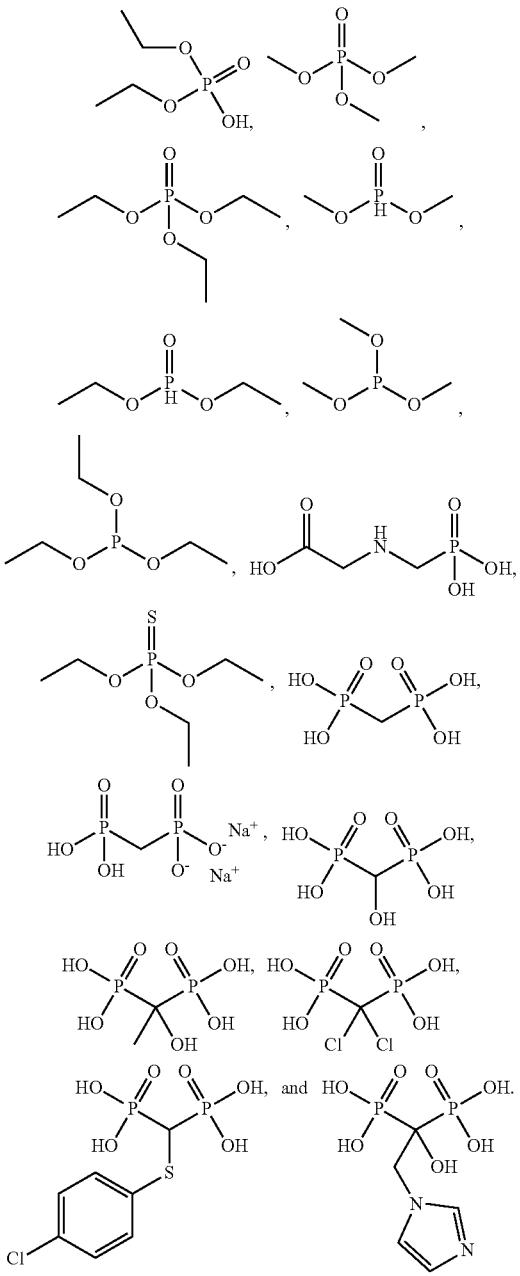

Sulfur-Containing Compounds in Feedstocks

In certain embodiments, the invention relates to use of an atypical sulfur-containing feedstock comprising, consisting essentially of, or consisting of a sulfur-containing compound of any one of Formulas IV-XI. In certain embodiments, a non-genetically engineered organism, i.e., a native organism, could not metabolize (i.e., use as a source of sulfur) the sulfur-containing compounds in the feedstock.

In certain embodiments, the invention relates to any one of the aforementioned sulfur-containing feedstocks, wherein the sulfur-containing compound is a compound of formula IV or a salt thereof:

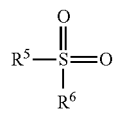
IV wherein, independently for each occurrence,
$R^5$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(=O)—$R^7$;
$R^6$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(=O)—$R^7$; and
$R^7$ is cycloalkyl, alkyl, or aryl, or any two $R^7$, taken together, form a 5- or 6-membered ring.

In certain embodiments, the invention relates to any one of the aforementioned sulfur-containing feedstocks, wherein the sulfur-containing compound is a compound of formula V, formula VI, or formula VII, or a salt thereof:

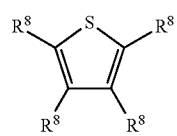
V

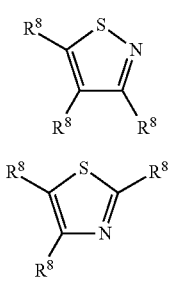
VI

VII wherein, independently for each occurrence,
$R^8$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(=O)—$R^7$;
$R^7$ is cycloalkyl, alkyl, or aryl, or any two $R^7$, taken together, form a 5- or 6-membered ring.

In certain embodiments, the invention relates to any one of the aforementioned sulfur-containing feedstocks, wherein the sulfur-containing compound is a compound of formula VIII, formula IX, or formula X or a salt thereof:

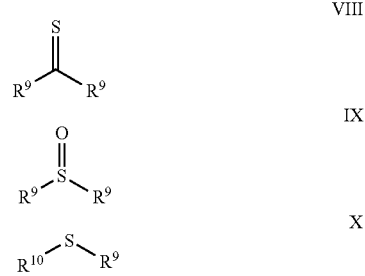
VIII

IX

X wherein, independently for each occurrence.
$R^9$ is —H, —OH, —$OR^7$, —SH, —$SR^7$, $R^7$, halo, alkyl, aryl, heteroaryl, aralkyl, heteroaralkyl, —$SO_2H$, —$NH_2$, —$NHR^7$, or —NH—C(=O)—$R^7$;
$R^7$ is cycloalkyl, alkyl, or aryl, or any two $R^7$, taken together, form a 5- or 6-membered ring;
$R^{10}$ is hydroxyalkyl, $R^9$, or —$(CH_2)_xR^9$; and
$x$ is 1, 2, 3, or 4.

In certain embodiments, the invention relates to any one of the aforementioned sulfur-containing feedstocks, wherein the sulfur-containing compound is a compound of formula XI or a salt thereof:

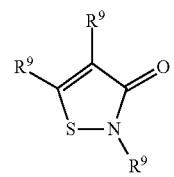
XI wherein, independently for each occurrence,
$R^9$ is —H, —OH, —$OR^7$, —SH, —$SR^7$, $R^7$, halo, alkyl, aryl, heteroaryl, aralkyl, heteroaralkyl, —$SO_2H$, —$NH_2$, —$NHR^7$, or —NH—C(=O)—$R^7$; and
$R^7$ is cycloalkyl, alkyl, or aryl, or any two $R^7$, taken together, form a 5- or 6-membered ring.

In certain embodiments, the invention relates to any one of the aforementioned sulfur-containing feedstocks, wherein the sulfur-containing compound is selected from the group consisting of:

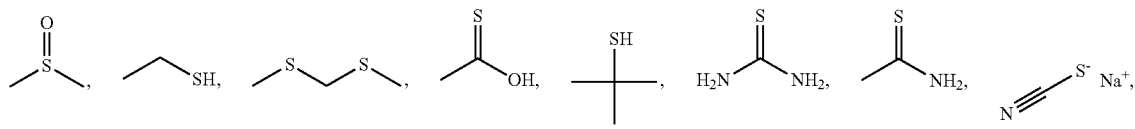

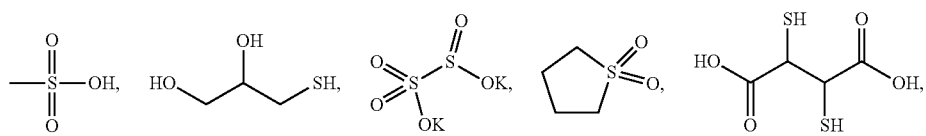

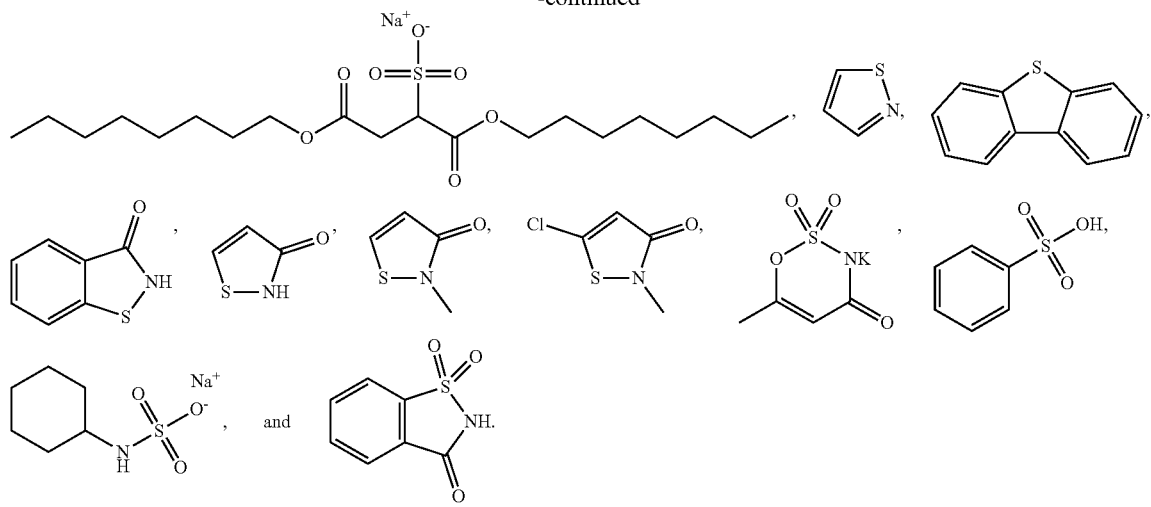

Exemplary Isolated Nucleic Acid Molecules and Vectors

In certain embodiments, the invention relates to an isolated nucleic acid molecule, wherein the nucleic acid molecule encodes an enzyme that provides the organism with the ability to assimilate a phosphorus source or a sulfur source that otherwise would not have been accessible to the native organism; and the enzyme is NAD:phosphite oxidoreductase (phosphite dehydrogenase), glycerol-3-phosphate dehydrogenase (sn-glycerol 3-phosphate: NAD(+) oxidoreductase, EC 1.1.1.8), glyceraldehyde-3-phosphate dehydrogenase, an organophosphate degradation enzyme, a phosphodiesterase, a phospholipase, desulfurization enzyme, a dibenzothiophene-5,5-dioxide monooxygenase, a 2-hydroxybiphenyl-2-sulfinate sulfinolyase, a dibenzothiophene monooxygenase, or a NADH-FMN oxidoreductase.

In certain embodiments, the invention relates to an isolated nucleic acid molecule, wherein the nucleic acid molecule is selected from the group consisting of Delftia acidoorans phosphodiesterase pdeA, Enterobacter aerogenes updABDE gpdQ, Flavobacterium opdA without periplasmic leader sequence, Pseudomonas aeruginosa PAO phoA, Pseudomonas monteilii C11 hocA, Pseudomonas stutzeri WM88 htxABCDEFHGIJKLMN, Pseudomonas stutzeri WM88 ptxABCDE, Rhodococcus dszD, and Rhodococcus dszABC.

In certain embodiments, the invention relates to an isolated nucleic acid molecule comprising any one of the sequences disclosed herein. In certain embodiments, the invention relates to an isolated nucleic acid molecule having at least 85% sequence homology with any one of the sequences disclosed herein. In certain embodiments, the invention relates to an isolated nucleic acid molecule having at least 90% sequence homology with any one of the sequences disclosed herein. In certain embodiments, the invention relates to an isolated nucleic acid molecule having at least 95% sequence homology with any one of the sequences disclosed herein. In certain embodiments, the invention relates to an isolated nucleic acid molecule having at least 99% sequence homology with any one of the sequences disclosed herein. In certain embodiments, the invention relates to an isolated nucleic acid molecule having any one of the sequences disclosed herein.

A recombinant vector comprising any one of the aforementioned nucleic acid molecules operably linked to a promoter.

In certain embodiments, the invention relates to a recombinant vector comprising any one of the sequences disclosed herein. In certain embodiments, the invention relates to a recombinant vector having at least 85% sequence homology with any one of the sequences disclosed herein. In certain embodiments, the invention relates to a recombinant vector having at least 90% sequence homology with any one of the sequences disclosed herein. In certain embodiments, the invention relates to a recombinant vector having at least 95% sequence homology with any one of the sequences disclosed herein. In certain embodiments, the invention relates to a recombinant vector having at least 99% sequence homology with any one of the sequences disclosed herein.

Exemplary Genetically Engineered Organisms of the Invention

In certain embodiments, the invention relates to a genetically engineered organism, wherein the genetically engineered organism has been transformed by a nucleic acid molecule or a recombinant vector comprising any one of the sequences disclosed herein. In certain embodiments, the nucleic acid molecule or recombinant vector has at least 85% sequence homology with any one of the sequences disclosed herein. In certain embodiments, the nucleic acid molecule or recombinant vector has at least 90% sequence homology with any one of the sequences disclosed herein. In certain embodiments, the nucleic acid molecule or recombinant vector has at least 95% sequence homology with any one of the sequences disclosed herein. In certain embodiments, the nucleic acid molecule or recombinant vector has at least 99% sequence homology with any one of the sequences disclosed herein. In certain embodiments, the invention relates to a genetically engineered organism, wherein the genetically engineered organism has been transformed by a nucleic acid molecule or a recombinant vector having any one of the sequences disclosed herein.

In certain embodiments, the invention relates to a genetically engineered organism, wherein the genetically engineered organism has been transformed by a nucleic acid molecule; the nucleic acid molecule comprises a non-native gene; and the non-native gene encodes for a non-native enzyme selected from the group consisting of NAD:phosphite oxidoreductase (phosphite dehydrogenase), glycerol-3-phosphate dehydrogenase (sn-glycerol 3-phosphate: NAD(+) oxidoreductase, EC 1.1.1.8), glyceraldehyde-3- phosphate dehydrogenase, an organophosphate degradation enzyme, a phosphodiesterase, a phospholipase, desulfurization enzyme, a dibenzothiophene-5,5-dioxide monooxygenase, a 2-hydroxybiphenyl-2-sulfinate sulfinolyase, a dibenzothiophene monooxygenase, and a NADH-FMN oxidoreductase.

In certain embodiments, the invention relates to any one of the aforementioned genetically engineered organisms, wherein the non-native gene is selected from the group consisting of dszABC, dszA, dszABCD, dszB, dszC, dszD, gpdQ, hocA, htxA, htxABCDEFHGIJKLMN, htxB, htxC, htxD, htxE, htxF, htxG, htxH, htxI, htxJ, htxK, htxL, htxM, htxN, opdA, ophA, pde, pdeA, phoA, ptxABCDE, ptxD, ugpA, ugpAECB, ugpB, ugpC, ugpE, updA, updABDE, updB, updD, and updE.

Any organism may be used as a source of the non-native gene, as long as the organisms has the desired enzymatic activity The non-native gene can each be obtained from chromosomal DNA of any one of the aforementioned microorganisms by isolating a DNA fragment complementing auxotrophy of a variant strain lacking the enzymatic activity. Alternatively, if the nucleotide sequence of these gene of the organism has already been elucidated (Biochemistry, Vol. 22, pp. 5243-5249, 1983; J. Biochem. Vol. 95, pp. 909-916, 1984; Gene, Vol. 27, pp. 193-199, 1984; Microbiology, Vol. 140, pp. 1817-1828, 1994; Mol. Gene Genet. Vol. 218, pp. 330-339, 1989; and Molecular Microbiology, Vol. 6, pp 317-326, 1992), the genes can be obtained by PCR using primers synthesized based on each of the elucidated nucleotide sequences, and the chromosome DNA as a template.

In certain embodiments, the invention relates to any one of the aforementioned genetically engineered organisms, wherein the non-native gene is selected from the group consisting of Delftia acidoorans phosphodiesterase pdeA, *Enterobacter aerogenes* updABDE gpdQ, *Flavobacterium* opdA without periplasmic leader sequence, *Pseudomonas aeruginosa* PAO1 phoA, *Pseudomonas monteilii* C11 hocA, *Pseudomonas stutzeri* WM88 htxABCDEFHGIJKLMN, *Pseudomonas stutzeri* WM88 ptxABCDE, *Rhodococcus* dszD, and *Rhodococcus* dszABC.

In certain embodiments, the invention relates to any one of the aforementioned genetically engineered organisms, wherein the genetically engineered organism is a species of the genus *Acetobacter, Acinetobacter, Alcaligenes, Arxula, Aspergillus, Aurantiochytrium, Bacillus, Candida, Chlamydomonas, Clostridium, Corynebacterium, Escherichia, Hansenula, Isochrysis, Kluyveromyces, Lactococcus, Micrococcus, Nannochloropsis, Ogataea, Paracoccus, Pavlova, Penicillium, Pichia, Pseudomonas, Rhizopus, Rhodosporidium, Rhodotorula, Saccharomyces, Schizosaccharomyces, Streptococcus, Streptomyces, Synechococcus, Tetraselmis, Thermoanaerobacter, Thermoanaerobacterium, Trichoderma, Xanthaomonas,* or *Yarrowia.*

In certain embodiments, the invention relates to any one of the aforementioned genetically engineered organisms, wherein the genetically engineered organism is a species of the genus *Aspergillus, Bacillus, Chlamydomonas, Corynebacterium, Escherichia, Hansenula, Kluyveromyces, Saccharomyces, Synechococcus,* or *Yarrowia.*

In certain embodiments, the invention relates to any one of the aforementioned genetically engineered organisms, wherein the genetically engineered organism is selected from the group consisting of *Acetobacter, Acinetobacter calcoaceticus, Alcaligenes eutropha, Arxula adeninivorans, Aspergillus nidulans, Aspergillus niger, Aspergillus orzyae, Aspergillus terreus, Aurantiochytrium* spp., *Bacillus licheniforms, Bacillus methanolicus, Bacillus stearothermophilus, Bacillus subtilis, Candida utilis, Chlamydomonas reinhardtii, Clostridium acetobutylicum, Clostridium thermocellum, Corynebacterium glutamicum, Escherichia coli, Hansenula polymorpha, Isochrysis* spp., *Kluyveromyces lactis, Kluyveromyces marxianus, Lactococcus lactis, Micrococcus lysodeikticus, Nannochloropsis* spp., *Ogataea, Paracoccus denitrificans, Pavlova* spp., *Penicillium chrysogenum, Pichia guilliermondii, Pichia pastoris, Pichia stipitis, Pseudononas putida, Rhizopus* spp., *Rhodosporidium* spp., *Rhodotorula* spp., *Saccharomyces cerevisiae, Schizosaccharomyces pombe, Streptococcus lactis, Streptomyces, Synechococcus elongalus, Tetraselmis* spp., *Thermoanaerobacter* spp., *Thermoanaerobacterium* spp., *Trichoderma reesei, Xanthaomonas campestris,* or *Yarrowia lipolytica.*

In certain embodiments, the invention relates to any one of the aforementioned genetically engineered organisms, wherein the genetically engineered organism is selected from the group consisting of *Aspergillus niger, Bacillus subtilis, Chlamydomonas reinhardtii, Corynebacterium glutamicum, Escherichia coli, Hansenula polymorpha, Kluyveromyces marxianus, Saccharomyces cerevisiae, Synechococcus elongatus,* or *Yarrowia lipolytica.* Exemplary Methods of the Invention In certain embodiments, the invention relates to a method, comprising the step of contacting any one of the aforementioned genetically engineered organisms with a substrate, wherein the substrate comprises a phosphorus-containing fraction and a non-phosphorus-containing fraction;

the phosphorus-containing fraction comprises, in an amount from about 10% by weight to about 100% by weight, a phosphorus-containing compound of any one of Formulas I-III;

a native organism of the same species as the genetically engineered organism could not metabolize (i.e., use as a source of phosphorus) the phosphorus-containing compound; and the genetically engineered organism converts the substrate to a product.

In certain embodiments, the invention relates to any one of the aforementioned methods, wherein the phosphorus-containing compounds have a low molecular weight. In certain embodiments, the invention relates to any one of the aforementioned methods, wherein the phosphorus-containing compounds have a molecular weight between about 30 Da and about 800 Da. In certain embodiments, the invention relates to any one of the aforementioned methods, wherein the phosphorus-containing compounds have a molecular weight between about 40 Da and about 600 Da. In certain embodiments, the invention relates to any one of the aforementioned methods, wherein the phosphorus-containing compounds have a molecular weight of about 40 Da, about 50 Da, about 60 Da, about 70 Da, about 80 Da, about 90 Da, about 100 Da, about 110 Da, about 120 Da, about 130 Da, about 140 Da, about 150 Da, about 160 Da, about 170 Da, about 180 Da, about 190 Da, about 200 Da, about 220 Da, about 240 Da, about 260 Da, about 280 Da, about 300 Da, about 320 Da, about 340 Da, about 360 Da, about 380 Da, about 400 Da, about 420 Da, about 440 Da, about 460 Da, about 480 Da, about 500 Da, about 520 Da, about 540 Da, bout 560 Da, about 580 Da, or about 600 Da.

In certain embodiments, the invention relates to any one of the aforementioned methods, wherein the phosphorus-containing compounds have less than 12 carbon atoms. In certain embodiments, the invention relates to any one of the aforementioned methods, wherein the phosphorus-containing compounds have less than 8 carbon atoms. In certain embodiments, the invention relates to any one of the aforementioned methods, wherein the phosphorus-containing compounds have 1, 2, 3, 4, 5, 6, or 7 carbon atoms.

In certain embodiments, the invention relates to any one of the aforementioned methods, wherein the phosphorus-containing compounds are between about 8% and about 75% phosphorus by weight. In certain embodiments, the invention relates to any one of the aforementioned methods, wherein the phosphorus-containing compounds are between about 15% and about 47% phosphorus by weight. In certain embodiments, the invention relates to any one of the aforementioned methods, wherein the phosphorus-containing compounds are about 8%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, or about 74% phosphorus by weight.

In certain embodiments, the invention relates to any one of the aforementioned methods, wherein the phosphorus-containing compounds have an octanol-water partition coefficient (log P) less than about 5. In certain embodiments, the invention relates to any one of the aforementioned methods, wherein the phosphorus-containing compounds have an octanol-water partition coefficient (log P) from about −0.5 to about 5. In certain embodiments, the invention relates to any one of the aforementioned methods, wherein the phosphorus-containing compounds have an octanol-water partition coefficient (log P) of about −0.5, about 0, about 0.5, about 1, about 1.5, about 2, about 2.5, about 3, about 3.5, about 4, or about 4.5.

In certain embodiments, the invention relates to any one of the aforementioned methods, wherein the phosphorus-containing compounds are soluble in water at about 20° C. at a concentration of between about 0.01 g/L to about 1000 g/L. In certain embodiments, the invention relates to any one of the aforementioned methods, wherein the phosphorus-containing compounds are soluble in water at about 20° C. at a concentration of about 0.01 g/L, about 0.05 g/L, about 0.1 g/L, about 0.5 g/L, about 1 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

In certain embodiments, the invention relates to any one of the aforementioned methods, wherein the phosphorus-containing compounds move through the cell membrane by passive transport. Passive transport includes diffusion, facilitated diffusion, and filtration.

In certain embodiments, the invention relates to any one of the aforementioned methods, wherein the phosphorus-containing compounds move through the cell membrane by active transport, such as, for example, via an ATP-Binding Cassette (ABC) transporter or other known transmembrane transporter.

In certain embodiments, the invention relates to any one of the aforementioned methods, wherein the phosphorus-containing compounds are transported through the cell membrane.

In certain embodiments, the invention relates to any one of the aforementioned methods, wherein the phosphorus-containing compounds are substantially non-biocidal.

In certain embodiments, the invention relates to any one of the aforementioned methods, wherein the phosphorus-containing compounds are substantially biodegradable.

In certain embodiments, the invention relates to any one of the aforementioned methods, wherein the phosphorus-containing fraction comprises the phosphorus-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate, wherein the substrate comprises a phosphorus-containing fraction and a non-phosphorus-containing fraction;

the phosphorus-containing fraction comprises, in an amount from about 10% by weight to about 100% by weight, a phosphorus-containing compound selected from the group consisting of:

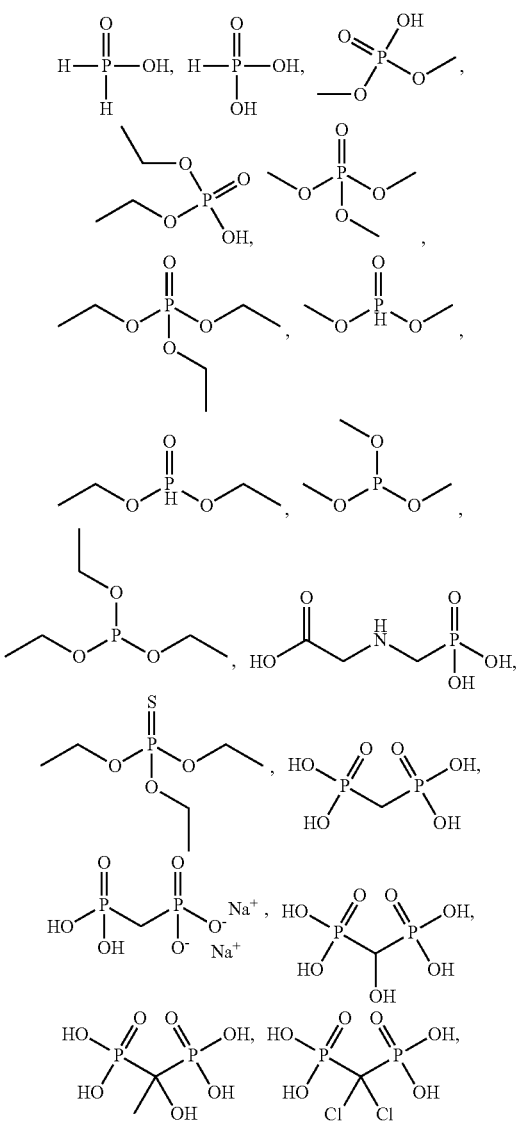

-continued

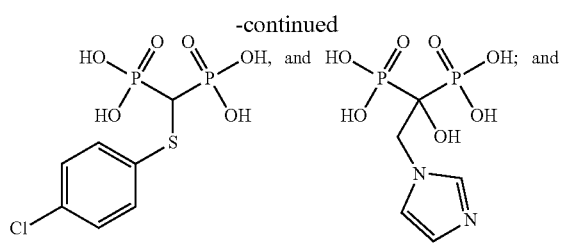

the genetically engineered organism converts the substrate to a product.

In certain embodiments, the invention relates to any one of the aforementioned methods, wherein the phosphorus-containing fraction comprises the phosphorus-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate, wherein the substrate comprises a phosphorus-containing fraction and a non-phosphorus-containing fraction;

the phosphorus-containing fraction consists essentially of a phosphorus-containing compound selected from the group consisting of

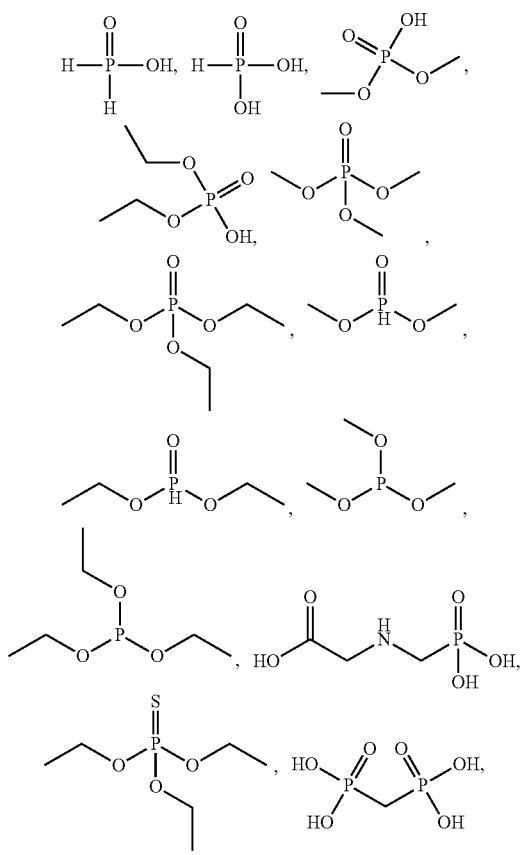

-continued

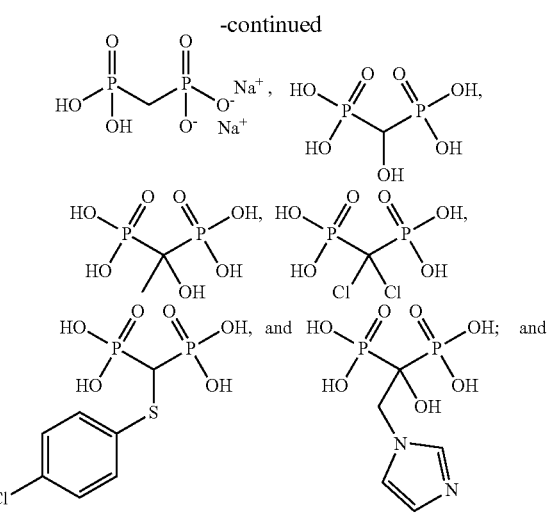

the genetically engineered organism converts the substrate to a product.

In certain embodiments, the invention relates to a method comprising the step of contacting any one of the aforementioned genetically engineered organisms with a substrate, wherein the substrate consists of a phosphorus-containing fraction and a non-phosphorus-containing fraction;

the phosphorus-containing fraction consists of a phosphorus-containing compound selected from the group consisting of

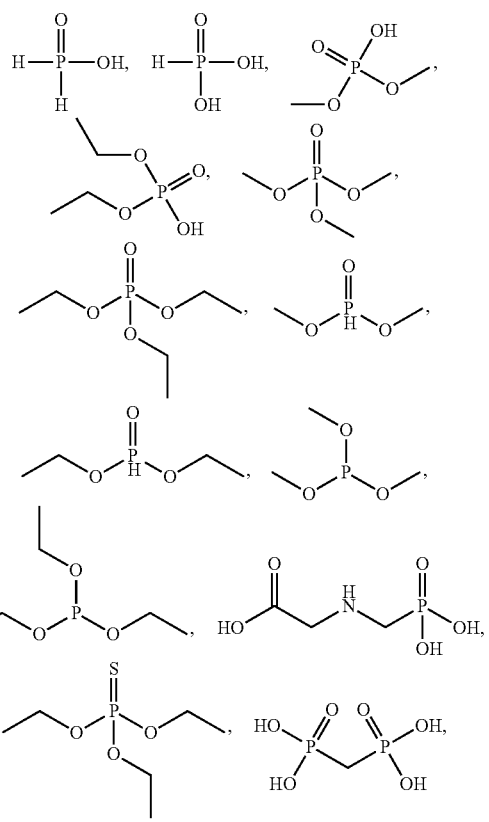

-continued

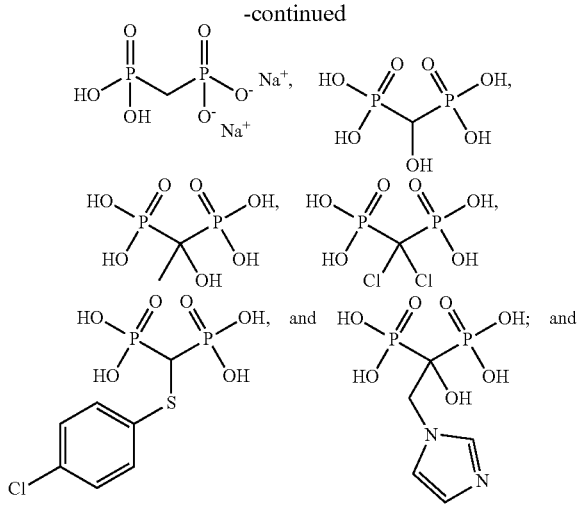

the genetically engineered organism converts the substrate to a product.

In certain embodiments, the invention relates to any one of the aforementioned methods, wherein the genetically engineered organism sequesters the product.

In certain embodiments, the invention relates to any one of the aforementioned methods, wherein a plurality of genetically engineered organisms is used.

In certain embodiments, the invention relates to any one of the aforementioned methods, wherein the substrate does not comprise an antibiotic.

In certain embodiments, the invention relates to any one of the aforementioned methods, wherein a non-genetically engineered organism, i.e., a native organism, could not metabolize (i.e., use as a source of phosphorus) the phosphorus-containing compound.

In certain embodiments, the invention relates to any one of the aforementioned methods, wherein the substrate comprises lignocellulosic material, glucose, xylose, sucrose, acetic acid, formic acid, lactic acid, butyric acid, a free fatty acid, dextrose, glycerol, fructose, lactose, galactose, mannose, rhamnose, or arabinose, or a combination thereof.

In certain embodiments, the invention relates to any one of the aforementioned methods, wherein the pH of the substrate is from about 2.5 to about 10.

In certain embodiments, the invention relates to any one of the aforementioned methods, wherein the genetically engineered organism is contacted with the substrate at a temperature of from about 15° C. to about 80° C.

In certain embodiments, the invention relates to any one of the aforementioned methods, wherein the genetically engineered organism is contacted with the substrate over a time period of from about 6 h to about 10 d.

In certain embodiments, the invention relates to any one of the aforementioned methods, wherein the genetically engineered organism is contacted with the substrate in a fermentor.

In certain embodiments, the invention relates to any one of the aforementioned methods, wherein the genetically engineered organism is contacted with the substrate in an industrial-size fermentor.

In certain embodiments, the invention relates to any one of the aforementioned methods, wherein a plurality of genetically engineered organisms is contacted with a plurality of substrates in a plurality of fermentors, wherein the plurality of fermentors are arranged in parallel.

In certain embodiments, the invention relates to any one of the aforementioned methods, wherein the product is ethanol, isopropanol, lactic acid, an isoprenoid, a lipid, a high-value specialty chemical, butanol, 1,3-propanediol, 1,4-butanediol, succinic acid, an expressed protein product, an enzyme product, a polyol, a pharmaceutical product, itaconic acid, or a high value specialty chemical.

In certain embodiments, the invention relates to a method, comprising the step of contacting any one of the aforementioned genetically engineered organisms with a substrate, wherein the substrate comprises a sulfur-containing fraction and a non-sulfur-containing fraction;

the sulfur-containing fraction comprises, in an amount from about 10% by weight to about 100% by weight, a sulfur-containing compound of any one of Formulas IV-XI;

a native organism of the same species as the genetically engineered organism could not metabolize (i.e., use as a source of sulfur) the sulfur-containing compound; and the genetically engineered organism converts the substrate to a product.

In certain embodiments, the invention relates to any one of the aforementioned methods, wherein the sulfur-containing compounds have a low molecular weight. In certain embodiments, the invention relates to any one of the aforementioned methods, wherein the sulfur-containing compounds have a molecular weight between about 30 Da and about 800 Da. In certain embodiments, the invention relates to any one of the aforementioned methods, wherein the sulfur-containing compounds have a molecular weight between about 40 Da and about 600 Da. In certain embodiments, the invention relates to any one of the aforementioned methods, wherein the sulfur-containing compounds have a molecular weight of about 40 Da, about 50 Da, about 60 Da, about 70 Da, about 80 Da, about 90 Da, about 100 Da, about 110 Da, about 120 Da, about 130 Da, about 140 Da, about 150 Da, about 160 Da, about 170 Da, about 180 Da, about 190 Da, about 200 Da, about 220 Da, about 240 Da, about 260 Da, about 280 Da, about 300 Da, about 320 Da, about 340 Da, about 360 Da, about 380 Da, about 400 Da, about 420 Da, about 440 Da, about 460 Da, about 480 Da, about 500 Da, about 520 Da, about 540 Da, bout 560 Da, about 580 Da, or about 600 Da.

In certain embodiments, the invention relates to any one of the aforementioned methods, wherein the sulfur-containing compounds have less than 12 carbon atoms. In certain embodiments, the invention relates to any one of the aforementioned methods, wherein the sulfur-containing compounds have less than 8 carbon atoms. In certain embodiments, the invention relates to any one of the aforementioned methods, wherein the sulfur-containing compounds have 1, 2, 3, 4, 5, 6, or 7 carbon atoms.

In certain embodiments, the invention relates to any one of the aforementioned methods, wherein the sulfur-containing compounds have an octanol-water partition coefficient (log P) less than about 5. In certain embodiments, the invention relates to any one of the aforementioned methods, wherein the sulfur-containing compounds have an octanol-water partition coefficient (log P) from about −0.5 to about 5. In certain embodiments, the invention relates to any one of the aforementioned methods, wherein the sulfur-containing compounds have an octanol-water partition coefficient (log P) of about −0.5, about 0, about 0.5, about 1, about 1.5, about 2, about 2.5, about 3, about 3.5, about 4, or about 4.5.

In certain embodiments, the invention relates to any one of the aforementioned methods, wherein the sulfur-containing compounds are soluble in water at about 20° C. at a concentration of between about 0.01 g/L to about 1000 g/L.

In certain embodiments, the invention relates to any one of the aforementioned methods, wherein the sulfur-containing compounds are soluble in water at about 20° C. at a concentration of about 0.01 g/L, about 0.05 g/L, about 0.1 g/L, about 0.5 g/L, about 1 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

In certain embodiments, the invention relates to any one of the aforementioned methods, wherein the sulfur-containing compounds move through the cell membrane by passive transport. Passive transport includes diffusion, facilitated diffusion, and filtration.

In certain embodiments, the invention relates to any one of the aforementioned methods, wherein the sulfur-containing compounds move through the cell membrane by active transport, such as, for example, via an ATP-Binding Cassette (ABC) transporter or other known transmembrane transporter.

In certain embodiments, the invention relates to any one of the aforementioned methods, wherein the sulfur-containing compounds are transported through the cell membrane.

In certain embodiments, the invention relates to any one of the aforementioned methods, wherein the sulfur-containing compounds are substantially non-biocidal.

In certain embodiments, the invention relates to any one of the aforementioned methods, wherein the sulfur-containing compounds are substantially biodegradable.

In certain embodiments, the invention relates to any one of the aforementioned methods, wherein the sulfur-containing fraction comprises the phosphorus-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate, wherein the substrate comprises a sulfur-containing fraction and a non-phosphorus-containing fraction;

the sulfur-containing fraction comprises, in an amount from about 10% by weight to about 100% by weight, a sulfur-containing compound selected from the group consisting of:

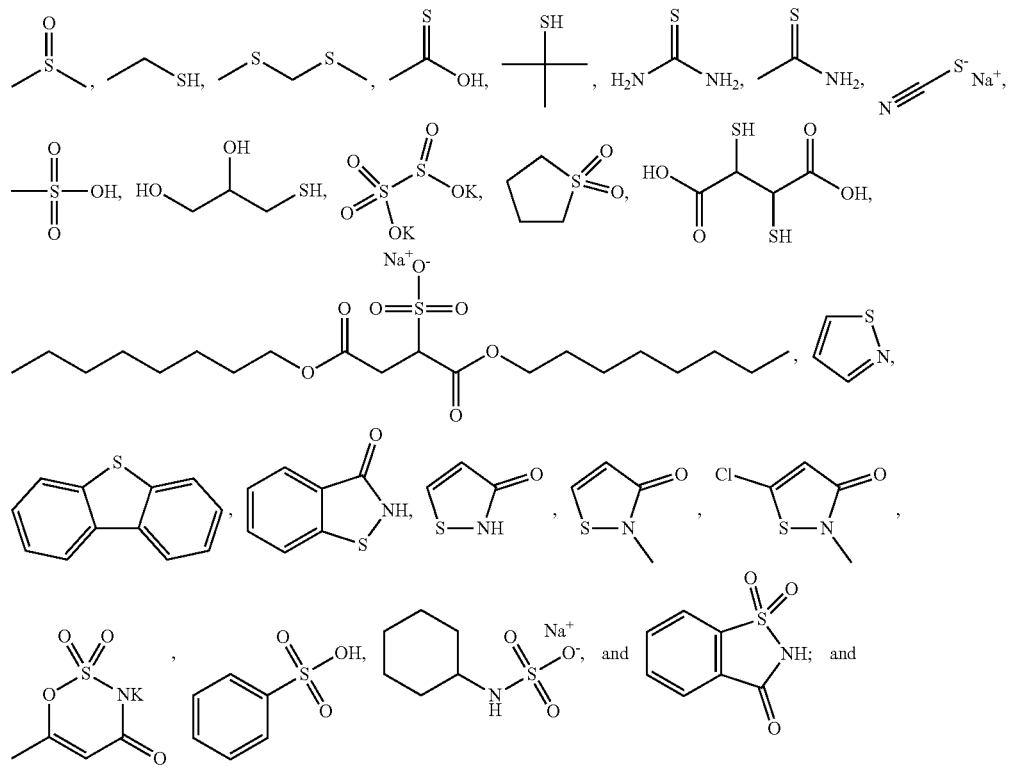

the genetically engineered organism converts the substrate to a product.

In certain embodiments, the invention relates to any one of the aforementioned methods, wherein the sulfur-containing fraction comprises the sulfur-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate, wherein the substrate comprises a sulfur-containing fraction and a non-sulfur-containing fraction;

the sulfur-containing fraction consists essentially of a sulfur-containing compound selected from the group consisting of

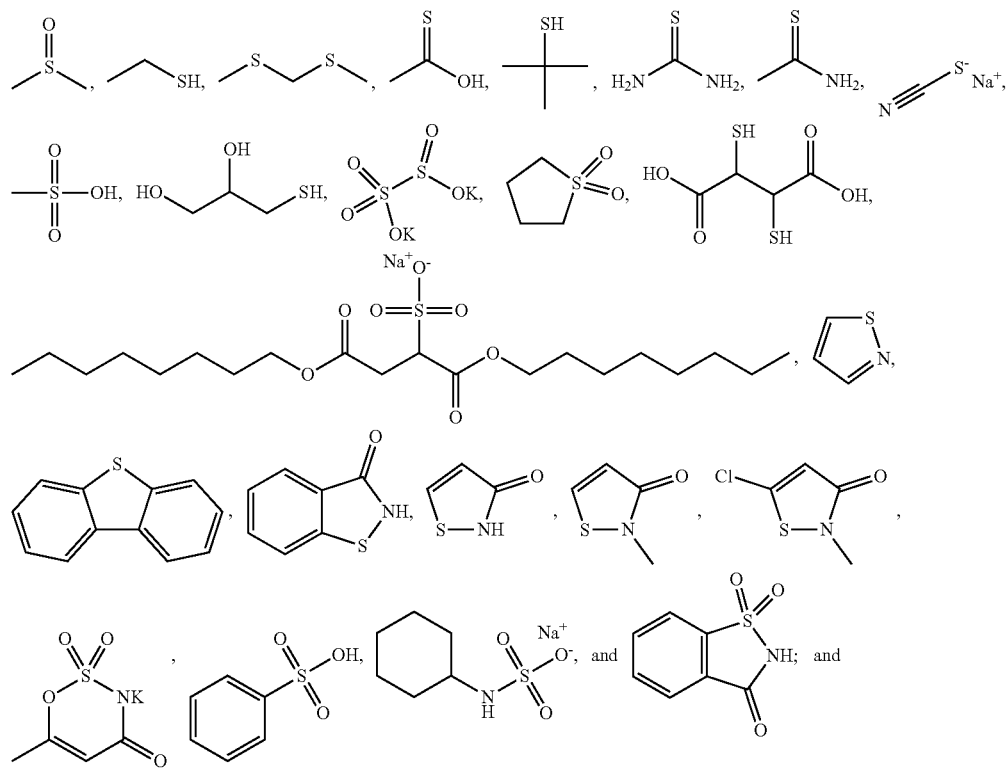

the genetically engineered organism converts the substrate to a product.

In certain embodiments, the invention relates to a method comprising the step of contacting any one of the aforementioned genetically engineered organisms with a substrate, wherein the substrate consists of a sulfur-containing fraction and a non-sulfur-containing fraction;

the sulfur-containing fraction consists of a sulfur-containing compound selected from the group consisting of

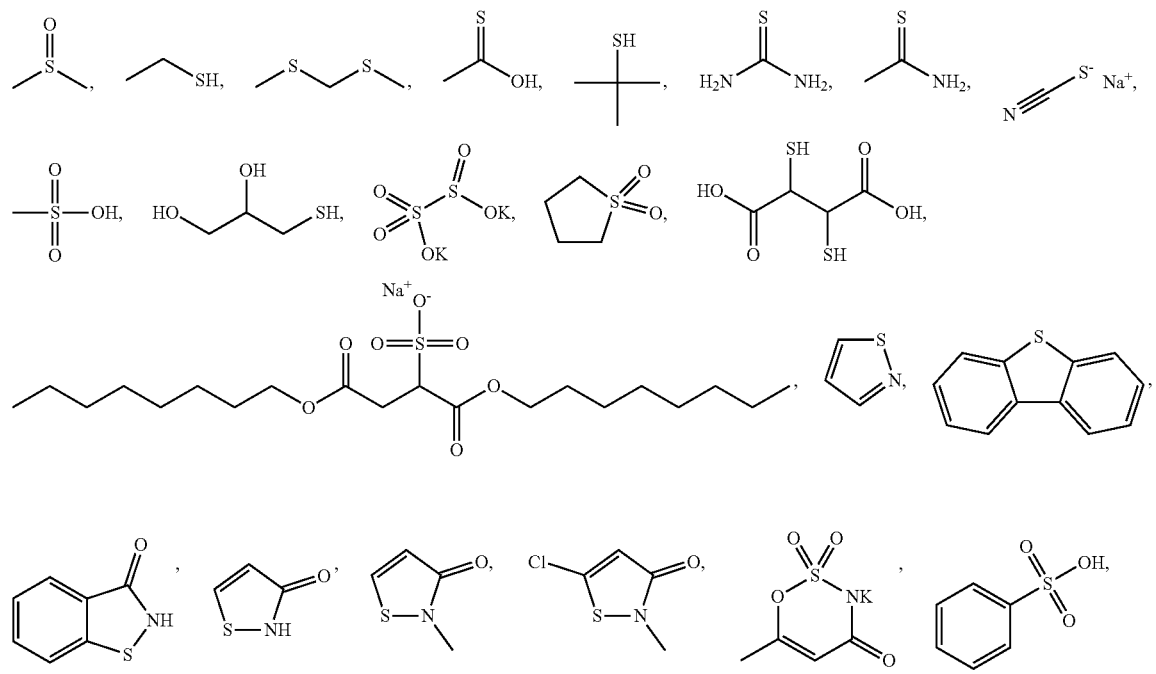

-continued

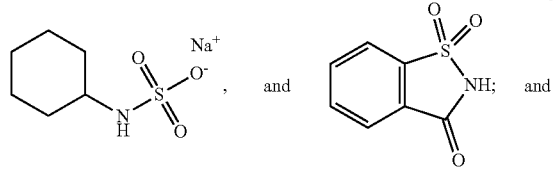

the genetically engineered organism converts the substrate to a product.

In certain embodiments, the invention relates to any one of the aforementioned methods, wherein the genetically engineered organism sequesters the product.

In certain embodiments, the invention relates to any one of the aforementioned methods, wherein a plurality of genetically engineered organisms is used.

In certain embodiments, the invention relates to any one of the aforementioned methods, wherein the substrate does not comprise an antibiotic.

In certain embodiments, the invention relates to any one of the aforementioned methods, wherein a non-genetically engineered organism, i.e., a native organism, could not metabolize (i.e., use as a source of sulfur) the sulfur-containing compound.

In certain embodiments, the invention relates to any one of the aforementioned methods, wherein the substrate comprises lignocellulosic material, glucose, xylose, sucrose, acetic acid, formic acid, lactic acid, butyric acid, a free fatty acid, dextrose, glycerol, fructose, lactose, galactose, mannose, rhamnose, or arabinose, or a combination thereof.

In certain embodiments, the invention relates to any one of the aforementioned methods, wherein the pH of the substrate is from about 2.5 to about 10.

In certain embodiments, the invention relates to any one of the aforementioned methods, wherein the genetically engineered organism is contacted with the substrate at a temperature of from about 15° C. to about 80° C.

In certain embodiments, the invention relates to any one of the aforementioned methods, wherein the genetically engineered organism is contacted with the substrate over a time period of from about 6 h to about 10 d.

In certain embodiments, the invention relates to any one of the aforementioned methods, wherein the genetically engineered organism is contacted with the substrate in a fermentor.

In certain embodiments, the invention relates to any one of the aforementioned methods, wherein the genetically engineered organism is contacted with the substrate in an industrial-size fermentor.

In certain embodiments, the invention relates to any one of the aforementioned methods, wherein a plurality of genetically engineered organisms is contacted with a plurality of substrates in a plurality of fermentors, wherein the plurality of fermentors are arranged in parallel.

In certain embodiments, the invention relates to any one of the aforementioned methods, wherein the product is ethanol, isopropanol, lactic acid, an isoprenoid, a lipid, a high-value specialty chemical, butanol, 1,3-propanediol, 1,4-butanediol, succinic acid, an expressed protein product, an enzyme product, a polyol, a pharmaceutical product, itaconic acid, or a high value specialty chemical.

Exemplary Products

In certain embodiments, the invention relates to a product made by any one of the aforementioned methods.

EXEMPLIFICATION

The following examples are provided to illustrate the invention. It will be understood, however, that the specific details given in each example have been selected for purpose of illustration and are not to be construed as limiting the scope of the invention. Generally, the experiments were conducted under similar conditions unless noted.

Example 1—Use of Phosphite as Phosphorus Source for ptxD-Expressing *Yarrowia lipolytica*

A) Expression of Bacterial ptxD in *Yarrowia lipolytica*

Figure 8:
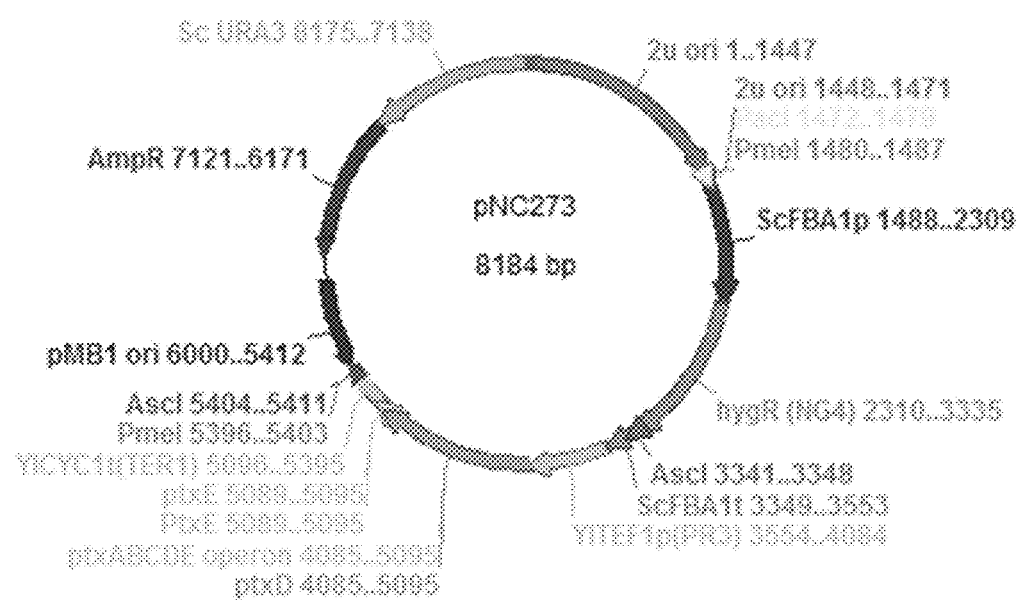
FIG. 8 depicts a plasmid map of vector pNC273, which was used to construct strain NS392.

Vector pNC273 was used to construct strain NS392. See FIG. 8.

Vector pNC273 was restriction digested with enzyme PmcI, and the linear fragment containing hygR and ptxD under control of the *Y. lipolytica* TEF1 promoter and *Y. lipolytica* CYC1 terminator. Transformation was via standard protocols (Chen D. C. et al., Appl Microbiol Biotechnol. 1997 August; 48(2):232-5). See FIG. 9.

B) Competition Experiment Between ptxD-Expressing *Y. lipolytica* and Wildtype *S. cerevisiae*

Figure 10:
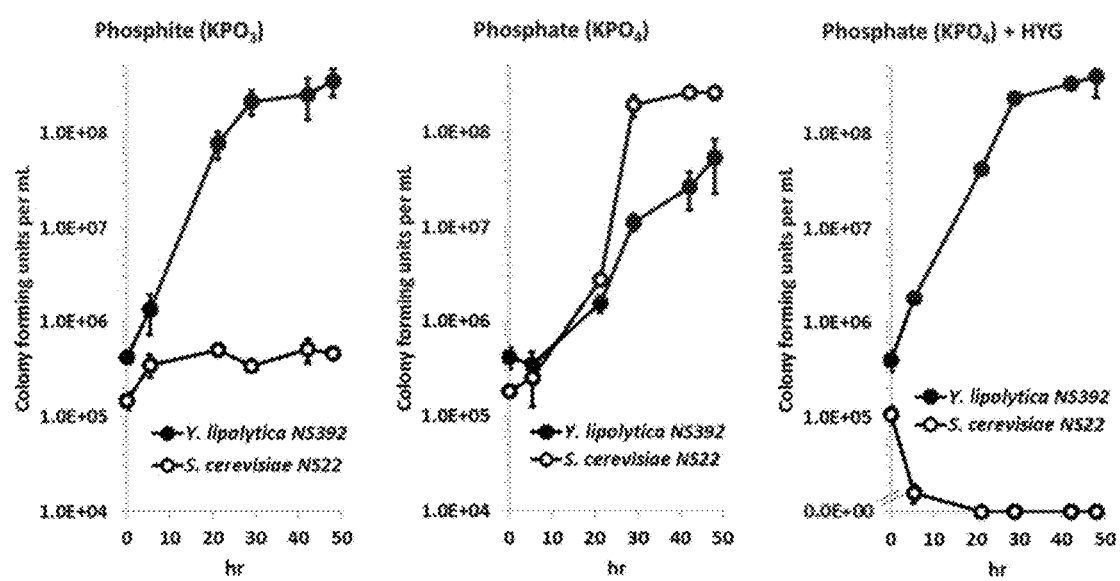
FIG. 10 depicts the growth of two organisms (modified *Y. lipolytica* NS392 (solid circles) and wild-type *S. cerevisiae* NS22 (open circles)) on three different growth media: potassium phosphite as the sole phosphorus source (left), potassium phosphate as the sole phosphorus source (middle), and potassium phosphate plus hygromyic as a control condition.

*Yarrowia lipolytica* NS392 (ptxD $HYG^R$) and *Saccharomyces cerevisiae* NS22 (wildtype, $HYG^S$) were pre-cultured overnight in defined medium with 10 mM potassium phosphate (NS22) or 10 mM potassium phosphite (NS392). After pre-culture growth, cells were washed twice in water and added to three experimental media conditions at an $OD_{600\ nm}$ of 0.06 for NS22 and 0.6 for NS392. The three media conditions were with potassium phosphite as sole phosphorus source, potassium phosphate as sole phosphorus source, and with potassium phosphate plus hygromycin as a control condition to select to $HYG^R$ *Y. lipolytica* and against $HYG^S$ *S. cerevisiae*. See FIG. 10.

Defined Media Composition

| Macro nutrients | g/L |
| --- | --- |
| Glucose monohydrate | 44 |
| Urea | 3 |
| $MgSO_4 \cdot 7H_2O$ | 0.5 |
| Potassium hydrogen phthalate | 1 |
| Disodium phthalate | 4.25 |
| Vitamins | mg/L |
| Biotin | 0.05 |
| Thiamine | 1.0 |
| D-Pantothenic acid | 1.0 |
| Nicotinic acid | 1.0 |
| myo-inositol | 25 |
| Pyridoxine | 1.0 |
| p-Aminobenzoic acid | 0.2 |
| Micro elements | mg/L |
| EDTA | 15 |
| $CaCl_2 \cdot 6H_2O$ | 7.5 |

-continued

| | |
|---|---|
| $(NH_4)_2FeSO_4 \cdot 6H_2O$ | 3.0 |
| $CuSO_4 \cdot 5H_2O$ | 0.2 |
| $ZnSO_4 \cdot 7H_2O$ | 1.0 |
| $MnSO_4 \cdot H_2O$ | 0.5 |
| $Na_2MoO_4 \cdot 2H_2O$ | 0.2 |
| To this base medium, add either | g/L |
| $KH_2PO_4$ | 1.3 |
| $KH_2PO_3$ | 1.2 |

Example 2—Use of Hypophosphite as Phosphorus Source for ptxD-Expressing *Yarrowia lipolytica*

*Y. lipolytica* expressing ptxD also grows on hypophosphite. As shown in Table 1, NS18, wildtype *Y. lipolytica*, does not grow on phosphite or hypophosphite, and neither does NS184, a *Y. lipolytica* strain engineered for increased lipid production. NS324 (created by transforming NS18 with pNC273) and NS392 (created by transforming NS184 with pNC273) are able to grow on both phosphite and hypophosphite. However, *E. coli* W3110, which has the native ability to convert phosphite to phosphate, is unable to grow on hypophosphite. Additionally, W3110 was unable to grow on hypophosphite pre-incubated in defined yeast medium, suggesting that hypophosphite is not degraded to phosphite by incubation in medium alone. Additional measurements of growth with phosphate, phosphite, and hypophosphite are shown below in Table 2 for strain NS324.

TABLE 1

| Phosphate Source | NS18 | NS184 | NS324(ptxD) | NS392(ptxD) | W3110 |
|---|---|---|---|---|---|
| 0 Phosphate | − | − | − | − | − |
| 10 mM Phosphate | + | + | + | + | + |
| 10 mM Phosphite | − | − | + | + | + |
| 10 mM Hypophosphite | − | − | + | + | − |

TABLE 2

| NS324/Phosphate source | 0 hr $OD_{600}$ | 19 hr $OD_{600}$ | 28 hr $OD_{600}$ | 44 hr $OD_{600}$ |
|---|---|---|---|---|
| 0 Pi | 0.021 | 0.034 | 0.00 | 0.001 |
| 0.2 Mm Pi | 0.021 | 0.812 | 4.68 | 6.86 |
| 2 mM Pi | 0.021 | 0.736 | 4.92 | 5.04 |
| 20 mM Pi | 0.021 | 0.804 | 5.50 | 5.98 |
| 0.2 mM Pt | 0.021 | 0.704 | 2.71 | 5.43 |
| 0.4 mM Pt | 0.023 | 0.568 | 2.57 | 5.01 |
| 1 mM Pt | 0.023 | 0.7 | 3.77 | 6.2 |
| 2 mM Pt | 0.022 | 0.568 | 3.08 | 5.9 |
| 4 mM Pt | 0.023 | 0.68 | 3.23 | 4.45 |
| 10 mM Pt | 0.023 | 0.696 | 2.94 | 4.36 |
| 20 mM Pt | 0.023 | 0.840 | 3.69 | 5.24 |
| 0.2 mM Hpt | 0.021 | 0.008 | 0.21 | 0.454 |
| 0.4 mM Hpt | 0.021 | 0.04 | 0.71 | 0.732 |
| 1 mM Hpt | 0.021 | 0.24 | 1.13 | 1.66 |
| 2 mM Hpt | 0.023 | 0.712 | 1.96 | 2.99 |
| 4 mM Hpt | 0.023 | 0.896 | 3.24 | 5.36 |
| 10 mM Hpt | 0.023 | 0.632 | 2.17 | 3.17 |
| 20 mM Hpt | 0.022 | 0.452 | 1.26 | 1.72 |

Example 3—Use of Phosphite as Phosphorus Source for ptxD-Expressing *Saccharomyces cerevisiae*

Figure 11:
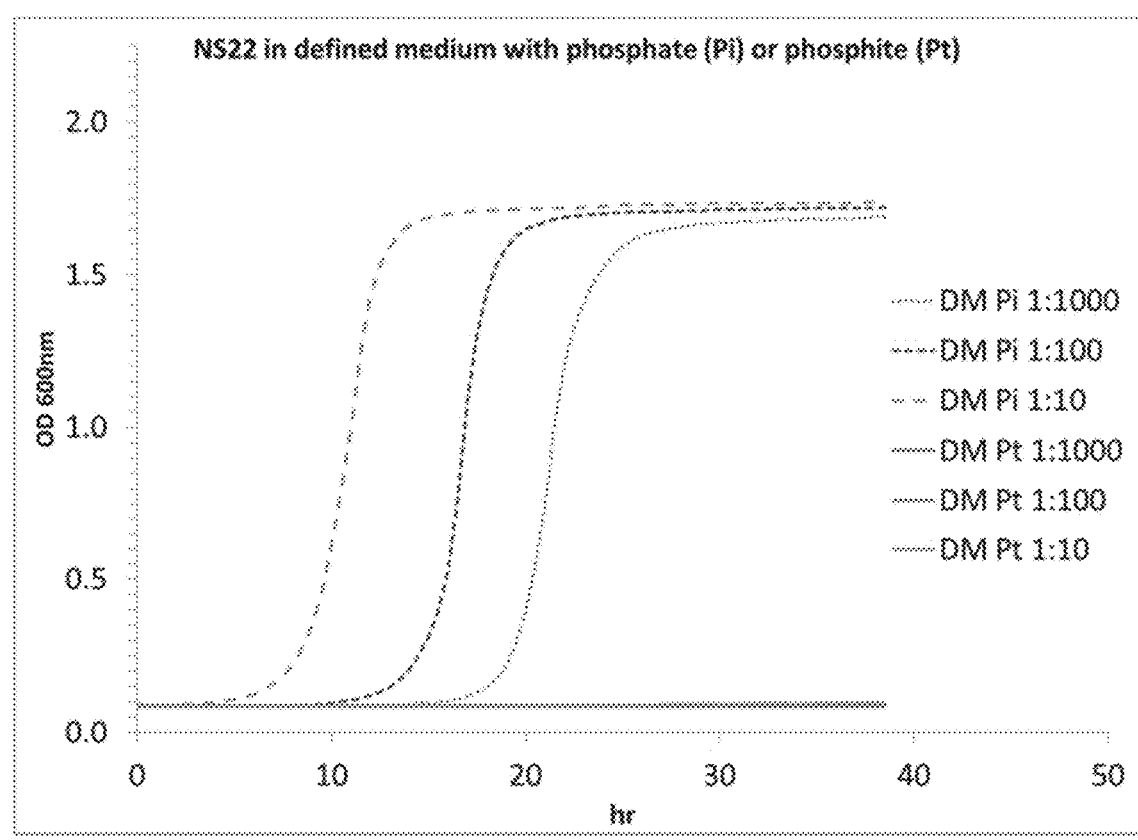
FIG. 11 depicts the growth of NS22, wildtype *S. cerevisiae*, with phosphate or phosphite as phosphorus source in defined medium. Different 10-fold serial dilutions of the inocula were made to observe the possible occurrence of a lag phase.
Figure 13:
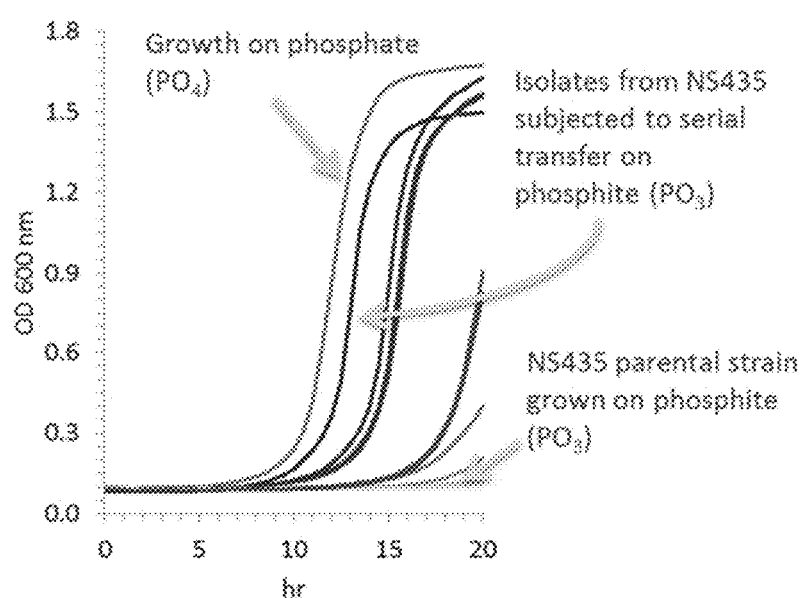
FIG. 13 depicts the growth of isolates after serial transfer of NS435 in phosphite media.
Figure 17:
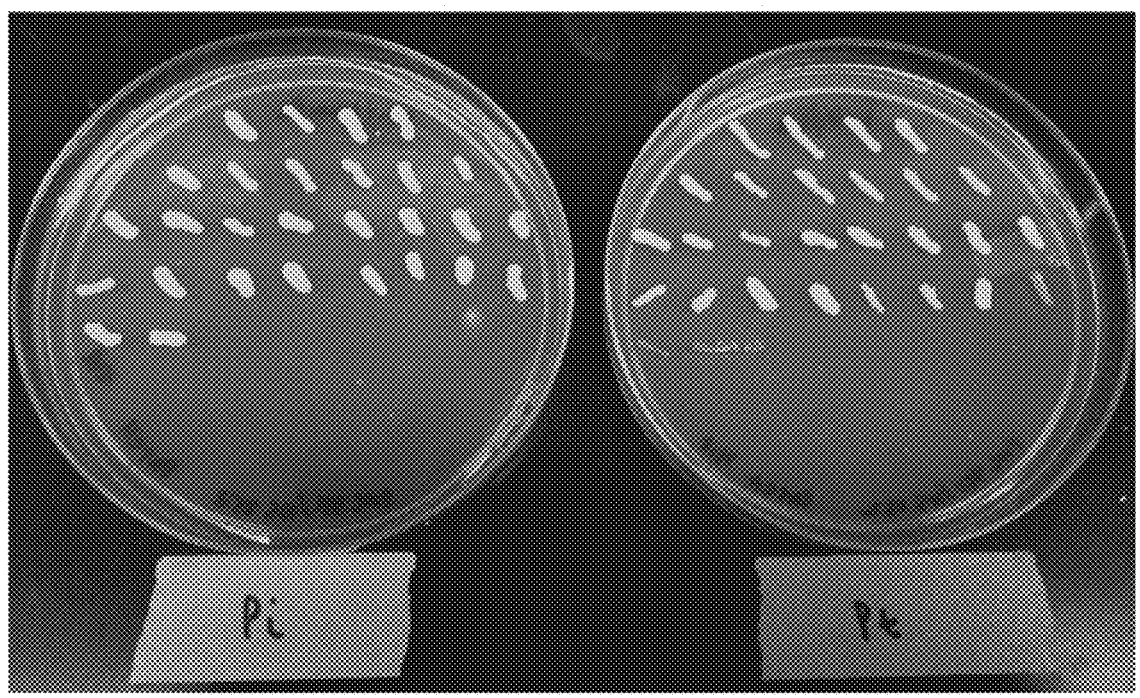
FIG. 17 depicts NS252+ptxD transformants patched on defined medium agar plates with phosphate (Pi, left) or phosphite (Pt, right) as phosphorus source. Untransformed NS252 was also patched.

Wildtype *S. cerevisiae* was shown to not grow with phosphite supplied as phosphorus source (FIG. 11). Plasmid pNC273, containing ptxD under control of the *Y. lipolytica* TEF1 promoter, was transformed into *S. cerevisiae* NS22. Despite evidence of functional ptxD expression in *Y. lipolytica* with the same vector, and prior evidence of *Y. lipolytica* TEF1 promoter function in *S. cerevisiae* expressing an antibiotic resistance marker, no growth was seen with this transformed construct with phosphite as phosphorus source. Subsequently, ptxD was placed under control of the *S. cerevisiae* TEF1 promoter in vector pNC360. With this transformed strain, NS435, growth was observed with phosphite as phosphorus source, although a lag phase was present. (FIG. 12). To reduce the lag phase, NS435 was serial transferred 10 times in 5 mL defined medium with 1 mM potassium phosphite replacing potassium phosphate. Serial transfers were performed after cultures reached stationary phase, with approximately 70 generations occurring during the transfers. From the final serial passage whole culture was streaked to single colonies on phosphite containing solid agar medium. Several of these isolates were grown in defined medium with 1 mM phosphate, washed, and evaluated in medium with 10 mM phosphite for growth rate and lag phase (FIG. 13). Of these, a top performing isolate was retained and designated NS473.

Example 4—Use of Hypophosphite as Phosphorus Source for ptxD-Expressing *Saccharomyces cerevisiae*

*S. cerevisiae* functionally expressing ptxD also surprisingly grows on hypophosphite. As shown in Table 3, NS22, wildtype *S. cerevisiae*, does not grow on phosphite or hypophosphite. NS435 (created by transforming NS22 with pNC360) is able to grow on both phosphite and hypophosphite. However, *E. coli* W3110, which has the native ability to convert phosphite to phosphate, is unable to grow on hypophosphite. Additionally, W3110 was unable to grow on hypophosphite pre-incubated in defined yeast medium, suggesting that hypophosphite is not degraded to phosphite by incubation in medium alone. Additional measurements of growth with hypophosphite are shown below in FIG. 16 for strain NS435.

TABLE 3

| Phosphate Source | NS22 | NS435(ptxD) | W3110 |
|---|---|---|---|
| 0 Phosphate | − | − | − |
| 10 mM Phosphate | + | + | + |
| 10 mM Phosphite | − | + | + |
| 10 mM Hypophosphite | − | + | − |

Example 5—Use of Phosphite as Phosphorus Source for ptxD-Expressing *Arxula adeninivorans*

*A. adeninivorans* strain NS252, a wildtype strain, was transformed with plasmid pNC351, containing the ptxD gene under control of the *A. adeninivorans* PGK1 promoter. Transformation was performed with an electrotransformation protocol with selection on defined medium plates with 1 mM potassium phosphite as phosphorus source (see below). Colonies grew on plates spread with cells from the NS252+pNC351 transformation, and 25 of these colonies were patched onto phosphate and phosphite defined media agar plates, and evaluated for the presence of ptxD via colony PCR. 24 of the 25 the putative transformants were positive for ptxD by colony PCR, and 25 of 25 displayed rapid growth on phosphite plates.

*Arxula adeninivorans* transformation protocol

1. Inoculate 5 mL of YPD media in a 14-mL culture tube with *A. adeninivorans* strain NS252 from a YPD plate and put it in the 37° C. drum roller for overnight incubation.
2. Add about 2.5 mL of the overnight liquid culture into a 250-mL flask containing 22.5 mL of fresh YPD and incubate in the 37° C. shaker for 3.5-4 hrs.
3. Centrifuge the culture at 3000 rpm for 3 mins. Discard the supernatant, wash the cells with water followed by centrifugation and discard the supernatant again.
4. To the cell pellet, add 2 mL of 100 mM lithium acetate solution and 40 µL of 2 M dithiothreitol. Transfer into an Eppendorf tube.
5. Tape the tube on the 37° C. wheel and let it incubate for an hour.
6. Centrifuge at 10000 rpm for 10 seconds, discard the supernatant.
7. Wash cells with 1 mL water, and mix by gentle pipetting.
8. Centrifuge, discard supernatant, wash with cold 1 M sorbitol, mix by pipetting, centrifuge, discard supernatant.
9. Add 2 mL of cold 1 M sorbitol to cell pellet, place it on ice.
10. Into the pre-chilled 0.2-cm electroporation cuvettes, add 40 µL of the cells and 5 µL of DNA to be transformed, ideally at >100 µg/mL DNA concentration.
11. Electroporate at 25 µF, 200 ohms, 1.5 kV, ~4.9-5.0 ms time constant.
12. Recover transformed cells using 1 mL YPD at 37° C. overnight.
13. Plate 100 µL-500 µL of the recovered culture onto appropriate selective plates, and incubate at 30° C. or 37° C. until colony formation.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for converting a substrate to a product, the method comprising the step of
   contacting a genetically engineered yeast microorganism with the substrate to produce the product,
   wherein
   the genetically engineered yeast microorganism is a species of the genus *Yarrowia, Saccharomyces* or *Arxula*;
   the genetically engineered yeast microorganism has been transformed by a nucleic acid molecule; the nucleic acid molecule comprises a non-native gene, the non-native gene is not found within a native yeast microorganism of the same species as the genetically engineered yeast microorganism; and the non-native gene encodes for a non-native enzyme comprising NAD: phosphite oxidoreductase (phosphite dehydrogenase); and
   the substrate comprises a phosphorus-containing compound of any one of Formulas I-III; wherein the compound of formula I is

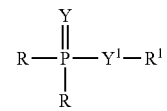

wherein, independently for each occurrence,
$R$ is —H, —OH, alkyl, —OR$^2$, —SH, or —SR$^2$;
$R^1$ is —H, or alkyl;
$Y$ is O or S;
$Y^1$ is O or S; and
$R^2$ is alkyl;

the compound of formula II is $$R^1-Y^1-\underset{Y^1-R^1}{\overset{Y^1-R^1}{P}} \qquad \text{II}$$

wherein, independently for each occurrence,
R¹ is —H, or alkyl; and
Y¹ is O or S; and
the compound of formula III is $$\text{HO}-\underset{\text{HO}}{\overset{O}{P}}-\underset{R^3\ R^3}{C}-\underset{\text{OH}}{\overset{O}{P}}-\text{OH} \qquad \text{III}$$

wherein, independently for each occurrence,
R³ is —H, —OH, —OR⁴, —SH, —SR⁴, halo, alkyl, aryl, heteroaryl, aralkyl, or heteroaralkyl; and
R⁴ is alkyl or aryl.

2. The method of claim 1, wherein the phosphorus-containing compound is selected from the group consisting of:

[structures]

3. The method of claim 1 or 2, wherein the product is ethanol, isopropanol, lactic acid, an isoprenoid, a lipid, butanol, 1,3-propanediol, 1,4-butanediol, succinic acid, an expressed protein product, a polyol, or itaconic acid.

4. The method of claim 1, wherein the non-native gene comprises ptxD.

5. The method of claim 1, wherein the non-native gene comprises *Pseudomonas stutzeri* WM88 ptxD.

6. The method of claim 1, wherein the genetically engineered yeast microorganism is selected from the group consisting of *Yarrowia lipolytica, Saccharomyces cerevisiae*, and *Arxula adeninivorans*.

7. The method of claim 1, wherein the nucleic acid molecule comprises SEQ ID NO:11.

8. The method of claim 1, wherein the NAD:phosphite oxidoreductase comprises SEQ ID NO:10.

9. The method of claim 1, wherein the phosphorus-containing compound is a compound of Formula I.

10. The method of claim 1, wherein the genetically engineered yeast microorganism sequesters the product.

11. The method of claim 1, wherein the substrate does not comprise an antibiotic.

12. The method of claim 1, wherein the substrate further comprises a lignocellulosic material, glucose, xylose, sucrose, acetic acid, formic acid, lactic acid, butyric acid, a free fatty acid, dextrose, glycerol, fructose, lactose, galactose, mannose, rhamnose, or arabinose, or a combination thereof.

13. The method of claim 1, wherein the pH of the substrate is from about 2.5 to about 10.

14. The method of claim 1, wherein the genetically engineered yeast microorganism is contacted with the substrate at a temperature of from about 15° C. to about 80° C.

15. The method of claim 1, wherein the genetically engineered yeast microorganism is contacted with the substrate over a time period of from about 6 hours to about 10 days.

16. The method of claim 1, wherein the genetically engineered yeast microorganism is contacted with the substrate in a fermenter.

17. The method of claim 1, wherein the genetically engineered yeast microorganism is contacted with the substrate in an industrial-size fermenter.

18. The method of claim 1, wherein the substrate comprises the phosphorus-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

19. The method of claim 3, wherein the expressed protein product is an enzyme product.

20. The method of claim 1, wherein the substrate comprises the phosphorus-containing compound in an amount from about 10% by weight to about 100% by weight.

* * * * *

SEQUENCE LISTING

```
<160> NUMBER OF SEQ ID NOS: 14

<210> SEQ ID NO 1
<211> LENGTH: 4127
<212> TYPE: DNA
<213> ORGANISM: Pseudomonas stutzeri

<400> SEQUENCE: 1
atgacgcccc atccgataca ggacgccgtg ctgcgggtcg accggttgag cgtcgtctat     60
ccaggcggcg tgacagccct acgcgatacc tcgattgcat tcggcgtgg tgagttcacc    120 gtgctgcttg gtctctcggg cgcaggcaag tcgaccttgc tccgtagtct caatcgactc    180
gtcacgccca ctggcggcag tgtcaccagc gaactcggtg aactcggcag cggctcggcc    240
ttgcgtcagc atcgtcggcg taccgccatg atctttcagc accaccagct aatcgaacgt    300
caaagcgcac tggctaatgt gctgaccggt cggctggcct tcacaacac gctccgctcg    360 ctgtttcctc tgccgcgtgc cgatcaggag attgcgctca gttgcctcgc tcgggtcggt    420
ctggcagaca aggcgctaag ccgggtggac aaactgtccg gtggccagca gcagcgggta    480
ggcatcgcgc gtgcgctagc gcaacagccg gcgatcattc tggccgatga gccggtagcc    540
agtctcgacc cggccacttc ggtccgtgtt ctcggattgc tgcgcgacat ctgcaaggaa    600
gacggcatca ccgccatcgt ttcgctgcat caactcgaat atgcccgccg cttcgccgat    660
cgcgtcgtcg ggctggccga ttctcagatc gttttcgatg ccgcgccctc ggaactcacc    720
gatgcgcagc ttgagcgcat ctatgcaggc cgctctacga ctcagccagc gaatgctccg    780
gctgaaccac ctgtcatgct cgaaccttca ctggagatgt cccgatgaaa cgcttatccg    840
cgctcttatt gacttgcttg ctgtccgctg tttcaagttt gtccgccccta gcggccgatg    900 ccgatccgga tgtgctaaag gttgccctgc tgccggacga aaacgcctcc gagctgatca    960
agcgtaacca gccgctgaag gattatctgg aagagcatct ggacaagaag gtgcagctga   1020
```

```
tcgtaaccac cgactattcc tcgatgattg aggcgatgcg ctttggccgt atcgacctgg    1080
cgtatttcgg tccgctgtcc tacgtcatgg ccaaaagcaa aagcgacatc gagcccttcg    1140
ctgccatggt catcgacggc aagccgacct atcgctcggt gattatcgcc aatgtggcgt    1200
caggcgtgaa tgagtatgcc gaccttaagg gcaagagaat ggcctatggt gacccgggcat    1260 cgacgtccag ccatttgatt cccaaaaccg tgcttcttga cacggccgat ttgacgggtg    1320
ggcaggacta cgaacaacat tttgtgggca cgcatgacgc cgttgccgtc aacgtggcga    1380
acggcaacgc cgatgcgggt gggctgtcgg aggtaatttt caatcacgca gccgaacgtg    1440
gcctgatcga tccgagcaag gtgaaagtac ttggttacag cggcgaatac ccccagtacc    1500
cctgggcgat gcgctcgaac ctgagccccg agctgaaaac caaggtgcgg gatgtattcg    1560
tcggtatcga cgatcccgaa gtgctgcgca acttcaaggc cgaggccttc gcgccaatca    1620
ccgacgccga ctacgatgtg atccgcaaca tgggatcgct gctcggcctc gacttcgcca    1680
cgatgtgagc accgatatgt cttctcatta cgacgtgcag gcgctgcctg cagagcaacg    1740
cgagcacatc cttcgaggct tcggcctcgg ttggtggcgc cagctggggc aggtggcgat    1800
tgtattcgga gtggtgctgt tggcctgctg gtacgtgggg ctgctcgatg ccaccacgct    1860
gctgaacggg ctgccctcca tcgcgaccct ggcaggcgag gccatgccgc cagacttttc    1920
gggctatcga agctggattc gccccttgat cgacaccttg gcgatgagca tcgccggtac    1980
ggccatcgca gtggtgttct cgctggtggt ggccttcgtt gcagcgcgca atacggcgcc    2040
gcaccccctt gtgttcggtg ttgcccgggt gctgctcaat gccctgcggt cggtgccgga    2100
gctgatcatg ggcatcatct tcgttgcagc cgtagggttc ggcgccttgc cgggcgtgct    2160
tgccctgggt ctgcattcgg tcggcatggt cggcaagttc ttcgccgagg ccatcgagca    2220
cgtcgacgaa cgcgccggtg gaagccgctcg ggcggcgggg gctacgccga tgcaagtgct    2280
gctgcacgcg gttttgccac aggtgacgcc gcagttcgcc gacgtggcga tctaccgctg    2340
ggaatacaac tttcgcgcct ccaccgtgat gggcatggtt ggcgccggcg gtatcggctt    2400
cgaactcatg ggctcgctgc gcatcatgca gtaccaggag gttgcagcaa tcctgctggt    2460
catcctggcc atggtcacgc tagtagacgc cttcagtggc gtgctgcgca aacatttcaa    2520
ataggacaaa ccatgctgcc gaaactcgtt ataactcacc gagtacacga tgagatcctg    2580
caactgctgg cgccacattg cgagctgatg accaaccaga ccgacagcac gctgacgcgc    2640
gaggaaattc tgcgccgctg tcgcgatgct caggcgatga tggcgttcat gcccgatcgg    2700
gtcgatgcag actttcttca agcctgcccc gagctgcgtg tagtcggctg cgcgctcaag    2760
ggcttcgaca atttcgatgt ggacgcctgt actgcccgcg gggtctggct gaccttcgtg    2820
cctgatctgt tgacggtccc gactgccgag ctggcgatcg gactggcggt ggggctgggg    2880
cggcatctgc gggcagcaga tgcgttcgtc cgctctggcg agttcagggg ctggcaacca    2940
cagttctacg gcacggggct ggataacgct acggtcggca tccttggcat gggcgccatc    3000
ggactggcca tggctgatcg cttgcaggga tggggcgcga ccctgcagta ccacgaggcg    3060
aaggctctgg atacacaaac cgagcaacgg ctcggcctgc gccaggtggc gtgcagcgaa    3120
ctcttcgcca gctcggactt catcctgctg gcgcttccct tgaatgccga tacccagcat    3180
ctggtcaacg ccgagctgct tgccctcgta cggccgggcg ctctgcttgt aaacccctgt    3240
cgtggttcgg tagtggatga agccgccgtg ctcgcggcgc ttgagcgagg ccagctcggc    3300
gggtatgcgc cggatgtatt cgaaatggaa gactgggctc gcgcggaccg gccgcggctg    3360
atcgatcctg cgctgctcgc gcatccgaat acgctgttca ctccgcacat agggtcggca    3420
```

-continued

```
gtgcgcgcgg tgcgcctgga gattgaacgt tgtgcagcgc agaacatcat ccaggtattg    3480
gcaggtgcgc gcccaatcaa cgctgcgaac cgtctgccca aggccgagcc tgccgcatgt    3540
tgaatccggt ctggctgaag agcctggtag cgatcgttca acaggcagt tttcagagcg    3600 cggcgagggc gttggggctg gcccagccga cggtgtcgca gcacttgcag aagcttgaag    3660
agcaggtcgg cgtaacgctg gtgcagcgca gtcgtagcgg ctgccagcct accacacggg    3720
cgctggcctt catgccgcat gcgaccgcct tgctcgacat gcacgccggg cgctagaag    3780 ccctgcatgg caatcgtgag cgcgtcgggg ccagctccaa catcggcacc taccttctcc    3840
agccattcgt gcgcaactat ctgacgaccg caaatgagag gggcgaggtg gatctgcgca    3900
tcgccgccaa cccggatgtg gccgaccagc tactggcggg ccagctcgac gccgcgatca    3960
tggaatggtg gctacctcac cccgacttcg aataccgcct ctggcgggtc gagccgctgg    4020
tgcttatcgt cagccccgac catgcgctgg ctgaagcagg gtgcatagaa cgtgatcgtc    4080
tggtggacct gccgatgctg ggaggtgaac cgggtagcgg tacctag                  4127
```

<210> SEQ ID NO 2
<211> LENGTH: 13771
<212> TYPE: DNA
<213> ORGANISM: Pseudomonas stutzeri

<400> SEQUENCE: 2

```
atgtttgcag agcagcaacg cgaatatctc gacaagggat atacgaagat tgaaagcttt      60
ttctccgcgg aggaagtagc gaagattctt gaagacgtca agcaaattga attgggagct     120
attggcgtag cttcggacaa tgagacttac cagttcgaaa agaagaatgg cgagacgacg     180
aagctactgc gtcgcgtcga gaatcctcac ctttatttcg atgcaataga ttctttggtc     240
aggtcggaaa aaatcgtcga tttgcttcgg catttcctgg gcgaaaacat ccgtttgcac     300
aatagcaaaa tcaacttcaa gccgccatca ggcgcgccag tccagtggca tcaggactgg     360
gcattctatc cccacacaaa cgatgatttt cttactctcg gaattttcct cgacgagaca     420
agtgagaaaa atggcgcgat ggcatgcttg ccaggctccc acaaaggaaa agtgtacgac     480
caccggaacg tcgagacggg cgagttttgc acgcgatct ctcgctccaa ctgggacgaa     540
gcgctcgacc cgacagaagg ggagttactg acgggacccg taggaactgt cacgttgcat     600
cacgtccgga cccttcatgg ttcaggccca aaccactcaa cgatcaggcg cgttttctg      660 ctcatcggct atgccgcggc tgatgcctgg ccacttctgg gctgtggcaa ctatggggat     720
tatgaaagcc tcatggtctc tggccgatcc accgtattcc cgcgcatggt ggaactccct     780
ttgactgtcc cgtatccgtt gtcgatgtac ggtgatcgca tctttgaaag tcaacgagct     840
ttgactcaaa agtactactg aagtctttaa ctcactgagg tcataatgca agttttact     900 ctgttttcga aattcaagaa ggcgttaacg cgcgccattc ttgcctttat cgccacaatc     960
atagtgtgca cacccgcgca ggcagctgag ttgtcaatg gtaaacttca cctgcgtttt    1020
gcaattgcgc cgatgcgtcc aacgcctagc cagaccatca aagagtttga ccgatattc    1080 aagtatctcg ccgaccagct cggcgcgacc tatgaaatcg tctccccgga aagctgggcg    1140
gcaatatctg tggcaatgac aaatggccat gtcgatgtgg ctggctcgg accctggggc    1200 tatgtcttgt cgaataaaaa ggccggcacc gaagtgcttg caacggtcaa gtaccgcggg    1260
gagccgttct acaaagccct cattgtcggt cgcgccgatc tgccgatcaa aaatggcccc    1320
gaggacgcga agggtttgaa gctgtcactc agtgatcagg gcaacacttc tggctggctc    1380
```

-continued

```
atcccgatgg cgtacttcaa gagcatcggc atcgaccctg cgagctattt tgaatatcgt    1440
gaaggtgcca cgtttggcca gaacgaatca cagattcagc acggactgat cgacctcgga    1500
tccgatatgg atcggggccg gaacgggatg atcgaagcgg gtcaaatcga tccttcgaag    1560
tccaagatcg tgtgggaatc cagcaagctg ccgaacgacg cgatatccgt gccgaaggat    1620
tttgatcctg ctctgaaagc gcgcatcacg gaaatactga cgtccttgtc cgaagagaaa    1680
gcacagtcgc tgatgggctc gggctataac ggcttcgtga aggcaaagca cagcgattac    1740
aaggtaatcg aagacgccgg ccgcatcctg ggaaaactgt aaagcacgag gggtccgttc    1800
ttggatgagg gcagcggacg acaaggtgga ctgacgcacg ccagctcctt gtctccgctg    1860
cacgaacata cgggcgcgca tcgcaatacc acagaggatg aaccaatgaa tcagcgaatc    1920
gaagaagtca tgctggctaa tgtcaagagg gacgtagcca ggagaaagcg gcattttgca    1980
acgtcggtcg tagtactcag tttgctggca gtggcctggt acgtgtgtca gatagaattc    2040
cagaagctag gcgccggttt accgagacta tggtcattcg tcgtgcagat gtttccaccc    2100
gacctgagcg acctggacgt cattctaaaa ggggctggcg agacgctcgc catggcgacg    2160
attggcacga tattcgccac aatcattgca tttccgctgg cactcatggc tgcgcgtaat    2220
acctgtccga acaagtggac ctatcgggta tcccgcgcca cctgaacgc cagccgcggc    2280
acggagacat tgtctatgc acttgtattt gtagcagcag tgggcttcgg tccgttctcc    2340
ggcgtactgg ccattacttt ccacatggta ggggcaatcg gcaaaatgtt tgctgaagcc    2400
atcgagcccg ttgaccaagg gccgttggat gcgctcgcct tgaccggtgc cagcagggca    2460
aagattatcc gctacggtct gatcccggat gttatgccgc acctgatcgc gagcgttcta    2520
tacatttggg aattcagtgt cagaacgtcc acagtactgg gcatcgtagg cgcaggtgga    2580
attgggcaga ccctgaaaga tactgtgac ttgttggaat tcaacaagat gattacggta    2640
ctggcggttg tattgctgat ggtgtcggca atcgatttca tcagtgaccg gctcaggtac    2700
ttgatattgg acacaaaacg cgagggattc gaaactctcc ctgcgaataa ctgattgctt    2760
cacgtattac tggaagggag gttcgcaatg aaagatgtag cgttgcagtt aaagaatgtc    2820
ggtaagtcat acggcaataa agttgtcctg gaatcgattg acttcgaagt acgtcacggc    2880
tcaatggttg ccttgctcgg cacaagcggg gcagggaagt cgacgctttt ccgatgtctc    2940
actggccttg agccgattga ctccggttct atcgtggcgc tcggagaatc catacatgaa    3000
ctgtctccgg cgcgtctgcg ggcagtacgt ggccagatcg ggttcgtgtt ccaacaactg    3060
cacctggtga aaaggttctc agcactcgag aatgtattgg gtgcgcgtct ggcagagatg    3120
cccatttggc gcgtcacatt gaaaagcttc agccgggctg acaaagtgct cgcgttcgaa    3180
tgtctggacc gggtcggcat gctcgattat gcaaacacgc ctacgcaact gctgtcaggc    3240
ggtcagcaac agcgtattgc gatagcgcga gccttggcgc agaagcccaa gattattatt    3300
gcggacgaac ccgtctccag cctcgatccg ctgacggcgc gctcggttct gcaaacgctg    3360
aaagccgcgg ctacagatct taatgtcgcg gtcctgtgca gcctgcacca ggtagacctg    3420
gcccgtgagt ttggcgaccg catcgtgggc atgcgcgacg gacgtgtcgt tttcgacggc    3480
acgccagcgc aattcaccga cgagcgcgtg catgcgcttt accaggtgcc cgctgggaag    3540
atgcaccagc ggccgagagc gacgcgcagc actcggtggc cggtctggct gtggcatgag    3600
gggcgaagcg atgaccacat ccacacgccc catacccgtg ccgccccagg caccgcact    3660
gcactggcac ctgagcgcgc cctacaacgc caaacatctg ctggtgctga tcgccgtcat    3720
ggtgctgttg ttcgtgaccg gacaacgcac cgaaatggac cgcatggtgg ccatgacggc    3780
```

```
acaggccgtg gccaagaccg tgggcctggc tgacgattca caagtcgcgc gcggcttgtc    3840
gcgcgtcggt caagccatgt ggccacccgc catcgcagaa accgaagagg tgggccggat    3900
tcaggacctg gatcgccaga agctgcccct gttctcgcac atcgagaccc aggagcgcgt    3960
cgagcagaag atgaatctgg acacgctgaa gatggaagcc acgacggaaa ccgtcgaagt    4020
gctggtcaag ccggtcggct atgtctggac ggttttcatc aagatgatcg agacctggag    4080
attgcgctgt ggggcacgat cctgtcggtg ctggtgtcga ttcccctggc gtatttcgcg    4140
gcccgcaact actagcccca accgttttac ctacaccgct gcccgcggca ccatcagtct    4200
gctgcgttca gcgccggaac tcatcgtcgc tttgttcctg gtgctggcct acggctttgg    4260
ccccatcgct ggcgtgctgg cgctgggcct gcatgcggcc ggcttcctgg caagttcta    4320 cgccgaggac atcgagaacg ccgacaagaa gccgcaagag gcgctggagg ccatcggcgc    4380
gggcaagctc aagacgctgt ggtacggcgt catcccccag gtcttgccgc aatacatcgc    4440
ctacaccgcc tacatcctgg accgcaacct gcgcatggcc accgtcatcg gtctggtggg    4500
cgcgggcggc atcggccagg aactcaaggg ccgttttgac atgttccagt acggccatgt    4560
catgaccatc ctgatcgcga tcttcgtctt tgtgttcgtg ctggaccagt tgcaggcgcg    4620
catccgcgcc aagctgatct gaggcgaccg ctgacaacaa ggaacaacat gacaaacact    4680
tctgaagcac cggatcgtgc gcagtggctg cggctgtggt cggccttgcc ggccgcagcg    4740
gtcaaggccc tggcggccga tctggcgggc cagcaccggg tcgaagacct ggcgttgccg    4800
caatccggtc tgggcctgct gccgctgacc gacagcgccc tgggcgatac ctatttcatc    4860
ggtgagattc ccttggcaca agcgcatgtg cgggtcacga ccacccaagg gcagtcgatc    4920
gaaggcgcgg ccattctggt ggacgaccgt gccggtgtgg cccgttccat ggccatcctg    4980
gacgcggtgc tggcggcccg catgccaggt tgtgaagcgg ccctgcggtt gctcacccag    5040
ggtgcgaccg ccgtggcgga acaaggccgc cagcgccgcg ccttactcgc ggccacgcgg    5100
gtggactttg ccctgctggg aacgaacgag gaggacgatg atgaatgaga ctgggatggc    5160
ggcggcaccg gcagaagccg cgtggcgcat ctggcaagcg ccgcgccagc aaacggcgtt    5220
tcgccagttg atgaccgcgt tttcctatcc gggccgcgtg gtgccactgg ccgatggcgc    5280
tgaatcggcg ctcctgctgg tgttgaccac cctggtggac agcgcctgtg cgctggccga    5340
tccgctgcac gcgctatcaa gcgacgatct gcgccgactg ggcgtgcgct cggccagtgt    5400
ggaggcggcc gagttcgtgc tggccgatgg caaccgtttg ctggaggcca cgccgcgcct    5460
gggatcgctg gaaaaccccg aacaaggcgc gaccgtggtg atgcgcgtct cccgtttcgg    5520
tgagggtccc catctgcggc tcaccgggcc gggtattcaa cacgagcagg tgctgcaggt    5580
cagcggcatc gatccgggct ggtggaagca acggtccgaa tggaatgccc acttcccgct    5640
gggcgtggac ctgattctgg tgagcgggca cgaggtcgcg gtattgcccc gaaccaccca    5700
catcaacctc aaaggagccc actgatggga tacgttgcca tcaagggcgg tggccgggcc    5760
atcgccggtg ccgaagccgc cgtcgaagcc ctgcgctgcg ccgaagggcc agcgggtacg    5820
ccgctcacgc tgtcggccat cgaacagcag ttgcggttgc tgacatcgcg cgtcgtgtcg    5880 gaaggggggcc tctaccaccc acgcctggcc gctctgccca tcaaacagat gcagggcgac    5940
acactggaag cggcgttcgc tctgcgcgcc taccgctcca ccaagccacg cctgatggat    6000
gtgccggtgc aggacacgag ccgcatgcgc ctaatccgcc ggatttcgag cgcttttcaag    6060 gacatccccg gcggacagat gctgggcccg accaccgact acgcgctgcg cctgatgcgt    6120
```

```
ctggatttgg ccaacgagtc gcccgaggac tttcgcgcgg tctcgcggcg gtttctggac    6180
agcgtggccg acaccgacct gcccgacagc ttccccaagg tggtcgatgc cttgcgtgac    6240
gaaggcttgc tgccgccgct gacccggcgc gcccatgcgg cgttcgacat cacccgcgac    6300
ccgctggttt tcccagtgcc gcgttcggcg gccctggcca ccatggcacg cgccgaaacc    6360
ggctcgctct tggcgattgc gtattccaac atgcgtggct atggcgacgt gcaccccacc    6420
atcgccgagc tgcgcgtggg ctatgtgccg gtgatgctgc cgcacccggt gacaggcgag    6480
cccatcgaag ccggtgaggt actgatgacc gaatgcgaag tggtggccat gtttgagggt    6540
gatgctaccg acggcccacc cactttcacc ctaggctatg cgcctgtttt cggtcacaac    6600
gaagtcaagg ccatcgccat ggccatcctc gaccgcgccc tgcaaaaggg tatgcgcgac    6660
ggtcccagca cccgtcggaa agacccggaa ttcgtgctgc tgcacgtcga tggcgtggat    6720
tcgatgggct ttgccagtca ctacaagatg ccgcactacg tgaccttcca gtccgacatg    6780
gaccggctgc gcaccacgca ggacaaggca accgcacaac cgacccaaga aggagcgcca    6840
tcatgaaccc gggctacgaa ctgccctgg acgaggcggg ctacagcttc ggcttcctgg    6900
acgaatacgc caagcgcgag gtgcgccgca ccatcctcaa ggcgatcagc atccccggtt    6960
accagacgcc ctatgcctca cgcgaaatgc ctatggggcg cggcttggc accggcggtc    7020 tgcaggttac gctgtcgctg attggcgagg gcgacaccct gaaggtgatc gaccagggcg    7080
cggacgactc cgtcaacgcg gtgaacctgc gtcactttgt ggaactgacc tgcccggggcg    7140 tggacaccac agaacacacg cttgatgcca ctctgatcca gtcgcgccac cgcattccgg    7200
aaacgccgct gaccgaagcg caggtgttga tcctgcaagt gccgtatccg acccactgg    7260 tggtggtgga accctccgag gctcgacgca aggtcatgca cggcgaaggc gactattcgc    7320
ggctgctgac caagctgtac gaggacatcg tgcagtttga cgagatcacc atctcgcacc    7380
gctaccccac gcgcatcaac ggccactatg tgatcgaccc cagcccgatc ccgcgctacg    7440
acgtgccgca gttgcaccag agcccggcgc tgatcctgct gggtgcgggg cgcgagaaaa    7500
aaatctatgc ggtgccgccg tacacccgcg ccgacccgct ggcgttcgac gacgtgccat    7560
tccgcaccga agacttcacc aacgaacacg gccagcgccg cgcctgcgaa cggtgcggcg    7620
ccaccgacag cttcctcgac gagctcattg ccgacgatgg cggcaagcac tggcattgct    7680
cggactcgga ttttttgcaat agccgtatgg cccgccaggc tgaacaagct caggagacca    7740
cggtatgaaa aaaattctgg aagtacgcgg actgaccaag atccacggcc ggggttgcga    7800
actctgcctg gagagcactg gccccgacat ggacaccaac atctgcccac actgtggctc    7860
ggtggtggcc tgccacaaca tcagcctgga cctgcacgag ggcgagatcc tcggcatcat    7920
gggcgagtcc ggcagcggca agtccaccgt ggtcaagacg ctgttcttcg acgatgagcc    7980
caccgctggt gaagccctgt tttttgacgg cgagcgccag tgggacatgt tcgcgctcaa    8040
cgccgcgcag cagcgctggc ttgcgcaacc accgctttgg catggtgtac cagaacccgc    8100
atctgggact caatttcaac gtctcggccg gcggaaacat ttgccgagcg ccttgctgat    8160
gagcgacctg gcccactacg gcgaaatccg cgaacgggcg cgcagcttgt tggcgcgcac    8220
tgaggtgttg gcagaacgca tggacagagtc gcccaagaag ttctcgggcg gcatgcagca    8280
gcgcgtgcag atcgccaagg cactggccac ccagccgccg ctgctctacc tcgacgaggt    8340
caccaccggc ctggaccttt cggtgcaggc gcgcatcctg gacctgattc tggaaatcca    8400
gcaggagctg ggcaccgcca tgatcgtggt cacccacgat ctgggtgtca tccgcctgct    8460
gaccggacgc acgatcgtca tgaaatacgg ccgcggtcat cgaagtccgg gctgaccgac    8520
```

```
cagatcctcg aagaccccca gcacgcctac acccagcgcc tggtcgcgtc ggcttctctg   8580
aggaaacctg aatcatgcaa gaagccatcc tcaaaatcga aggtctctcc aaacagttcc   8640
agctgcacga ccagaacaaa ctgatcccgt cgtgtgcaca ggttcaactg gaggtgtttg   8700
ccggcgagct gaccgcgctg atcggcccga ccggcgccgg caaatcgtcg gtgctcaagg   8760
ccatttaccg cacctacctg cccagcagtg ggcgcatcct ttaccgggac gccaacggtg   8820
ccatcaccga tctggcccag gccagcgaac accgcatgct ggagctgcgc aagcaggacc   8880
tgggtttcgt cacccaattt ctgcactgtc taccgcgcaa gtcggcggtc gaggtagtgg   8940
ccgagccgct ggtgcagcgg ggcagcccgc gcgaagctgc tgccgagcgc gcgcgcgaac   9000
tgctggccct gctcaacgtg ccggaacgct tgtgggcggt accacccgcc accttctcgg   9060
gcggcgagaa acagcgcgtc aacctggcac gcgggctgat cgcccggcct cggctgctgt   9120
tgcttgacga acccacggcc agcctagacc cgtccaccac cgaccgcgtg gtggagctgt   9180
tgaagtccat caaggccgaa ggcgtggcca tgctggccat cttccacgac cccgaacttg   9240
tccgacgcct ggccgatcgc gtcgtaaccc tcacgccccc ggtgtctgcg gcggcattgc   9300
tggagacctg tgcctcatga atcccatttt gctgacccat gcccgcgtgg tgttccccac   9360
cgaagtccgt gacaacgtgg ccatcctgat cgaaggcgac accatcacag catcgacccg   9420
gccagcagcg caggtgccac cgagatcgac ctgcgcggct cgcaccctga tgccaggtct   9480
gatcgacctg cactgcgacg caatggagaa agaggtggag ccgcggcccg cgtgcactt    9540 cccgctggag ttcgcctgtg cccaggccga caagcgcaat gcggcggccg gcatcacgac   9600
ggtgtttcat gccctgtcct tgccaaacca cgagctgggc gtgcgcaaca acgccttcgc   9660
cgccgagatc gcccgttcga ttggcgactg gcaggcccat gccctgatcg acaaccgggt   9720
gcatgtgcgt tacgaggtga cggacgaaac ggcgccgccg gtgctgtcgg cgctgctgca   9780
ggacggtcat gcgcacctca tgtctttcat ggatcacagc cccggtcagg gtcagttccg   9840
cgatgtcgag gcgtaccgcg cctacctggc caagacctac aagaccgatg aggcgcagat   9900
cgacgacatc ctggcgcgca aagcgggggc cgcacagggc gccatgcggc gcatggagca   9960
gcttgcggaa ctggcccgtg cgtgcggcgt gtccattgcc agccacgacg acgacagccc  10020
gcagaaagtg gcgaccgtca aggccctggg cgctgtggtg tcggagtttc cggtgaacct  10080
ggagacggca caggccgccc gtgcacaagg cctggccacc ttgtttggcg ctcccaacat  10140
cctgcgcggc aagtcccagt cgggcaacat gcgtgccctc gatgccgtgc tggccggtgt  10200
cgccgactgc ctgtgcggtg actactcgcc agcggcgctg ttgccgtcgg tcatgcgctt  10260
gcccgatctg gccggcatcc ccctggccga ggctgtggcc ctcgtcacgt gcaacccagc  10320
tcgtgctgca ggtttgcacg accggggcga gatcgccgtg ggcaagcgcg cagacctgat  10380
tgcggtcaaa accatgggcg gactgccaca ggccgagcgg gtctggtcgg gcggtaaagc  10440
ttcgctggtc gcgcattttg accacgcctg agagggactg gcacatgcga actcgcctca  10500
tctacgtggt cggcgcctcg gcagcggca aggacacgct catgggccat gcccgccaga  10560
agctggcggg tgatcccagg gtgtgttttg cccatcgcta catcacccga cccgcaacgg  10620
caggcggcga aaaccatgtg gccttgacca cggaggaatt caccgctcgc cagaacggca  10680
agctctttgc catgcactgg tccagccacg gcctgcatta cggaatcggc atcgagatca  10740
accagtggct gggcaaaggc atcacggtgg tgatcaacgg ctcgcgggaa tacctggacg  10800
aggcccgcca acgttacccg gagctgctgc cggtgacgat tgacgtggcc accaccgtgc  10860
```

```
tgcgtgatcg gctgctggcc cgtggccgcg aggatgccga atccattgag cagcgcctgc    10920
accgccatga aacgttgcgc ctgcagcccg tgcccggtgt gctcatccag aacaacggac    10980
ccgtcgaggt ggccggcgaa gcgctgatcc ggttgatcgc agaacacacc caaggagcgc    11040
cagtatgcgt gtgagttttc tgggcacggg cgctgcgggc ggggttccgc tctacggttg    11100
cacctgccgg gcctgtgaac gcgcaaggac cgagccacac ttcgtccgcc gcccttgcag    11160
cgccctgatt gaatccggag gtacccgggt gctactggat gccgggctga tggaccttca    11220
cgaacggttt gcgccgggta gcctggacgc gattgttctc acgcactacc accccgacca    11280
cgtgcaggga ctctttcatc tgcgctgggg taaggggacg cccatcacag tctatggccc    11340
accagacagc gaaggctgcg ccgatttgtt caagcaccct ggtgtactgg ccttcgagac    11400
ggtgcacaag ttcgaggcct tcaccgtcgg ggcgctgcgc ctgacgcccc tgccgctgct    11460
tcactccaaa cccacgctgg gctatgccat cgagggcacc cagggccaac gcttcgccta    11520
cctcacagac accctgggtt tgccgccgaa gtcggccaag ttcctgcgcg cctggggcga    11580
ctttgacatg gccatcgact gttcctatcc gccgcacccg accccgaaaa accacaacga    11640
ttgggacgaa gcacatcggt gtgccatcga atctggtgcc cgcatcacct ggctcaccca    11700
tgccggtcat gcgctggacg actggatgat ggaagagacg ccgagcgtcg caagtcatat    11760
ccggctggcc cgggacggca gcacggccga cataccgtcc caaacgcaat gaacgcgccg    11820
ctggcactgg ccctgtcggt ggccatgcac gtcacctgga acctgatggc acggcatttg    11880
cccagggaat cgaacccgct gtggtgggtg ttgctcgccc atctggtgct gtttgcgccc    11940
tgggggttct gggagctggc gacaaccgtc gtttggtcac tggagatgac gctgctactg    12000
atcgtatcgg ccactgcgaa tgtggtttat ttctccggtc tggccagggc ctacgagcac    12060
gcaccggtcg cactggtcta tcctctggtg cgcagttcac ctcttttcat tgcgatctgg    12120
ggcacgctgt tcttcggtca aaatctcccg cccattgcct ggctgggcat tggcatcagc    12180
gtgctgggct tgctcgtcat ggcatcgagt gctcaacagg ggtcggatcg acgagcattc    12240
cgatgggcca tgctggccat gttggcgaca agcgtttatt ccctgagtga caaggcggcc    12300
accgaacaca tcccaagctt catggggctc gtgggttttc tgtccgtcgg ctacctggca    12360
tcctggatca gcatgacctt gcgcatgcat cggcacaccc gcagttgggt gccggcacag    12420
cgcattgatc tcgcgtcgct ggctcttggc ggaacctgta tcggtctcgc ctacgccttg    12480
gttatccacg ccatgcgcca gttgcctgcg gcggaggtcg tgtcgtacac caacgccggt    12540
atcgtgctcg ctgcagttct ctccattttt ttgttcaatg acaaagtcgg atggcaaaag    12600
agaatcatgg gggtcgtgat catcacgagt ggtttggggg tgcttgccat gaggtgagcg    12660
acacaatacc aaccatcgca caccagcatt ccaacccggc tcgcgacctg ccggtgaagt    12720
aaaagcgact tccgatatgt cccaaatttc ccgatacgtc gaggccgccg agcgtgacaa    12780
cacgcgtcga agctatgccg cagccattcg ccatttcgag gtggagtgga aaggcttgct    12840
gccaacgacc gctgatgcaa cctcccgtta cctggctgac cacgcggcca cgctggcgat    12900
cagcaccctc cgtcagcggc tcgccgcgct ctcgcgctgg cacatcgacc atggttttgc    12960
agacccgacc aaggcaccct tggtgcgcca ggttctcaaa ggcattcgct ccattcactc    13020
ggttgcagaa aagcgggcac gccccttga aatcgatgtc gtccagcaga tcgatcaatg    13080
gctgggggtg gccatcggca acgcagaacg cagcgatgac cgattggcgc tgcttcgcca    13140
cacccgcaac cgcagtttgc tgctgctggg ttttctggcg ggatttcgat cggacgagtt    13200
ggtcaacctg cgggtggaga acgtggaagt ctcgcctggc gaagggctgt cgtgctacct    13260
```

```
gagccgcagc aagggcgatc ggcagatgct gggccgcgta tacaaatgtc cggcgctgtc    13320
ccgcctgtgt cctgtgacgg cttttcacggc atgggtcagt ctggtcggcc tgacccaagg    13380
cccggtgttt cgcaagatcg accgctgggg gcgaatcggt caagaagggc tgcatgccaa    13440
cagcctgatc ccattgttgc gcagccttt ggctgaggcc ggggtccccg cttccgaggc    13500
atacagcagc cactccctgc gtcgcggatt tgccggttgg gctcgcgcca gcggttggga    13560
catcaaggaa ctcatggagt acgtgggctg aaggatgtc aaatcggcca tgcgttatct    13620
ggatgcctcc ggcagcgcac ttcaggcccg gtttgaggcg gtctcgcaa cactggcccc    13680 agcagatcga gcggatcggt caccaccgcc ttcgatgcac gcgccggccg agcaaaccaa    13740
gggaacaggc ccagaggccc cgtctgcctg a                                    13771

<210> SEQ ID NO 3
<211> LENGTH: 792
<212> TYPE: DNA
<213> ORGANISM: Delftia acidoorans

<400> SEQUENCE: 3
atgcacaagt tcatccacat cacggacatt catcttgtcg agcagggtcg cgccctctac      60
ggccatgacc ccggcaaacg gttcgagcgc tgcatcgaca gcgtgatcgc cgagcacgcg     120
gacgcagcgt cttgcgtgat cacgggcgac ctcgcacatg tcgggcaccc ggacgcctac     180
cgccagctgt cggagcaatg cgcgcggttg ccaatgccgg ttcatctgat tctcggcaac     240
cacgacagcc ggaccaactt ccgcgagcgc ttcccacagg tgccggtgga cagcaatggg     300
ttcgtccagt acgagcaggc catcggggagg ttcaggggtc tgtttctgga taccaacgaa     360
ccgggaacgc attgcggcgt cttctgcgag caacgggcaa actggctttc ccagcgcttg     420
gcggaggatg attcaccggt gctcctgttc atgcatcatc cggcattcca ccttggcatc     480 ccgtcatgg atcgaatcgg attggtcgac aacgaatggt tgctgacggc gttgaagggc     540
cacgagcacc gcgtcaagca cttgttcttc ggccacattc atcgcccat ctcgggcagc     600 tggcgcggca tcccgttctc gacattgcgc ggaaccaacc accaggtggc gctgcacctt     660
cgggaatcgg aagacatccc gggaagcttc gagccaccac agtacgccgt cgtcctgctc     720
gacgacgatt cggtgatcgt gcacctgcat gactttctcg atcgcagcga gagattctgg     780
ctaggcgcgt ag                                                         792

<210> SEQ ID NO 4
<211> LENGTH: 4967
<212> TYPE: DNA
<213> ORGANISM: Enterobacter aerogenes

<400> SEQUENCE: 4
atgaataagc gctggctccc ctggctgata ctgtcgcctt ccctgttgtt tttactgctg      60
tttacctggt ttccgcttgg ccgttcggtc tatgacagcc tgtttgatac ccgcatggcc    120
agcgacggcg cacagtacgt cgggctggat aacttcgccc gctgtttgc cgacggcgtt    180 ttctggcaat cgctggtcaa taatctgctc tatatcctgc tgacggtggt gcccggcgtg    240
acgctcgctc tgctgctggc ggtggcgctg agcgagaatc accgcgtcaa ccgctggctg    300
cgcaccgcct ttttcttccc gatgattatc ccgatggtta gccgccgcgc gctgtggctg    360
tttattttta tgcccggcct cggcctgctc gatcactatc tggcgaagct atttggcctt    420
cagaacaaca actggctggg gcgcagcaac agcgcgctgc tggcgctggc gctgattggc    480
```

```
gtgtggaaat cgctggcta ctacatgctg tttttcctcg ccgggctgca gagcattccg    540
gcctcaacgc gggaagcggc gctgatggaa ggggccagcc gcacccaggt gttttttaag    600
gtcacgctgc cgctgctgcg cccgacgctg agctttgtta tcaccaccgc gctgatttac    660
tccattaccc agattgatca cgtcgcggtg atgacgcgcg gcgggccgga taacgccacg    720
accgtgctgc tctattacat ccagaatctc gcctgggata cccacgacct cggcaaagcc    780
tccgccgcca ccttcctgac gctggccggg ctgtttgcct tctcgctgat taacctgaaa    840
ttgctggaaa aaggagccca ctatgagcgc tgaaatctcg ccgctgatgg tccgctcgcc    900
cgccgctgcg cgtccgctgt ggttgcgcct cgtcgctca cagcccttta ccctgacggt      960
aatcatgtgc tgcctggcgc tgctatgggt gagcccgttt atctggatgc tggcgaccct   1020
gttcagcgcc accaccttcg gcgaagatat ggcctcattg ctgccgcgcc tgccgctgac   1080
cctcgataac ttccgcgacg cctgggacag cgccgactgg ctgagcctgt acgccaacac   1140
ccttatcttt accttcggca ctttcttcgt gcagctactc accatcacca ccgccggcta   1200
cgtcttcgcc tgccacgaat tcgcggcaa gaaaatgcta tttctgctgt ttctcgtcca   1260
gctgatgatc atgccggtgg tgatgatggt gccgaacatg ctgaccctga aaaccttcgg   1320
cctgctcaac actctgaccg gcgtgatgat gccttacttt acctcggcgt cggcgtgtt    1380
tctgatgcgc caggcgttcc tcgccatccc gaaagagctg aagaggcgg cgctgatgga     1440
gggatgccgc tggtggcagg tgctattccg cgtactgctg ccgatgtcct ggccgtcggt   1500
gctggccttc gccaccgtca gcattaccta ccactggaac gagtacctgt ggccgctgat   1560
gatgctcaac gatcccgata agcaggtgct gacggtcggg ctggtctctt cgccatggg   1620
cgctgaatcc ggcggccagt ggggcaccat cggcgccggg acgctgatgg tctgcctgcc   1680
gctgatgctg gcgttcatcc ttttccagaa acagttcctg cgaagcttcg gcttctccgg   1740
gatcaaataa ggagttattc atgctgttag cgcacatttc cgatacccat ttccgcagcc   1800
gcggcgagaa gctgtacggc tttatcgacg tcaacgccgc caatgctgat gtggtttctc   1860
aacttaacgc gctgcgcgaa cgcccggatg cggtggtggt gagcggcgat atcgtcaact   1920
gcggccgtcc ggaggagtat caggtcgccc gccagatcct cggcagcctg aactatccgc   1980
tgtatctcat ccccggcaac cacgatgata aagcgctgtt tctggagtac ctgcagccgc   2040
tgtgtccaca gctcggtagc gatgccaata atatgcgctg tgcggttgac gacttcgcta   2100
cccgcctgct gtttatcgac tccagccgcg ccggcacttc aaaaggctgg ctgaccgacg   2160
agaccattag ctggctggaa gcgcagctgt tcgagggcgg cgacaaaccg gcaacgatct   2220
ttatgcacca cccgccgctg ccgctgggca atgcgcagat ggacccgatt gcctgcgaaa   2280
acggccaccg tctgctggcg ttggtagagc gtttcccgtc gctgacgcgc atcttttgcg   2340
gtcataacca tagcctgacc atgacccagt atcgccaggc gctgatctcc accctccccg   2400
gcaccgtcca tcaggtgcct tactgccacg aagacactcg cccgtattac gatctctcgc   2460
cggcttcgtg cctgatgcac cgccaggtcg gcgagcaatg ggtgagctac cagcactcgc   2520
tggcccacta cgccgggccg tggctgtacg acgaaaacat cagttgtcca acggaagagc   2580
gctaaccgcc atgctcagtc tgcaaaacat cagtaaacat ttcgacggta accggcgct    2640
cagcgcgctg tcgcttgata tccacgaagg tgaatttgtg gtgctggtcg gcccgtcggg   2700
ctgcggtaaa agcaccctac tgcgcctgct tgccggggttg gatcaggtca gcgaaggcga   2760
aatctggctg catgatgaga acatcaccga caccacgccg cgcgaacgca attttgcgat   2820
gatcttccag aactatgcgc tgtttccaca tctctctgtg cgcgacaaca tcaccttcgg   2880
```

| | |
|---|---|
| catgaaggta cgcaaggaag agaaaagcgg ctggcagccg cgggtagata aagtggcgca | 2940 |
| gatgctgcag ctggaggcgc tgctcgatcg caaaccggcg aagctctccg gcggccaacg | 3000 |
| gcagcgggta gcgatggcgc gggcgatcgt gcgtaatccg cggctgttct taatggatga | 3060 |
| accgctgtcc aacctcgacg ctcgtctgcg cagcgaagtc cgcgacagca ttatggacct | 3120 |
| ccaccagcag ttaaaaacca gtaccgtcta cgtcacccac gatcaaaccg aagccatgtc | 3180 |
| gatgccgac cgcatcgtgg tgatgaacgg cggccacgtg cagcaagtgg ggcggccaga | 3240 |
| gtatctgtat gccaacccgg ccaatctgtt cgtggccaga tttatcggtt caccggcaat | 3300 |
| gaatctgcta tcgctcccct gcgttgacgg caacgttcag cttggcgaac aacgccatcc | 3360 |
| gctaccgccg cgccatcgca gccagacccg tgtctggctg ggcattcgcc cggaacatat | 3420 |
| taccgaccgc gtggagcacg gccatctgcg cctgccgggc accgtcctgc aacgagaact | 3480 |
| gatgggagcc gattatctgc tccacgtcag caccccgatc ggcaccctgc gctttagccg | 3540 |
| ccgccaccgt ggcacggtgc cggaaaaagg cgaatcgctg atcctcggct tctcgcctgc | 3600 |
| cgatgtgcat cttttcatg ctgagaccca gcataattta ctgatggagt gtaatcatgt | 3660 |
| ttaacccct caccgccctg acggttgggc tcagcctcgc cctgagcggc acggcgctgg | 3720 |
| cgaaagagaa aatagacttc atgttcccgg ccccggtaga cggcaagctg acgatggaga | 3780 |
| tgacacgcgt cattaaagcc tttaacgagt cgcagcagga tgtcgaagtg cgcggcatct | 3840 |
| tcaccggcaa ctatgacacc accaagatca agccgaatc cgcgcagaag gccgggcaac | 3900 |
| ccccggcgct ggtgatcatg tccgccaact tcaccaccga tctggcgctg aaggatgaga | 3960 |
| tcctgccgat ggatgagctg tttaaatatg gcgatcaaaa ggccggcgat tttctgcaaa | 4020 |
| aggaattctg gcccgcgatg cataagaacg cccaggtgat gggcaccacc tatgcgatcc | 4080 |
| cgttccataa ctcgacaccg atcctctact acaacaagac gctgttagat cgagctggga | 4140 |
| tcgcgcaacc accgcagacc tgggccgagc tgctggccga tgccaaaaag ctgaccgacg | 4200 |
| agagcaaagg ccagtggggg atcatgctgc cgtcgaccaa cgacgactac ggcggctgga | 4260 |
| tcttctcggc gctggtgcgc gccaacggcg gtaaatattt caatgaagac tatccgggtg | 4320 |
| aggtttatta caactcgccg accgctatcg gcgctctgcg cttctggcag gatctgatct | 4380 |
| acaaagacaa agtgatgcct tccggggtac tgaattcgaa gcagatcagc gcttcattct | 4440 |
| tctccggcaa acttggcatg gcgatgctca gcaccggcgc actgggcttt atgcgcgaga | 4500 |
| acagtaaaga ttttgaactc ggtgtcgcca tgctaccagc caaagagcag cgcgcggtgc | 4560 |
| caattggcgg cgccagcctg gtgagcttta aggcatcaa cgacgcgcag aagaaagcgg | 4620 |
| cctaccagtt cctgactat ctggtgagcc cgcaggtaaa cggcgcgtgg agccgcttta | 4680 |
| ccggctactt ctcgccgcgt aaggcttctt acgatactcc ggagatgaaa gcttatctgc | 4740 |
| agcaggatcc acgagcagcg atcgcccttg aacagctgaa gtacgcgcat ccgtggtact | 4800 |
| ccacctggga gaccgtcgcc gtgcgtaagg cgatggagaa ccagctggcg gcagtggtca | 4860 |
| acgatgccaa agtaacgccg aagccgcgg tacaggcagc gcagaaggaa gctgacgcgc | 4920 |
| taatgaaacc ttatgttgat aagactgcgc tgggagaagt gcagtag | 4967 |

<210> SEQ ID NO 5
<211> LENGTH: 1014
<212> TYPE: DNA
<213> ORGANISM: Flavobacterium sp.

<400> SEQUENCE: 5

```
atgtcgatcg gcacaggcga tcggatcaat accgtgcgcg gtcctatcac aatctctgaa      60
gcgggtttca cactgactca cgagcacatc tgcggcagct cggcaggatt cttgcgtgct     120
tggccagagt tcttcggtag ccgcaaagct ctagcggaaa aggctgtgag aggattgcgc     180
cgcgccagag cggctggcgt gcgaacgatt gtcgatgtgt cgactttcga tatcggtcgc     240
gacgtcagtt tattggccga ggtttcgcgg gctgccgacg ttcatatcgt ggcggcgacc     300
ggcttgtggt tcgacccgcc actttcgatg cgattgagga gtgtagagga actcacacag     360
ttcttcctgc gtgagattca atatggcatc gaagacaccg gaattagggc gggcattatc     420
aaggtcgcga ccacaggcaa ggcgaccccc tttcaggagt tagtgttaaa ggcggccgcc     480
cgggccagct tggccaccgg tgttccggta accactcaca cggcagcaag tcagcgcgat     540
ggtgagcagc aggccgccat ttttgagtcc gaaggcttga gcccctcacg ggtttgtatt     600
ggtcacagcg atgatactga cgatttgagc tatctcaccg ccctcgctgc gcgcggatac     660
ctcatcggtc tagaccacat cccgcacagt gcgattggtc tagaagataa tgcgagtgca     720
tcagccctcc tgggcatccg ttcgtggcaa cacgggctc tcttgatcaa ggcgctcatc     780
gaccaaggct acatgaaaca aatcctcgtt tcgaatgact ggctgttcgg gttttcgagc     840
tatgtcacca acatcatgga cgtgatggat cgcgtgaacc ccgacgggat ggccttcatt     900
ccactgagag tgatcccatt cctacgagag aagggcgtcc cacaggaaac gctggcaggc     960
atcactgtga ctaacccggc gcggttcttg tcaccgacct tgcgggcgtc atga          1014

<210> SEQ ID NO 6
<211> LENGTH: 1431
<212> TYPE: DNA
<213> ORGANISM: Pseudomonas aeruginosa

<400> SEQUENCE: 6
atgaccccag gttatcccct cgccctctct cttgccgtct ccatggccgt gctcggcagc      60
gccttgccgg cccaggcgcg ccaggacgat ccgtcactgt tcaaccgcca ggcccgtggc     120
gaactcagcg agtacggcgg cgcacggcgc gtcgagcagg acctgaccca ggccctgaag     180
cagtcgctgt cgaagaagaa ggcgaagaac gtgatcctgc tgatcggcga cggcatgggc     240
gactccgaga tcaccgtggc gcgcaactac gcgcgcggcg cgggcggcta cttcaagggt     300
atcgatgcgc tgccgctgac cggtcagtac acccactact ccctgcacaa ggacagcggc     360
ctgccggact acgtgaccga ttccgccgcc tccgccaccg cctggtccac cggggtcaag     420
tcgtacaacg gcgcgatcgg cgtggatatc cacgaacagc cgcaccgcaa cctgctggag     480
ctggccaagc tcaacggcaa ggccaccggc aacgtctcca ccgccgagct gcaggacgcc     540
acccccgccg ccctgctcgc ccacgtcacc gctcgcaagt gctacggtcc cgaggccacc     600
agcaagcagt gcccgagcaa tgccctggag aacggcggcg ccggctcgat caccgagcag     660
tggctgaaga cccgccctga cgtggttctc ggcggcggcg ccgcgacctt cgcggaaacc     720
gccaaggctg ccgctatgc cggcaagacc ctccgcgccc aggccgaagc ccgcggctac     780
cggatcgtcg agaacctcga cgagctgaaa gccgtgcgcc gcgccaacca gaagcagccg     840
ctgatcggcc tgttcgcgcc gggcaacatg ccagtcgct ggctcggtcc gaccgccacc     900
taccacggca acctgaacca gccggcggtg agctgcgagg cgaacccgaa cgcaccgcc     960
gacatcccga ccctggcgca aatgaccagc aaggccatcg agctgctgaa ggacaatccg    1020
aacggcttct tcctgcaggt cgagggcgcg tccatcgaca gcaggacca tgccgcgaat    1080
ccgtgcggcc agatcggcga gaccgtcgac ctcgacgaag ccgtgcagaa ggccctggcc    1140
```

```
tttgccaagg ccgatggcga gaccctggtg atcgtcaccg ccgaccacgc ccactccagc   1200
cagatcatcc cgccggaaac cgccgcgccg gggctgaccc aactgctcac gaccaaggac   1260
ggcgcgccgc tggcgatcag ctacggcaac tccgaggaaa gctcccagga gcacaccggc   1320
acccagttgc gcatcgccgc ctacggcccg caggccgcca atgtcaccgg cctgaccgac   1380
cagaccgacc tgttcttcac catccgtcgc gcactgaacc tgcgcgactg a            1431

<210> SEQ ID NO 7
<211> LENGTH: 504
<212> TYPE: DNA
<213> ORGANISM: Pseudomonas monteilii

<400> SEQUENCE: 7
atgaaagaac taaaaacctg gaagtgggaa gataaagaga gaacaatgct gagaaaaatc     60
tctgttggag atatattttg cctcaccaaa gacaacagca actatcattt cggtaaaatc    120
ttgtcaaaaa tgattgtagg ccacgcagtc gaaatattaa atatcactaa agacagccca    180
tcaatcaccc agcaagaact tgaacaatca gccttagcag gccgaccgct actgctagat    240
agttacgctt tattcgacaa gaaaattgac aaaggtggcg actggagaat aattggccat    300
caagagatat catcaccaga atcctatcga aactactact tcctgttcct gtacggaaca    360
cacaacaact ggaaaaaagt caacatcctc aatgaggaag ttgaaatatc aaatacagag    420
gccctaacgc tccccttgct taaagctctt agcaatcaca gattctggga aacaataaac    480
gaagaactaa agctaaactg gtaa                                           504

<210> SEQ ID NO 8
<211> LENGTH: 579
<212> TYPE: DNA
<213> ORGANISM: Rhodococcus sp.

<400> SEQUENCE: 8
ttgtctgaca agccgaatgc cgtttccagc cacaccaccc ccgacgtccc cgaagtagcg     60
gcgacgcccg agttgtccac cggcatctgc gccggtgact accgcgctgc gcttcgccgc    120 cacccccgcog gtgtcaccgt cgtgaccctc gattcgggta ccggcccggt gggtttcacc    180
gccacctcgt tctcgtccgt ctccctcgag ccgccgctcg tctcgttcaa catcgcggag    240
acgtcgtcga gcatcaatgc actcaaggca gccgagtcct ggtgatcca ccttctcggc    300 gaacatcagc agcatctggc ccagcgcttt gcgcgtagtg ccgatcagcg ttttgcagac    360
gagtcactgt gggcagtgct cgacaccggg gaaccggtgc tgcacggcac ccccagctgg    420
atgcgcgtca aggtcgacca gctgatccct gtcggcgacc acacgctggt catcggactc    480
gtcacgcggg ttcacgccga agaagacgac gaatccgctg ccgcgccgct gctctaccac    540
gagggcaagt actaccgccc gactccgtta ggtcaatag                           579

<210> SEQ ID NO 9
<211> LENGTH: 3720
<212> TYPE: DNA
<213> ORGANISM: Rhodococcus sp.

<400> SEQUENCE: 9
atgactcaac aacgacaaat gcatctggcc ggtttcttct cggccggcaa tgtgactcat     60
gcacatgggg cgtggcggca cacggacgcg tcgaatgact ttctgtcggg gaagtactac    120
caacacatcg cccgtactct ggagcgcggc aagttcgatc tgttgtttct gcctgacggg    180
```

-continued

| | |
|---|---|
| ttggccgtcg aggacagcta cggggacaac ctggacaccg gtgtcggcct gggcgggcag | 240 |
| ggtgcagtcg ccttggagcc ggccagtgtg gtcgcaacca tggccgcggt gaccgagcac | 300 |
| ctgggtcttg gggcaaccat ttcggcgacc tactatcccc cgtatcacgt tgctcgggtg | 360 |
| ttcgcgacgc tcgatcagtt gtcagggggt cgggtgtcct ggaacgtcgt cacctcgctc | 420 |
| aacgacgctg aagcgcgcaa cttcggcatt aatcagcatc tggaacacga cgcccgctat | 480 |
| gaccgcgcca tgagttctt ggaagcggtc aagaaactct ggaacagctg ggacgaggac | 540 |
| gccctcgtgc tggacaaggc ggccggcgtg ttcgccgatc ccgcgaaggt gcactacgtc | 600 |
| gatcaccacg gggagtggct gaatgtgcgc ggacctctgc aggtaccgcg ttcacctcag | 660 |
| ggtgagccgg tgatcctgca ggccggcctg tcgccccggg gtcggcgctt cgccgggaag | 720 |
| tgggccgagg ccgtcttcag tcttgcaccc aacctcgagg tgatgcaggc cacctaccag | 780 |
| ggcatcaaag ccgaggtcga cgctgcgggg cgcgatcccg atcagacgaa aatcttcacc | 840 |
| gccgtgatgc cggtactcgg cgaaagccag gcggtggcac aggaacgact ggaatatctc | 900 |
| aacagtctgg tccatccgga agtgggactg tcgacgctat ccagtcacac cggcatcaac | 960 |
| ctggcggcgt accctctcga cactccgatc aaggacatcc tgcgggatct gcaggatcgg | 1020 |
| aatgtcccga cgcaactgca catgttcgcc gccgcaacgc acagcgaaga gctcacgctg | 1080 |
| gcggaaatgg gtcggcgcta tggaaccaac gtggggttcg ttcctcagtg ggccggtacc | 1140 |
| ggggagcaga tcgctgacga gctgatccgc cacttcgagg gcggcgccgc ggatggtttc | 1200 |
| atcatctctc cggccttcct gccgggctcc tacgacgagt tcgtcgacca ggtggttccg | 1260 |
| gttctgcagg atcgcggcta cttccgcacc gagtaccagg gcaacactct gcgcgaccac | 1320 |
| ttgggtctgc gcgtaccaca actgcaagga caaccttcat gacaagccgc gtcgaccccg | 1380 |
| caaaccccgg ttcagaactc gattccgcca tccgcgacac actgacctac agcaactgcc | 1440 |
| cggtacccaa cgctctgctc acggcatcgg aatcgggctt cctcgacgcc gccggcatcg | 1500 |
| aactcgacgt cctcagcggc cagcaggca cggttcattt cacctacgac cagcctgcct | 1560 |
| acaccgtt tgggggtgag atcccgccac tgctcagcga ggggttgcgg gcacctgggc | 1620 |
| gcacgcgtct actcggcatc accccgctct tggggcgcca gggcttcttt gtccgcgacg | 1680 |
| acagcccgat cacagcggcc gccgaccttg ccggacgtcg aatcggcgtc tcggcctcgg | 1740 |
| caattcgcat cctgcgcggc cagctgggcg actacctcga gttggatccc tggcggcaaa | 1800 |
| cgctggtagc gctgggctcg tgggaggcgc gcgccttgtt gcacacccct gagcacggtg | 1860 |
| aactgggtgt ggacgacgtc gagctggtgc cgatcagcag tcctggtgtc gatgttcccg | 1920 |
| ctgagcagct cgaagaatcg gcgaccgtca agggtgcgga cctcttccc gatgtcgccc | 1980 |
| gcggtcaggc cgcggtgttg gccagcggag acgttgacgc cctgtacagt tggctgccct | 2040 |
| gggccgggga gttgcaagcc accggggccc gcccagtggt ggatctcggc ctcgatgagc | 2100 |
| gcaatgccta cgccagtgtg tggacggtca gcagcgggct ggttcgccag cgacctggcc | 2160 |
| ttgttcaacg actggtcgac gcggccgtcg acgccggct gtgggcacgc gatcattccg | 2220 |
| acgcggtgac cagcctgcac gccgcgaacc tgggcgtatc gaccggagca gtaggccagg | 2280 |
| gcttcggcgc cgacttccag cagcgtctgg ttccacgcct ggatcacgac gcctcgcccc | 2340 |
| tcctggagcg cacacagcaa ttcctgctca ccaacaactt gctgcaggaa cccgtcgccc | 2400 |
| tcgatcagtg gcggctccgg gaatttctga caacagcct caatcgccac cgataggaac | 2460 |
| atccgcatga cactgtcacc tgaaaagcag cacgttcgac cacgcgacgc cgccgacaac | 2520 |
| gatcccgtcg cggttgcccg tgggctagcc gaaaagtggc gagccaccgc cgtcgagcgt | 2580 |

```
gatcgcgccg ggggttcggc aacagccgag cgcgaagacc tgcgcgcgag cgcgctgctg   2640
tcgctcctcg tcccgcgcga atacggcggc tggggcgcag actggcccac cgccatcgag   2700
gtcgtccgcg aaatcgcggc agccgatgga tctttgggac acctgttcgg ataccacctc   2760
accaacgccc cgatgatcga actgatcggc tcgcaggaac aagaagaaca cctgtacacc   2820
cagatcgcgc agaacaactg gtggaccgga aatgcctcca gcgagaacaa cagccacgtg   2880
ctggactgga aggtcagcgc caccccgacc gaagacggcg gctacgtgct caatggcacg   2940
aagcacttct gcagcggcgc caaggggtcg gacctgctgt tcgtgttcgg cgtcgtccag   3000
gatgattctc cgcagcaggg tgcgatcatt gctgccgcta tcccgacatc gcgggctggc   3060
gttacgccca acgacgactg ggccgccatc ggcatgcggc agaccgacag cggttccacg   3120
gacttccaca acgtcaaggt cgagcctgac gaagtgctgg gcgcgcccaa cgccttcgtt   3180
ctcgccttca tacaatccga gcgcggcagc ctcttccggc ccatagcgca attgatcttc   3240
gccaacgtct atctggggat cgcgcacggc gcactcgatg ccgccaggga gtacacccgt   3300
acccaggcga ggccctggac accggccggt attcaacagg caaccgagga tccctacacc   3360
atccgctcct acggtgagtt caccatcgca ttgcagggag ctgacgccgc cgcccgtgaa   3420
gcggcccacc tgctgcagac ggtgtgggac aagggcgacg cgctcacccc cgaggaccgc   3480
ggcgaactga tggtgaaggt ctcgggagtc aaagcgttgg ccaccaacgc cgccctcaac   3540
atcagcagcg gcgtcttcga ggtgatcggc gcgcgcggaa cacatcccag gtacggtttc   3600
gaccgcttct ggcgcaacgt gcgcacccac tccctgcacg acccggtgtc ctacaagatc   3660
gccgacgtcg gcaagcacac cttgaacggt caataccccga ttcccggctt cacctcctga   3720
```

<210> SEQ ID NO 10
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Leu Pro Lys Leu Val Ile Thr His Arg Val His Asp Glu Ile Leu
1               5                   10                  15

Gln Leu Leu Ala Pro His Cys Glu Leu Met Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Val Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Gln Gly Trp Gln Pro Gln Phe Tyr Gly Thr Gly Leu Asp
    130                 135                 140

Asn Ala Thr Val Gly Ile Leu Gly Met Gly Ala Ile Gly Leu Ala Met
145                 150                 155                 160
```

Ala Asp Arg Leu Gln Gly Trp Gly Ala Thr Leu Gln Tyr His Glu Ala
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Gly Arg Gly Gln Leu Gly
                245                 250                 255

Gly Tyr Ala Ala Asp Val Phe Glu Met Glu Asp Trp Ala Arg Ala Asp
            260                 265                 270

Arg Pro Arg Leu Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
                325                 330                 335

<210> SEQ ID NO 11
<211> LENGTH: 8184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

| | |
|---|---|
| ttatcgatga taagctgtca aagatgagaa ttaattccac ggactataga ctatactaga | 60 |
| tactccgtct actgtacgat acacttccgc tcaggtcctt gtcctttaac gaggccttac | 120 |
| cactcttttg ttactctatt gatccagctc agcaaaggca gtgtgatcta agattctatc | 180 |
| ttcgcgatgt agtaaaacta gctagaccga gaaagagact agaaatgcaa aaggcacttc | 240 |
| tacaatggct gccatcatta ttatccgatg tgacgctgca gcttctcaat gatattcgaa | 300 |
| tacgctttga ggagatacag cctaatatcc gacaaactgt tttacagatt tacgatcgta | 360 |
| cttgttaccc atcattgaat tttgaacatc cgaacctggg agttttccct gaaacagata | 420 |
| gtatatttga acctgtataa taatatatag tctagcgctt tacggaagac aatgtatgta | 480 |
| tttcggttcc tggagaaact attgcatcta ttgcataggt aatcttgcac gtcgcatccc | 540 |
| cggttcattt tctgcgtttc catcttgcac ttcaatagca tatctttgtt aacgaagcat | 600 |
| ctgtgcttca ttttgtagaa caaaaatgca acgcgagagc gctaattttt caaacaaaga | 660 |
| atctgagctg cattttttaca gaacagaaat gcaacgcgaa agcgctattt taccaacgaa | 720 |
| gaatctgtgc ttcattttttg taaaacaaaa atgcaacgcg acgagagcgc taatttttca | 780 |
| aacaaagaat ctgagctgca ttttttacaga acagaaatgc aacgcgagag cgctatttta | 840 |
| ccaacaaaga atctatactt cttttttgtt ctacaaaaat gcatcccgag agcgctattt | 900 |
| ttctaacaaa gcatcttaga ttactttttt tctcctttgt gcgctctata atgcagtctc | 960 |
| ttgataactt tttgcactgt aggtccgtta aggttagaag aaggctactt tggtgtctat | 1020 |

```
tttctcttcc ataaaaaaag cctgactcca cttcccgcgt ttactgatta ctagcgaagc    1080
tgcgggtgca ttttttcaag ataaaggcat ccccgattat attctatacc gatgtggatt    1140
gcgcatactt tgtgaacaga aagtgatagc gttgatgatt cttcattggt cagaaaatta    1200
tgaacggttt cttctatttt gtctctatat actacgtata ggaaatgttt acattttcgt    1260
attgttttcg attcactcta tgaatagttc ttactacaat ttttttgtct aaagagtaat    1320
actagagata aacataaaaa atgtagaggt cgagtttaga tgcaagttca aggagcgaaa    1380
ggtggatggg taggttatat agggatatag cacagagata tatagcaaag agatacttt     1440 gagcaatgtt tgtggaagcg gtattcgcaa tttaattaag tttaaacgat ccaactggca    1500
ccgctggctt gaacaacaat accagccttc caacttctgt aaataacggc ggtacgccag    1560
tgccaccagt accgttacct ttcggtatac ctcctttccc catgtttcca atgcccttca    1620
tgcctccaac ggctactatc acaaatcctc atcaagctga cgcaagccct aagaaatgaa    1680
taacaatact gacagtacta ataattgcc tacttggctt cacatacgtt gcatacgtcg     1740
atatagataa taatgataat gacagcagga ttatcgtaat acgtaatagt tgaaaatctc    1800
aaaaatgtgt gggtcattac gtaaataatg ataggaatgg gattcttcta tttttccttt    1860
ttccattcta gcagccgtcg ggaaaacgtg gcatcctctc tttcgggctc aattggagtc    1920
acgctgccgt gagcatcctc tcttccata tctaacaact gagcacgtaa ccaatggaaa     1980
agcatgagct tagcgttgct ccaaaaaagt attggatggt taataccatt tgtctgttct    2040
cttctgactt tgactcctca aaaaaaaaa atctacaatc aacagatcgc ttcaattacg     2100
ccctcacaaa aactttttc cttcttcttc gcccacgtta aattttatcc ctcatgttgt     2160
ctaacggatt tctgcacttg atttattata aaagacaaa gacataatac ttctctatca    2220
atttcagtta ttgttcttcc ttgcgttatt cttctgttct tcttttttctt ttgtcatata   2280 taaccataac caagtaatac atattcaaaa tgaagaagcc cgagctgacc gctacctctg    2340
ttgagaagtt cctgattgag aagtttgatt ccgtttccga cctgatgcag ctgtccgagg    2400
gcgaggagtc tcgagccttc tcctttgacg tgggcggacg aggttacgtt ctgcgagtga    2460
actcgtgtgc cgacggcttc tacaaggatc gatacgtcta ccgacacttt gcttctgccg    2520
ctctgcccat ccctgaggtt tcgacattg gcgagttctc tgagtccctc acctactgca    2580
tctctcgacg agctcaggga gtcacccgc aggacctccc tgagactgag ctgcctgctg     2640
tcctccagcc tgttgctgag gccatggacg ctatcgctgc tgctgatctg tcccagacct    2700
cgggtttcgg ccccttgga cctcagggaa ttggacagta caccacttgg cgagacttca    2760
tctgtgctat tgccgatcct cacgtctacc attggcagac cgttatggac gatactgtgt    2820
cggcttctgt cgctcaggct ctggacgagc tgatgctctg gccgaggat tgcccccgagg    2880 ttcgacacct ggtgcatgct gacttcggtt ccaacaacgt tctcaccgac aacggccgaa    2940
tcactgccgt gattgactgg tccgaggcta tgtttggcga ctcgcagtac gaggtggcca    3000
acatcttctt ttggcgaccc tggctggctt gtatggagca gcagacccga tacttcgagc    3060
gacgacatcc tgagctcgct ggatcccctc gactgcgagc ttacatgctc cgaattggtc    3120
tggaccagct ctaccagtcg ctggtggatg caactttga cgatgctgcc tgggctcagg    3180
gacgatgtga cgccatcgtg cgatctggcg ctggaaccgt cggacgaact cagattgccc    3240
gacgatccgc tgctgtctgg accgacggat gcgtggaggt cctggctgat tcgggtaacc    3300
gacgaccctc tactcgacct cgagctaagg agtaataaac ggcgcgccgt taattcaaat    3360
taattgatat agttttttaa tgagtattga atctgtttag aaataatgga atattatttt    3420
```

```
tatttattta tttatattat tggtcggctc ttttcttctg aaggtcaatg acaaaatgat    3480
atgaaggaaa taatgatttc taaaatttta caacgtaaga tatttttaca aaagcctagc    3540
tcatcttttg tcaagagacc gggttggcgg cgcatttgtg tcccaaaaaa cagccccaat    3600
tgccccaatt gacccccaaat tgacccagta gcgggcccaa ccccggcgag agcccccttc    3660
tccccacata tcaaacctcc cccggttccc acacttgccg ttaagggcgt agggtactgc    3720
agtctggaat ctacgcttgt tcagactttg tactagtttc tttgtctggc catccgggta    3780
acccatgccg gacgcaaaat agactactga aaattttttt gctttgtggt tgggacttta    3840
gccaagggta taaaagacca ccgtccccga attacccttc ctcttctttt ctctctctcc    3900
ttgtcaactc acacccgaaa tcgttaagca tttccttctg agtataagaa tcattcaaaa    3960
tggtgagttt cagaggcagc agcaattgcc acgggctttg agcacacggc cgggtgtggt    4020
cccattccca tcgacacaag acgccacgtc atccgaccag cactttttgc agtactaacc    4080
gcagatgctg ccgaaactcg ttataactca ccgagtacac gatgagatcc tgcaactgct    4140
ggcgccacat tgcgagctga tgaccaacca gaccgacagc acgctgacgc gcgaggaaat    4200
tctgcgccgc tgtcgcgatg ctcaggcgat gatggcgttc atgcccgatc gggtcgatgc    4260
agactttctt caagcctgcc ctgagctgcg tgtagtcggc tgcgcgctca agggcttcga    4320
caatttcgat gtggacgcct gtactgcccg cggggtctgg ctgaccttcg tgcctgatct    4380
gttgacggtc ccgactgccg agctggcgat cggactggcg gtggggctgg ggcggcatct    4440
gcgggcagca gatgcgttcg tccgctctgg cgagttccag ggctggcaac cacagttcta    4500
cggcacgggg ctggataacg ctacggtcgg catccttggc atgggcgcca tcggactggc    4560
catggctgat cgcttgcagg gatggggcgc gaccctgcag taccacgagg cgaaggctct    4620
ggatacacaa accgagcaac ggctcggcct gcgccaggtg gcgtgcagcg aactcttcgc    4680
cagctcggac ttcatcctgc tggcgcttcc cttgaatgcc gatacccagc atctggtcaa    4740
cgccgagctg cttgccctcg tacggccggg cgctctgctt gtaaacccct gtcgtggttc    4800
ggtagtggat gaagccgccg tgctcgcggc gcttgagcga ggccagctcg gcgggtatgc    4860
ggcggatgta ttcgaaatgg aagactgggc tcgcgcggac cggccgcggc tgatcgatcc    4920
tgcgctgctc gcgcatccga atacgctgtt cactccgcac ataggtcgg cagtgcgcgc    4980
ggtgcgcctg gagattgaac gttgtgcagc gcagaacatc atccaggtat ggcaggtgc    5040
gcgcccaatc aacgctgcga accgtctgcc caaggccgag cctgccgcat gttgagcgtc    5100
tacaactgga cccttagcct gtatatatca attgattatt taaagatttg gtcggtaggc    5160
ggttcgtatt gtacaatggg atctgttact gaggtggatc tacccaactt gcgagattca    5220
attgcgagat tcaatcgcga gattcaattg cgagaatcag ttgcgagttg ttctaacact    5280
cagcttctac gagcgcttgt attaggacga gtgatactcc gtggggcgac ggcttctctt    5340
gcgtcttctg ttgtattctt tcttacacta tcgtccatct ccaaccacct cgtacgttta    5400
aacggcgcgc cttttccatag gctccgcccc cctgacgagc atcacaaaaa tcgacgctca    5460
agtcagaggt ggcgaaaccc gacaggacta taaagatacc aggcgtttcc ccctggaagc    5520
tccctcgtgc gctctcctgt tccgaccctg ccgcttaccg gatacctgtc cgcctttctc    5580
ccttcgggaa gcgtggcgct ttctcatagc tcacgctgta ggtatctcag ttcggtgtag    5640
gtcgttcgct ccaagctggg ctgtgtgcac gaaccccccg ttcagcccga ccgctgcgcc    5700
ttatccggta actatcgtct tgagtccaac ccggtaagac acgacttatc gccactggca    5760
```

```
gcagccactg gtaacaggat tagcagagcg aggtatgtag gcggtgctac agagttcttg    5820
aagtggtggc ctaactacgg ctacactaga gaacagtat ttggtatctg cgctctgctg     5880
aagccagtta ccttcggaaa aagagttggt agctcttgat ccggcaaaca aaccaccgct    5940
ggtagcggtg gttttttgt ttgcaagcag cagattacgc gcagaaaaaa aggatctcaa     6000
gaagatcctt tgatcttttc tacggggtct gacgctcagt ggaacgaaaa ctcacgttaa    6060
gggattttgg tcatgagatt atcaaaaagg atcttcacct agatcctttt aaattaaaaa    6120
tgaagtttta aatcaatcta agtatatat gagtaaactt ggtctgacag ttaccaatgc     6180
ttaatcagtg aggcacctat ctcagcgatc tgtctatttc gttcatccat agttgcctga    6240
ctccccgtcg tgtagataac tacgatacgg gagggcttac catctggccc cagtgctgca    6300
atgataccgc gagacccacg ctcaccggct ccagatttat cagcaataaa ccagccagcc    6360
ggaagggccg agcgcagaag tggtcctgca actttatccg cctccatcca gtctattaat    6420
tgttgccggg aagctagagt aagtagttcg ccagttaata gtttgcgcaa cgttgttgcc    6480
attgctacag gcatcgtggt gtcacgctcg tcgtttggta tggcttcatt cagctccggt    6540
tcccaacgat caaggcgagt tacatgatcc cccatgttgt gcaaaaaagc ggttagctcc    6600
ttcggtcctc cgatcgttgt cagaagtaag ttggccgcag tgttatcact catggttatg    6660
gcagcactgc ataattctct tactgtcatg ccatccgtaa gatgctttc tgtgactggt     6720 gagtactcaa ccaagtcatt ctgagaatag tgtatgcggc gaccgagttg ctcttgcccg    6780
gcgtcaatac gggataatac cgcgccacat agcagaactt taaaagtgct catcattgga    6840
aaacgttctt cggggcgaaa actctcaagg atcttaccgc tgttgagatc cagttcgatg    6900
taacccactc gtgcacccaa ctgatcttca gcatctttta ctttcaccag cgtttctggg    6960
tgagcaaaaa caggaaggca aaatgccgca aaaagggaa taagggcgac acggaaatgt     7020
tgaatactca tactcttcct ttttcaatat tattgaagca tttatcaggg ttattgtctc    7080
atgagcggat acatatttga atgtatttag aaaaataaac agcgatcgcg cggccgcggg    7140
taataactga tataattaaa ttgaagctct aatttgtgag tttagtatac atgcatttac    7200
ttataataca gttttttagt tttgctggcc gcatcttctc aaatatgctt cccagcctgc    7260
ttttctgtaa cgttcaccct ctaccttagc atcccttccc tttgcaaata gtcctcttcc    7320
aacaataata atgtcagatc ctgtagagac cacatcatcc acggttctat actgttgacc    7380
caatgcgtct cccttgtcat ctaaacccac accgggtgtc ataatcaacc aatcgtaacc    7440
ttcatctctt ccacccatgt ctctttgagc aataaagccg ataacaaaat ctttgtcgct    7500
cttcgcaatg tcaacagtac ccttagtata ttctccagta gctagggagc ccttgcatga    7560
caattctgct aacatcaaaa ggcctctagg ttccttttgtt acttcttccg ccgcctgctt    7620
caaaccgcta acaatacctg ggcccaccac accgtgtgca ttcgtaatgt ctgcccattc    7680
tgctattctg tatacacccg cagagtactg caatttgact gtattaccaa tgtcagcaaa    7740
ttttctgtct tcgaagagta aaaaattgta cttggcggat aatgccttta gcggcttaac    7800
tgtgccctcc atggaaaaat cagtcaagat atccacatgt gttttagta aacaaatttt     7860 gggacctaat gcttcaacta actccagtaa ttccttggtg gtacgaacat ccaatgaagc    7920
acacaagttt gtttgctttt cgtgcatgat attaaatagc ttggcagcaa caggactagg    7980
atgagtagca gcacgttcct tatatgtagc tttcgacatg atttatcttc gtttcctgca    8040
ggtttttgtt ctgtgcagtt gggttaagaa tactgggcaa tttcatgttt cttcaacacc    8100
acatatgcgt atatatacca atctaagtct gtgctccttc cttcgttctt ccttctgctc    8160
```

```
ggagattacc gaatcaaagc tagc                                              8184
```

<210> SEQ ID NO 12
<211> LENGTH: 336
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Leu Pro Lys Leu Val Ile Thr His Arg Val His Asp Glu Ile Leu
1               5                   10                  15

Gln Leu Leu Ala Pro His Cys Glu Leu Met Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Val Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Gln Gly Trp Gln Pro Gln Phe Tyr Gly Thr Gly Leu Asp
    130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Glu Ala
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Arg Leu Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
                325                 330                 335
```

<210> SEQ ID NO 13

<211> LENGTH: 9203
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

| | | | | | |
|---|---|---|---|---|---|
| gtttgtggaa | gcggtattcg | caatcattta | gtcgtgcaat | gtatgacttt | aagatttgtg | 60 |
| agcaggaaga | aaagggagaa | tcttctaacg | ataaacccct | gaaaaactgg | gtagactacg | 120 |
| ctatgttgag | ttgctacgca | ggctgcacaa | ttacacgaga | atgctcccgc | ctaggattta | 180 |
| aggctaaggg | acgtgcaatg | cagacgacag | atctaaatga | ccgtgtcggt | gaagtgttcg | 240 |
| ccaaactttt | cggttaacac | atgcagtgat | gcacgcgcga | tggtgctaag | ttacatatat | 300 |
| atatatatat | atatatatat | atatatatag | ccatagtgat | gtctaagtaa | cctttatggt | 360 |
| atatttctta | atgtggaaag | atactagcgc | gcgcacccac | acacaagctt | cgtcttttct | 420 |
| tgaagaaaag | aggaagctcg | ctaaatggga | ttccactttc | cgttccctgc | cagctgatgg | 480 |
| aaaaaggtta | gtggaacgat | gaagaataaa | aagagagatc | cactgaggtg | aaatttcagc | 540 |
| tgacagcgag | tttcatgatc | gtgatgaaca | atggtaacga | gttgtggctg | ttgccaggga | 600 |
| gggtggttct | caacttttaa | tgtatggcca | aatcgctact | tgggtttgtt | atataacaaa | 660 |
| gaagaaataa | tgaactgatt | ctcttcctcc | ttcttgtcct | ttcttaattc | tgttgtaatt | 720 |
| accttccttt | gtaattttt | ttgtaattat | tcttcttaat | aatccaaaca | aacacacata | 780 |
| ttacaataat | gaagaagccc | gagctgaccg | ctacctctgt | tgagaagttc | ctgattgaga | 840 |
| agtttgattc | cgtttccgac | ctgatgcagc | tgtccgaggg | cgaggagtct | cgagccttct | 900 |
| cctttgacgt | gggcggacga | ggttacgttc | tgcgagtgaa | ctcgtgtgcc | gacggcttct | 960 |
| acaaggatcg | atacgtctac | cgacactttg | cttctgccgc | tctgcccatc | cctgaggttc | 1020 |
| tcgacattgg | cgagttctct | gagtccctca | cctactgcat | ctctcgacga | gctcagggag | 1080 |
| tcaccctgca | ggacctccct | gagactgagc | tgcctgctgt | cctccagcct | gttgctgagg | 1140 |
| ccatggacgc | tatcgctgct | gctgatctgt | cccagacctc | gggtttcggc | ccctttggac | 1200 |
| ctcagggaat | tggacagtac | accacttggc | gagacttcat | ctgtgctatt | gccgatcctc | 1260 |
| acgtctacca | ttggcagacc | gttatggacg | atactgtgtc | ggcttctgtc | gctcaggctc | 1320 |
| tggacgagct | gatgctctgg | gccgaggatt | gccccgaggt | cgacacctg | gtgcatgctg | 1380 |
| acttcggttc | caacaacgtt | ctcaccgaca | acggccgaat | cactgccgtg | attgactggt | 1440 |
| ccgaggctat | gtttggcgac | tcgcagtacg | aggtggccaa | catcttcttt | tggcgacccct | 1500 |
| ggctggcttg | tatggagcag | cagacccgat | acttcgagcg | acgacatcct | gagctcgctg | 1560 |
| gatcccctcg | actgcgagct | tacatgctcc | gaattggtct | ggaccagctc | taccagtcgc | 1620 |
| tggtggatgg | caactttgac | gatgctgcct | gggctcaggg | acgatgtgac | gccatcgtgc | 1680 |
| gatctggcgc | tggaaccgtc | ggacgaactc | agattgcccg | acgatccgct | gctgtctgga | 1740 |
| ccgacggatg | cgtggaggtc | ctggctgatt | cgggtaaccg | acgaccctct | actcgacctc | 1800 |
| gagctaagga | gtaataaacg | gcgcgccgtc | tgaagaatga | atgatttgat | gatttctttt | 1860 |
| tccctccatt | tttcttactg | aatatatcaa | tgatatagac | ttgtatagtt | tattatttca | 1920 |
| aattaagtag | ctatatatag | tcaagataac | gtttgtttga | cacgattaca | ttattcgtcg | 1980 |
| acatcttttt | tcagcctgtc | gtggtagcaa | tttgaggagt | attattaatt | gaataggttc | 2040 |
| attttgcgct | cgcataaaca | gttttcgtca | gggacagtat | gttggaatga | gtggtaatta | 2100 |

```
atggtgacat gacatgttat agcaataacc ttgatgttta catcgtagtt taatgtacac    2160
cccgcgaatt cgttcaagta ggagtgcacc aattgcaaag ggaaaagctg aatgggcagt    2220
tcgaatagta cttttccat aggctccgcc ccctgacga gcatcacaaa atcgacgct       2280 caagtcagag gtggcgaaac ccgacaggac tataaagata ccaggcgttt ccccctggaa    2340
gctccctcgt gcgctctcct gttccgaccc tgccgcttac cggatacctg tccgcctttc    2400
tcccttcggg aagcgtggcg ctttctcata gctcacgctg taggtatctc agttcggtgt    2460
aggtcgttcg ctccaagctg ggctgtgtgc acgaaccccc cgttcagccc gaccgctgcg    2520
ccttatccgg taactatcgt cttgagtcca acccggtaag acacgactta tcgccactgg    2580
cagcagccac tggtaacagg attagcagag cgaggtatgt aggcggtgct acagagttct    2640
tgaagtggtg gcctaactac ggctacacta agaacagt atttggtatc tgcgctctgc     2700
tgaagccagt taccttcgga aaagagttg gtagctcttg atccggcaaa caaaccaccg    2760
ctggtagcgg tggttttttt gtttgcaagc agcagattac gcgcagaaaa aaggatctc    2820 aagaagatcc tttgatcttt tctacggggt ctgacgctca gtggaacgaa aactcacgtt   2880
aagggatttt ggtcatgaga ttatcaaaaa ggatcttcac ctagatcctt taaattaaa    2940 aatgaagttt taaatcaatc taaagtatat atgagtaaac ttggtctgac agttaccaat   3000
gcttaatcag tgaggcacct atctcagcga tctgtctatt tcgttcatcc atagttgcct   3060 gactcccgt cgtgtagata actacgatac gggagggctt accatctggc cccagtgctg     3120
caatgatacc gcgagaccca cgctcaccgg ctccagattt atcagcaata accagccag    3180 ccgaagggc cgagcgcaga agtggtcctg caactttatc cgcctccatc cagtctatta    3240
attgttgccg ggaagctaga gtaagtagtt cgccagttaa tagtttgcgc aacgttgttg   3300
ccattgctac aggcatcgtg gtgtcacgct cgtcgtttgg tatggcttca ttcagctccg   3360
gttcccaacg atcaaggcga gttacatgat cccccatgtt gtgcaaaaaa gcggttagct   3420
ccttcggtcc tccgatcgtt gtcagaagta agttggccgc agtgttatca ctcatggtta   3480
tggcagcact gcataattct cttactgtca tgccatccgt aagatgcttt tctgtgactg    3540
gtgagtactc aaccaagtca ttctgagaat agtgtatgcg gcgaccgagt tgctcttgcc   3600
cggcgtcaat acgggataat accgcgccac atagcagaac tttaaaagtg ctcatcattg    3660
gaaaacgttc ttcggggcga aaactctcaa ggatcttacc gctgttgaga tccagttcga    3720
tgtaacccac tcgtgcaccc aactgatctt cagcatcttt tactttcacc agcgtttctg    3780
ggtgagcaaa aacaggaagg caaaatgccg caaaaaaggg aataagggcg acacggaaat    3840
gttgaatact catactcttc cttttcaat attattgaag catttatcag ggttattgtc     3900
tcatgagcgg atacatattt gaatgtattt agaaaaataa acagcgatcg cagctagctc    3960
gtcgtgttca ggaactgttc gatggttcgg agagagtcgc cgcccagaac atacgcgcac    4020
cgatgtcagc agacagcctt attcaagta tattcaagca agtatatccg tagggtgcgg     4080
gtgatttgga tctaaggttc gtactcaaca ctcacgagca gcttgcctat gttacatcct    4140
tttatcagac ataacataat tggagtttac ttacacacgg ggtgtacctg tatgagcacc    4200
acctacaatt gtagcactgg tacttgtaca agaatttat tcgtacgaat cacagggacg     4260
gccgccctca ccgaaccagc gaataccctca gcggtcccct gcagtgactc aacaaagcga   4320
tatgaacatc ttgcgatggt atcctgctga tagttttac tgtacaaaca cctgtgtagc    4380
tccttctagc attttaagt tattcacacc tcaaggggag ggataaatta aataaattcc     4440
aaaagcgaag atcgagaaac taaattaaaa ttccaaaaac gaagttggaa cacaacccccc   4500
```

```
cgaaaaaaaa caacaaacaa aaacccaac aaaataaaca aaaacaaaat aaatatataa    4560
ctaccagtat ctgactaaaa gttcaaatac tcgtacttac aacaaataga aatgagccgg    4620
ccaaaattct gcagaaaaaa atttcaaaca agtactggta taattaaatt aaaaaacaca    4680
tcaaagtatc ataacgttag ttattttatt ttatttaata aaagaaaaca acaagatggg    4740
ctcaaaactt tcaacttata cgatacatac caaataacaa tttagtattt atctaagtgc    4800
ttttcgtaga taatggaata caaatggata tccagagtat acacatggat agtatacact    4860
gacacgacaa ttctgtatct ctttatgtta actactgtga ggcattaaat agagcttgat    4920
atataaaatg ttacatttca cagtctgaac ttttgcagat tacctaattt ggtaagatat    4980
taattatgaa ctgaaagttg atggcggccg catagcttca aaatgtttct actccttttt    5040
tactcttcca gatttctcg gactccgcgc atcgccgtac cacttcaaaa cacccaagca    5100
cagcatacta aatttcccct ctttcttcct ctagggtgtc gttaattacc cgtactaaag    5160
gtttggaaaa gaaaaagag accgcctcgt ttctttttct tcgtcgaaaa aggcaataaa    5220
aatttttatc acgtttcttt ttcttgaaaa ttttttttt tgattttttt ctctttcgat    5280
gacctcccat tgatatttaa gttaataaac ggtcttcaat ttctcaagtt tcagtttcat    5340
ttttcttgtt ctattacaac tttttttact tcttgctcat tagaaagaaa gcatagcaat    5400
ctaatctaag ttttaattac aaaatgctgc cgaaactcgt tataactcac cgagtacacg    5460
atgagatcct gcaactgctg cgccacatt gcgagctgat gaccaaccag accgacagca    5520
cgctgacgcg cgaggaaatt ctgcgccgct gtcgcgatgc tcaggcgatg atggcgttca    5580
tgcccgatcg ggtcgatgca gactttcttc aagcctgccc tgagctgcgt gtagtcggct    5640
gcgcgctcaa gggcttcgac aatttcgatg tggacgcctg tactgcccgc ggggtctggc    5700
tgaccttcgt gcctgatctg ttgacggtcc cgactgccga gctggcgatc ggactggcgg    5760
tggggctggg gcggcatctg cgggcagcag atgcgttcgt ccgctctggc gagttccagg    5820
gctggcaacc acagttctac ggcacgggc tggataacgc tacggtcggc atccttggca    5880
tgggcgccat cggactggcc atggctgatc gcttgcaggg atggggcgcg accctgcagt    5940
accacgaggc gaaggctctg gatacacaaa ccgagcaacg gctcggcctg cgccaggtgg    6000
cgtgcagcga actcttcgcc agctcggact tcatcctgct ggcgcttccc ttgaatgccg    6060
atacccagca tctggtcaac gccgagctgc ttgccctcgt acggccgggc gctctgcttg    6120 taaaccctg tcgtggttcg gtagtggatg aagccgccgt gctcgcggcg cttgagcgag    6180
gccagctcgg cgggtatgcg gcggatgtat tcgaaatgga agactgggct cgcgcggacc    6240
ggccgcggct gatcgatcct gcgctgctcg cgcatccgaa tacgctgttc actccgcaca    6300
tagggtcgga agtgcgcgcg gtgcgcctgg agattgaacg ttgtgcagcg cagaacatca    6360
tccaggtatt ggcaggtgcg cgcccaatca acgctgcgaa ccgtctgccc aaggccgagc    6420
ctgccgcatg ttgaacaggc ccctttttcct ttgtcgatat catgtaatta gttatgtcac    6480
gcttacattc acgccctcct cccacatccg ctctaaccga aaaggaagga gttagacaac    6540
ctgaagtcta ggtccctatt tatttttttt aatagttatg ttagtattaa gaacgttatt    6600
tatatttcaa attttttcttt tttttctgta caaacgcgtg tacgcatgta acattatact    6660
gaaaaccttg cttgagaagg ttttgggacg ctcgaaggct ttaatttgcg ggtaataact    6720
gatataatta aattgaagct ctaatttgtg agtttagtat acatgcattt acttataata    6780 cagttttta gttttgctgg ccgcatcttc tcaaatatgc ttcccagcct gcttttctgt    6840
```

```
aacgttcacc ctctacctta gcatcccttc cctttgcaaa tagtcctctt ccaacaataa    6900
taatgtcaga tcctgtagag accacatcat ccacggttct atactgttga cccaatgcgt    6960
ctcccttgtc atctaaaccc acaccgggtg tcataatcaa ccaatcgtaa ccttcatctc    7020
ttccacccat gtctctttga gcaataaagc cgataacaaa atctttgtcg ctcttcgcaa    7080
tgtcaacagt acccttagta tattctccag tagctaggga gcccttgcat gacaattctg    7140
ctaacatcaa aaggcctcta ggttcctttg ttacttcttc cgccgcctgc ttcaaaccgc    7200
taacaatacc tgggcccacc acaccgtgtg cattcgtaat gtctgcccat tctgctattc    7260
tgtatacacc cgcagagtac tgcaatttga ctgtattacc aatgtcagca aattttctgt    7320
cttcgaagag taaaaaattg tacttggcgg ataatgcctt tagcggctta actgtgccct    7380
ccatggaaaa atcagtcaag atatccacat gtgtttttag taaacaaatt ttgggaccta    7440
atgcttcaac taactccagt aattccttgg tggtacgaac atccaatgaa gcacacaagt    7500
ttgtttgctt ttcgtgcatg atattaaata gcttggcagc aacaggacta ggatgagtag    7560
cagcacgttc cttatatgta gctttcgaca tgatttatct tcgtttcctg caggtttttg    7620
ttctgtgcag ttgggttaag aatactgggc aatttcatgt ttcttcaaca ccacatatgc    7680
gtatatatac caatctaagt ctgtgctcct tccttcgttc ttccttctgc tcggagatta    7740
ccgaatcaaa gctagcttat cgatgataag ctgtcaaaga tgagaattaa ttccacggac    7800
tatagactat actagatact ccgtctactg tacgatacac ttccgctcag gtccttgtcc    7860
tttaacgagg ccttaccact cttttgttac tctattgatc cagctcagca aaggcagtgt    7920
gatctaagat tctatcttcg cgatgtagta aaactagcta gaccgagaaa gagactagaa    7980
atgcaaaagg cacttctaca atggctgcca tcattattat ccgatgtgac gctgcagctt    8040
ctcaatgata ttcgaatacg ctttgaggag atacagccta atatccgaca aactgtttta    8100
cagatttacg atcgtacttg ttacccatca ttgaattttg aacatccgaa cctgggagtt    8160
ttccctgaaa cagatagtat atttgaacct gtataataat atatagtcta gcgctttacg    8220
gaagacaatg tatgtatttc ggttcctgga gaaactattg catctattgc ataggtaatc    8280
ttgcacgtcg catccccggt tcattttctg cgtttccatc ttgcacttca atagcatatc    8340
tttgttaacg aagcatctgt gcttcatttt gtagaacaaa aatgcaacgc gagagcgcta    8400
attttttcaaa caaagaatct gagctgcatt tttacagaac agaaatgcaa cgcgaaagcg    8460
ctattttacc aacgaagaat ctgtgcttca tttttgtaaa acaaaaatgc aacgcgacga    8520
gagcgctaat ttttcaaaca agaatctga gctgcatttt tacagaacag aaatgcaacg    8580
cgagagcgct attttaccaa caaagaatct atacttcttt tttgttctac aaaaatgcat    8640
cccgagagcg ctattttct aacaaagcat cttagattac tttttttctc ctttgtgcgc    8700
tctataatgc agtctcttga taacttttg cactgtaggt ccgttaaggt tagaagaagg    8760
ctactttggt gtctattttc tcttccataa aaaagcctg actccacttc ccgcgtttac    8820
tgattactag cgaagctgcg ggtgcatttt ttcaagataa aggcatcccc gattatattc    8880
tataccgatg tggattgcgc atactttgtg aacagaaagt gatagcgttg atgattcttc    8940
attggtcaga aaattatgaa cggtttcttc tattttgtct ctatatacta cgtataggaa    9000
atgtttacat tttcgtattg ttttcgattc actctatgaa tagttcttac tacaattttt    9060
ttgtctaaag agtaatacta gagataaaca taaaaaatgt agaggtcgag tttagatgca    9120
agttcaagga gcgaaaggtg gatgggtagg ttatataggg atatagcaca gagatatata    9180
gcaaagagat acttttgagc aat                                             9203
```

<210> SEQ ID NO 14
<211> LENGTH: 6008
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | | | | | |
|---|---|---|---|---|---|
| ttatcgatga | taagctgtca | aagatgagaa | ttaattccac | ggactataga | ctatactaga | 60 |
| tactccgtct | actgtacgat | acacttccgc | tcaggtcctt | gtcctttaac | gaggccttac | 120 |
| cactcttttg | ttactctatt | gatccagctc | agcaaaggca | gtgtgatcta | agattctatc | 180 |
| ttcgcgatgt | agtaaaacta | gctagaccga | gaaagagact | agaaatgcaa | aaggcacttc | 240 |
| tacaatggct | gccatcatta | ttatccgatg | tgacgctgca | gcttctcaat | gatattcgaa | 300 |
| tacgctttga | ggagatacag | cctaatatcc | gacaaactgt | tttacagatt | tacgatcgta | 360 |
| cttgttaccc | atcattgaat | tttgaacatc | cgaacctggg | agttttccct | gaaacagata | 420 |
| gtatatttga | acctgtataa | taatatatag | tctagcgctt | tacggaagac | aatgtatgta | 480 |
| tttcggttcc | tggagaaact | attgcatcta | ttgcataggt | aatcttgcac | gtcgcatccc | 540 |
| cggttcattt | tctgcgtttc | catcttgcac | ttcaatagca | tatctttgtt | aacgaagcat | 600 |
| ctgtgcttca | ttttgtagaa | caaaaatgca | acgcgagagc | gctaattttt | caaacaaaga | 660 |
| atctgagctg | catttttaca | gaacagaaat | gcaacgcgaa | agcgctattt | taccaacgaa | 720 |
| gaatctgtgc | ttcattttg | taaaacaaaa | atgcaacgcg | acgagagcgc | taattttttca | 780 |
| aacaaagaat | ctgagctgca | tttttacaga | acagaaatgc | aacgcgagag | cgctatttta | 840 |
| ccaacaaaga | atctatactt | cttttttgtt | ctacaaaaat | gcatcccgag | agcgctattt | 900 |
| ttctaacaaa | gcatcttaga | ttacttttt | tctcctttgt | gcgctctata | atgcagtctc | 960 |
| ttgataactt | tttgcactgt | aggtccgtta | aggttagaag | aaggctactt | tggtgtctat | 1020 |
| tttctcttcc | ataaaaaaag | cctgactcca | cttcccgcgt | ttactgatta | ctagcgaagc | 1080 |
| tgcgggtgca | ttttttcaag | ataaaggcat | ccccgattat | attctatacc | gatgtggatt | 1140 |
| gcgcatactt | tgtgaacaga | aagtgatagc | gttgatgatt | cttcattggt | cagaaaatta | 1200 |
| tgaacggttt | cttctatttt | gtctctatat | actacgtata | ggaaatgttt | acattttcgt | 1260 |
| attgttttcg | attcactcta | tgaatagttc | ttactacaat | ttttttgtct | aaagagtaat | 1320 |
| actagagata | aacataaaaa | atgtagaggt | cgagtttaga | tgcaagttca | aggagcgaaa | 1380 |
| ggtggatggg | taggttatat | agggatatag | cacagagata | tatagcaaag | agatactttt | 1440 |
| gagcaatgtt | tgtggaagcg | gtattcgcaa | tgtttaaacc | ccagcccgac | ttttaacctc | 1500 |
| aatagctagc | tacgcaacag | acagttaaag | ctacgtactc | aactatatat | tccattgaca | 1560 |
| attgacaatt | acaactgttt | cttctcctgc | atcgttctca | tcctcattgg | cttatctcct | 1620 |
| gttatcaatt | aattataata | atatagtagt | tctgaactaa | ttacgtgatc | gcacgcagta | 1680 |
| cggctgacgc | gtattattgg | accaacaaac | cctaaaaatt | gtttcatcca | attgaacagt | 1740 |
| tcacgcaacc | gtgattgtgc | caaaaaggca | ttgccggcct | caagtaggcg | cccatgctac | 1800 |
| gactactgcg | gtctaggcgc | tcccgtatcc | ctcaatcgtg | gccctttttcc | ggtctacccg | 1860 |
| ctgagtcagc | cccgcccaac | aaaaaaagca | caccacaagt | tcgacatggt | ccaggggcac | 1920 |
| ggctgcaggg | ttgcggtata | aatacagtca | ccatttccac | cgcacctccg | tgctttgttt | 1980 |
| ttcaattggc | aacctataac | acaatgctgc | cgaaactcgt | tataactcac | cgagtacacg | 2040 |

```
atgagatcct gcaactgctg gcgccacatt gcgagctgat gaccaaccag accgacagca    2100
cgctgacgcg cgaggaaatt ctgcgccgct gtcgcgatgc tcaggcgatg atggcgttca    2160
tgcccgatcg ggtcgatgca gactttcttc aagcctgccc tgagctgcgt gtagtcggct    2220
gcgcgctcaa gggcttcgac aatttcgatg tggacgcctg tactgcccgc ggggtctggc    2280
tgaccttcgt gcctgatctg ttgacggtcc cgactgccga gctggcgatc ggactggcgg    2340
tggggctggg gcggcatctg cgggcagcag atgcgttcgt ccgctctggc gagttccagg    2400
gctggcaacc acagttctac ggcacggggc tggataacgc tacggtcggc atccttggca    2460
tgggcgccat cggactggcc atggctgatc gcttgcaggg atgggcgcg accctgcagt    2520
accacgaggc gaaggctctg gatacacaaa ccgagcaacg gctcggcctg cgccaggtgg    2580
cgtgcagcga actcttcgcc agctcggact tcatcctgct ggcgcttccc ttgaatgccg    2640
atacccagca tctggtcaac gccgagctgc ttgccctcgt acggccgggc gctctgcttg    2700
taaaccctg tcgtggttcg gtagtggatg aagccgccgt gctcgcggcg cttgagcgag    2760
gccagctcgg cgggtatgcg gcggatgtat tcgaaatgga agactgggct cgcgcggacc    2820
ggccgcggct gatcgatcct gcgctgctcg cgcatccgaa tacgctgttc actccgcaca    2880
tagggtcggc agtgcgcgcg gtgcgcctgg agattgaacg ttgtgcagcg cagaacatca    2940
tccaggtatt ggcaggtgcg cgcccaatca acgctgcgaa ccgtctgccc aaggccgagc    3000
ctgccgcatg ttgagttaat tcaaattaat tgatatagtt ttttaatgag tattgaatct    3060
gtttagaaat aatggaatat tattttatt tatttattta tattattggt cggctctttt    3120
cttctgaagg tcaatgacaa aatgatatga aggaaataat gatttctaaa attttacaac    3180
gtaagatatt tttacaaaag cctagctcat cttttgtcat taattaaggc gcgccttcc     3240
ataggctccg ccccctgac gagcatcaca aaaatcgacg ctcaagtcag aggtggcgaa    3300
acccgacagg actataaaga taccaggcgt ttccccctgg aagctccctc gtgcgctctc    3360
ctgttccgac cctgccgctt accggatacc tgtccgcctt tctcccttcg ggaagcgtgg    3420
cgctttctca tagctcacgc tgtaggtatc tcagttcggt gtaggtcgtt cgctccaagc    3480
tgggctgtgt gcacgaaccc cccgttcagc ccgaccgctg cgccttatcc ggtaactatc    3540
gtcttgagtc caacccggta agacacgact tatcgccact ggcagcagcc actggtaaca    3600
ggattagcag agcgaggtat gtaggcggtg ctacagagtt cttgaagtgg tggcctaact    3660
acggctacac tagaagaaca gtatttggta tctgcgctct gctgaagcca gttaccttcg    3720
gaaaaagagt tggtagctct tgatccggca aacaaaccac cgctggtagc ggtggttttt    3780
ttgtttgcaa gcagcagatt acgcgcagaa aaaaggatc tcaagaagat cctttgatct    3840
tttctacggg gtctgacgct cagtggaacg aaaactcacg ttaagggatt ttggtcatga    3900
gattatcaaa aaggatcttc acctagatcc ttttaaatta aaaatgaagt tttaaatcaa    3960
tctaaagtat atatgagtaa acttggtctg acagttacca atgcttaatc agtgaggcac    4020
ctatctcagc gatctgtcta tttcgttcat ccatagttgc ctgactcccc gtcgtgtaga    4080
taactacgat acgggagggc ttaccatctg gccccagtgc tgcaatgata ccgcgagacc    4140
cacgctcacc ggctccagat ttatcagcaa taaaccagcc agccggaagg gccgagcgca    4200
gaagtggtcc tgcaacttta tccgcctcca tccagtctat taattgttgc cgggaagcta    4260
gagtaagtag ttcgccagtt aatagtttgc gcaacgttgt tgccattgct acaggcatcg    4320
tggtgtcacg ctcgtcgttt ggtatggctt cattcagctc cggttcccaa cgatcaaggc    4380
```

```
gagttacatg atcccccatg ttgtgcaaaa aagcggttag ctccttcggt cctccgatcg    4440
ttgtcagaag taagttggcc gcagtgttat cactcatggt tatggcagca ctgcataatt    4500
ctcttactgt catgccatcc gtaagatgct tttctgtgac tggtgagtac tcaaccaagt    4560
cattctgaga atagtgtatg cggcgaccga gttgctcttg cccggcgtca atacgggata    4620
ataccgcgcc acatagcaga actttaaaag tgctcatcat tggaaaacgt tcttcggggc    4680
gaaaactctc aaggatctta ccgctgttga gatccagttc gatgtaaccc actcgtgcac    4740
ccaactgatc ttcagcatct tttactttca ccagcgtttc tgggtgagca aaaacaggaa    4800
ggcaaaatgc cgcaaaaaag ggaataaggg cgacacggaa atgttgaata ctcatactct    4860
tcctttttca atattattga agcatttatc agggttattg tctcatgagc ggatacatat    4920
ttgaatgtat ttagaaaaat aaacagcgat cgcgcggccg cgggtaataa ctgatataat    4980
taaattgaag ctctaatttg tgagtttagt atacatgcat ttacttataa tacagttttt    5040
tagttttgct ggccgcatct tctcaaatat gcttcccagc ctgcttttct gtaacgttca    5100
ccctctacct tagcatccct tccctttgca aatagtcctc ttccaacaat aataatgtca    5160
gatcctgtag agaccacatc atccacggtt ctatactgtt gacccaatgc gtctcccttg    5220
tcatctaaac ccacaccggg tgtcataatc aaccaatcgt aaccttcatc tcttccaccc    5280
atgtctcttt gagcaataaa gccgataaca aaatctttgt cgctcttcgc aatgtcaaca    5340
gtacccttag tatattctcc agtagctagg gagcccttgc atgacaattc tgctaacatc    5400
aaaaggcctc taggttcctt tgttacttct tccgccgcct gcttcaaacc gctaacaata    5460
cctgggccca ccacaccgtg tgcattcgta atgtctgccc attctgctat tctgtataca    5520
cccgcagagt actgcaattt gactgtatta ccaatgtcag caaattttct gtcttcgaag    5580
agtaaaaaat tgtacttggc ggataatgcc tttagcggct taactgtgcc ctccatggaa    5640
aaatcagtca agatatccac atgtgttttt agtaaacaaa ttttgggacc taatgcttca    5700
actaactcca gtaattcctt ggtggtacga acatccaatg aagcacacaa gtttgtttgc    5760
ttttcgtgca tgatattaaa tagcttggca gcaacaggac taggatgagt agcagcacgt    5820
tccttatatg tagcttttcga catgatttat cttcgtttcc tgcaggtttt tgttctgtgc    5880
agttgggtta agaatactgg gcaatttcat gtttcttcaa caccacatat gcgtatatat    5940
accaatctaa gtctgtgctc cttccttcgt tcttccttct gctcggagat taccgaatca    6000
aagctagc                                                            6008
```